US008889696B2

(12) United States Patent
Reddy et al.

(10) Patent No.: US 8,889,696 B2

(45) Date of Patent: Nov. 18, 2014

(54) SUBSTITUTED PYRIDO[2,3-D]PYRIMIDIN-7(8H)-ONES AND THERAPEUTIC USES THEREOF

(75) Inventors: E. Premkumar Reddy, Villanova, PA (US); M. V. Ramana Reddy, Upper Darby, PA (US)

(73) Assignee: Temple University—Of The Commonwealth System Of Higher Education, Philadelphia, PA (US)

( * ) Notice: Subject to any disclaimer, the term of this patent is extended or adjusted under 35 U.S.C. 154(b) by 33 days.

(21) Appl. No.: 13/516,883

(22) PCT Filed: Dec. 17, 2010

(86) PCT No.: PCT/US2010/060930

§ 371 (c)(1),
(2), (4) Date: Jun. 18, 2012

(87) PCT Pub. No.: WO2011/075616

PCT Pub. Date: Jun. 23, 2011

(65) Prior Publication Data

US 2012/0269831 A1 Oct. 25, 2012

Related U.S. Application Data

(60) Provisional application No. 61/287,784, filed on Dec. 18, 2009.

(51) Int. Cl.

| | |
|---|---|
| ***A01N 43/90*** | (2006.01) |
| ***A61K 31/519*** | (2006.01) |
| ***C07D 471/00*** | (2006.01) |
| ***C07D 487/00*** | (2006.01) |
| ***A61K 31/517*** | (2006.01) |
| ***C07D 471/04*** | (2006.01) |

(52) U.S. Cl.

CPC ............ *A61K 31/517* (2013.01); *C07D 471/04* (2013.01)

USPC ..................................... 514/264.11; 544/279

(58) Field of Classification Search

None

See application file for complete search history.

(56) References Cited

U.S. PATENT DOCUMENTS

| | | | | |
|---|---|---|---|---|
| 5,620,981 | A | 4/1997 | Blankley et al. | 514/258 |
| 5,733,914 | A | 3/1998 | Blankley et al. | 514/258 |
| 6,498,163 | B1 | 12/2002 | Boschelli et al. | 514/264.1 |
| 6,936,612 | B2 | 8/2005 | Barvian et al. | 514/252.16 |
| 7,208,489 | B2 | 4/2007 | Barvian et al. | 514/217.06 |
| 2001/0027196 | A1 | 10/2001 | Borroni et al. | 514/256 |
| 2003/0171584 | A1 | 9/2003 | Chen et al. | 544/279 |
| 2004/0224958 | A1 | 11/2004 | Booth et al. | 514/252.16 |
| 2005/0182078 | A1 | 8/2005 | Barvian et al. | 514/264.11 |
| 2006/0047118 | A1 | 3/2006 | Stadtmueller et al. | 544/184 |
| 2006/0142312 | A1 | 6/2006 | Flamme et al. | 514/264.1 |
| 2007/0179118 | A1 | 8/2007 | Barvian et al. | 514/81 |
| 2008/0004285 | A1 | 1/2008 | De Jonghe et al. | 514/252.16 |
| 2009/0062274 | A1 | 3/2009 | Baik et al. | 514/234.2 |

FOREIGN PATENT DOCUMENTS

| | | | | |
|---|---|---|---|---|
| EP | WO02064594 | * 8/2002 | | C07D 487/04 |
| WO | WO 01/70741 | 9/2001 | | C07D 471/04 |
| WO | WO 2005/105097 | 11/2005 | | A61K 31/513 |
| WO | WO 2008/016682 | 2/2008 | | A61K 31/553 |
| WO | WO 2008/047307 | 4/2008 | | C07D 471/04 |
| WO | WO 2008/150260 | 12/2008 | | C07D 471/04 |

OTHER PUBLICATIONS

Barvian, et al., "Pyrido[2,3-*d*]pyrimidin-7-one Inhibitors of Cyclin-Dependent Kinases", *J. Med. Chem.* 2000, 43, 4606-1616.

Boschelli, et al., "Synthesis and Tyrosine Kinase Inhibitory Activity of a Series of 2-Amino-8*H*-pyrido[2,3-*d*]pyrimidines: Identification of Potent, Selective Platelet-Derived Growth Factor Receptor Tyrosine Kinase Inhibitors", *J. Med. Chem.* 1998, 41, 4365-4377.

Ikuta, et al., "Crystallographic Approach to Identification of Cyclin-dependent Kinase 4 (CDK4)-specific Inhibitors by Using CDK4 Mimic CDK2 Protein", *The Journal of Biological Chemistry*, vol. 276, No. 29, pp. 27548-27554, 2001.

Klutchko, et al., "2-Substituted Aminopyrido[2,3-*d*]pyrimidin-7(8*H*)-ones. Structure-Activity Relationships Against Selected Tyrosine Kinases and in Vitro and in Vivo Anitcancer Activity", J. Med. Chem. 1998, 41, 3276-3292.

Toogood, et al., "Discovery of a Potent and Selective Inhibitor of Cyclin-Dependent Kinase 4/6", *J. Med. Chem.* 2005, 48, 2388-2406.

Trumpp-Kallmeyer, et al., "Development of a Binding Model to Protein Tyrosine Kinases for Substituted Pyrido[2,3-*d*]pyrimidine Inhibitors", *J. Med. Chem.* 1998, 41, 1752-1763.

VanderWel, et al., "Pyrido[2,3-d]pyrimidin-7-ones as Specific Inhibitors of Cyclin-Dependent Kinase 4", *J. Med. Chem.* 2005, 48, 2371-2387.

* cited by examiner

*Primary Examiner* — Jeffrey H Murray

(74) *Attorney, Agent, or Firm* — Drinker Biddle & Reath LLP

(57) ABSTRACT

Compounds useful as antiproliferative agents according to Formula (I), wherein n, A, $R^1$, $R^2$, and $Ar^1$ are as defined herein, and salts thereof; antibody conjugates, pharmaceutical compositions, methods of treatment, and synthetic methods are provided.

I

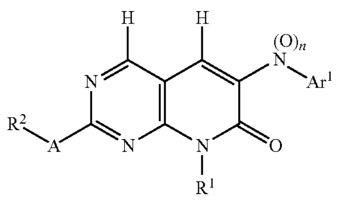

58 Claims, 3 Drawing Sheets

SUBSTITUTED PYRIDO[2,3-D]PYRIMIDIN-7(8H)-ONES AND THERAPEUTIC USES THEREOF

CROSS REFERENCE TO RELATED APPLICATIONS

This application claims the benefit of U.S. Provisional Application No. 61/287,784, filed Dec. 18, 2009, the entire disclosure of which is incorporated herein by reference.

FIELD OF THE INVENTION

The invention relates to compounds, methods for their preparation, compositions including them and methods for the treatment of cellular proliferative disorders, including, but not limited to, cancer.

BACKGROUND OF THE INVENTION

Cellular proliferative orders such as cancer are among the most common causes of death in developed countries. For diseases for which treatments exist, such as cancer, despite continuing advances, the existing treatments have undesirable side effects and limited efficacy. Identifying new effective drugs for cellular proliferative disorders, including cancer, is a continuing focus of medical research.

Mammalian Polo Kinases: There are five mammalian Polo kinases, termed Polo-like kinase (Plk) 1, 2, 3, 4 and 5. Of these, Plk1 is the most extensively characterized member and is linked to cell cycle control in the G2/M phases. The protein is relevant to cancer biologists due to its over-expression in a variety of human tumor types, whereby over-expression is linked to poor prognosis.

Plk2, or Snk has been identified as an immediate-early gene product. Studies have shown that inhibiting the expression of this gene by siRNA leads to mitotic catastrophe in paclitaxel-treated cells. Furthermore, Plk2 null mutant embryos and embryo fibroblasts display defects in cell cycle progression with respect to decreased proliferation and delayed entry into S phase, respectively, demonstrating a role for this protein in cell cycle regulation. PLK-2 plays an important role in cell cycle control through the specific phosphorylation of centrosome-associated substrates. Specifically, PLK-2 regulates centriole duplication that occurs at the G1/S border and is coordinately regulated by CDK2/cyclin E complexes, CDK2/cyclin A complexes, and PLK4.

Inhibitors of polo-like kinases tend to affect both Plk1 and Plk2, and Plk1 inhibitors have been shown to induce severe myelo-suppression in human subjects. Thus, an antiproliferative agent that is selective for inhibiting Plk2, without affecting PLk1, would be desirable.

SUMMARY OF THE INVENTION

It has been found that certain compounds and compositions are useful for the treatment of cancer and other cellular proliferative disorders. The biologically active compounds of the invention are sulfide, sulfoxide, and sulfone substituted pyrido[2,3-d]pyrimidin-7(8H)-ones.

In one aspect, the invention is directed to a compound of formula I, or a salt thereof:

I

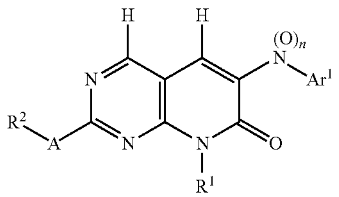

wherein:

A is $S(O)_m$ or $NR^4$;

$R^1$ is selected from the group consisting of hydrogen, $(C_1-C_6)$alkyl, $(C_3-C_7)$cycloalkyl, $(C_2-C_6)$alkenyl, and $(C_2-C_6)$alkynyl;

$R^2$ is selected from the group consisting of $(C_1-C_6)$alkyl, $(C_3-C_7)$cycloalkyl, unsubstituted $—(CH_2)_r—(C_2-C_7)$heterocycle, substituted $—(CH_2)_r—(C_2-C_7)$heterocycle, unsubstituted $(C_6-C_{10})$aryl, substituted $(C_6-C_{10})$aryl, unsubstituted $(C_2-C_9)$heterocyclyl, and substituted $(C_2-C_9)$heterocyclyl; wherein the substituted $(C_6-C_{10})$aryl, substituted $—(CH_2)_r—(C_2-C_7)$heterocycle, and substituted $(C_2-C_9)$heterocyclyl groups are substituted with one or more substituents independently selected from the group consisting of $(C_1-C_6)$alkyl, $(C_2-C_6)$alkenyl; $(C_2-C_6)$alkynyl; halogen; $—C{\equiv}N$; $—NO_2$; $—C({=}O)R^3$; $—C({=}O)OR^3$; $—C({=}O)NR^3_2$; $—C({=}NR^3)NR^3_2$; $—OR^3$; $—OC({=}O)(C_1-C_6)$alkyl; $—OC({=}O)O(C_1-C_6)$alkyl; $—OC({=}O)NR^3_2$; $—NR^3_2$; $—NR^3C({=}O)R^3$; $—NR^3C({=}O)O(C_1-C_6)$alkyl; $—NR^3C({=}O)NR^3_2$; $—NR^3SO_2R^3$; $—SR^3$; $—S(O)R^3$; $—SO_2R^3$; $—OSO_2(C_1-C_6)$alkyl; $—SO_2NR^3_2$; $(C_2-C_9)$heterocyclyl; $(C_1-C_3)$perfluoroalkyl; $—(C_2-C_6)$alkylene-$OR^3$, $—O(C_2-C_6)$alkylene-$N((C_1-C_6)$alkyl$)_2$, $—P({=}O)(OR^4)_2$; $—OP({=}O)(OR^4)_2$, 4-methylpiperazin-1-yl, 4-BOC-piperazin-1-yl, and 4-acetylpiperazin-1-yl;

m is 0, 1, or 2;

n is 0, 1, or 2;

r is 1, 2, 3, or 4;

$R^4$ is selected from the group consisting of hydrogen and $(C_1-C_6)$alkyl, wherein when $R^4$ and $R^2$ are bonded to the same nitrogen atom, $R^4$ and $R^2$ may combine to form a heterocycle or substituted heterocycle, wherein the substituted heterocycle is substituted with one or more substituents selected from the group consisting of $(C_1-C_6)$alkyl, $(C_2-C_6)$alkenyl; $(C_2-C_6)$alkynyl; halogen; $—C{\equiv}N$; $—NO_2$; $—C({=}O)R^3$; $—C({=}O)OR^3$; $—C({=}O)NR^3_2$; $—C({=}NR^3)NR^3_2$; $—OR^3$; $—OC({=}O)(C_1-C_6)$alkyl; $—OC({=}O)O(C_1-C_6)$alkyl; $—OC({=}O)NR^3_2$; $—NR^3_2$; $—NR^3C({=}O)R^3$; $—NR^3C({=}O)O(C_1-C_6)$alkyl; $—NR^3C({=}O)NR^3_2$; $—NR^3SO_2R^3$; $—SR^3$; $—S(O)R^3$; $—SO_2R^3$; $—OSO_2(C_1-C_6)$alkyl; $—SO_2NR^3_2$; $(C_1-C_3)$perfluoroalkyl; $—(C_2-C_6)$alkylene-$OR^3$, $—O(C_2-C_6)$alkylene-$N((C_1-C_6)$alkyl$)_2$, $—P({=}O)(OR^4)_2$; $—OP({=}O)(OR^4)_2$; $(C_1-C_6)$acyl; pyridyl; 3-trifluoromethylpyridyl; and 4-trifluoromethylpyridyl;

$Ar^1$ is selected from the group consisting of unsubstituted $(C_6-C_{10})$aryl, substituted $(C_6-C_{10})$aryl, unsubstituted $(C_2-C_9)$heteroaryl, substituted $(C_2-C_9)$heteroaryl, wherein the substituted $(C_6-C_{10})$aryl and substituted $(C_2-C_9)$heteroaryl groups are substituted with one to five substituents independently selected from the group consisting of $(C_1-C_6)$alkyl, $(C_2-C_6)$alkenyl; $(C_2-C_6)$alkynyl; halogen; $—C{\equiv}N$; $—NO_2$; $—C({=}O)R^3$; $—C({=}O)OR^3$; $—C({=}O)NR^3_2$; $—C({=}NR^3)NR^3_2$; $—OR^3$; $—OC({=}O)(C_1-C_6)$alkyl; $—OC({=}O)O(C_1-C_6)$alkyl; $—OC({=}O)NR^3_2$; $—NR^3_2$; $—NR^3C({=}O)R^3$; $—NR^3C({=}O)O(C_1-C_6)$alkyl; $—NR^3C({=}O)NR^3_2$; $—NR^3SO_2R^3$; $—SR^3$; $—S(O)R^3$; $—SO_2R^3$; $—OSO_2(C_1-$ $C_6$)alkyl; —$SO_2NR^3_2$; ($C_1$-$C_3$)perfluoroalkyl; —($C_2$-$C_6$)alkylene-$OR^3$, —O($C_2$-$C_6$)alkylene-N(($C_1$-$C_6$)alkyl)$_2$, —P(=O)($OR^4$)$_2$; and —OP(=O)($OR^4$)$_2$;

each $R^3$ is independently selected from the group consisting of hydrogen and ($C_1$-$C_6$)alkyl; and each $R^4$ is independently selected from the group consisting of hydrogen and ($C_1$-$C_6$)alkyl.

In one embodiment, compounds within the scope formula I comprise compounds of formula III, or a salt thereof:

III

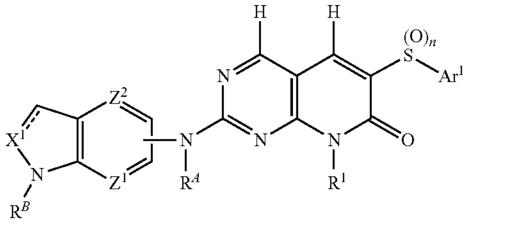

wherein:

$X^1$ is selected from the group consisting of nitrogen, $CR^5$, and C(=O);

$Z^1$ is nitrogen or $CR^5$;

$Z^2$ is nitrogen or $CR^5$;

$R^A$ is selected from the group consisting of hydrogen and ($C_1$-$C_6$)alkyl;

$R^B$ is selected from the group consisting of hydrogen, ($C_1$-$C_6$)alkyl, ($C_1$-$C_6$)acyl, unsubstituted —C(=O)—($C_6$-$C_{10}$)aryl, substituted —C(=O)—($C_6$-$C_{10}$)aryl, unsubstituted —($CH_2$)$_q$—($C_6$-$C_{10}$)aryl, substituted —($CH_2$)$_q$—($C_6$-$C_{10}$)aryl, and —C(=O)O—($C_1$-$C_6$)alkyl; wherein the substituted —C(=O)—($C_6$-$C_{10}$)aryl and substituted —($CH_2$)$_q$—($C_6$-$C_{10}$)aryl groups are substituted with one or more substituents independently selected from the group consisting of ($C_1$-$C_6$)alkyl, ($C_2$-$C_6$)alkenyl; ($C_2$-$C_6$)alkynyl; halogen; —C≡N; —$NO_2$; —C(=O)$R^6$; —C(=O)$OR^6$; —C(=O)$NR^6_2$; —C(=$NR^6$)$NR^6_2$; —$OR^6$; —OC(=O)($C_1$-$C_6$)alkyl; —OC(=O)O($C_1$-$C_6$)alkyl; —OC(=O)$NR^6_2$; —$NR^6_2$; —$NR^6$C(=O)$R^6$; —$NR^6$C(=O)O($C_1$-$C_6$)alkyl; —$NR^6$C(=O)$NR^6_2$; —$NR^6SO_2R^6$; —$SR^6$; —S(O)$R^6$; —$SO_2R^6$; —$OSO_2$($C_1$-$C_6$)alkyl; —$SO_2NR^6_2$; ($C_2$-$C_9$)heterocyclyl; ($C_1$-$C_3$)perfluoroalkyl; —($C_2$-$C_6$)alkylene-$OR^6$, —O($C_2$-$C_6$)alkylene-N(($C_1$-$C_6$)alkyl)$_2$, —P(=O)($OR^7$)$_2$; and —OP(=O)($OR^7$)$_2$;

q is 1, 2, 3, or 4;

each $R^5$ is independently selected from the group consisting of hydrogen, ($C_1$-$C_6$)alkyl, ($C_2$-$C_6$)alkenyl; ($C_2$-$C_6$)alkynyl; halogen; —C≡N; —$NO_2$; —C(=O)$R^3$; —C(=O)$OR^3$; —C(=O)$NR^3_2$; —C(=$NR^3$)$NR^3_2$; —$OR^3$; —OC(=O)($C_1$-$C_6$)alkyl; —OC(=O)O($C_1$-$C_6$)alkyl; —OC(=O)$NR^3_2$; —$NR^3_2$; —$NR^3$C(=O)$R^3$; —$NR^3$C(=O)O($C_1$-$C_6$)alkyl; —$NR^3$C(=O)$NR^3_2$; —$NR^3SO_2R^3$; —$SR^3$; —S(O)$R^3$; —$SO_2R^3$; —$OSO_2$($C_1$-$C_6$)alkyl; —$SO_2NR^3_2$; ($C_1$-$C_3$)perfluoroalkyl; —($C_2$-$C_6$)alkylene-$OR^3$, —O($C_2$-$C_6$)alkylene-N(($C_1$-$C_6$)alkyl)$_2$, —P(=O)($OR^4$)$_2$; and —OP(=O)($OR^4$)$_2$;

each $R^6$ is independently selected from the group consisting of hydrogen and ($C_1$-$C_6$)alkyl; and each $R^7$ is independently selected from the group consisting of hydrogen and ($C_1$-$C_6$)alkyl;

wherein $Ar^1$, $R^1$, $R^3$, and $R^4$ are as defined above for the compounds of formula I.

In another aspect of the invention, there is provided a process for preparing compounds according to formula I-a:

I-a

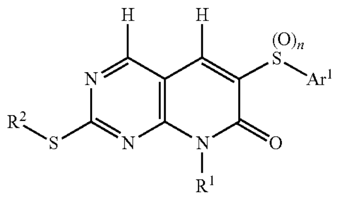

comprising:

(1) treating an aldehyde of the formula:

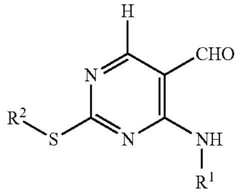

with an arylsulfonylacetic acid or ester of the formula $Ar^1$—$SO_2$—$CH_2CO_2R$, wherein R is hydrogen or ($C_1$-$C_6$)alkyl; and (2) isolating from the reaction products a compound of formula I-a, or a salt of such a compound.

In another aspect of the invention, there is provided a process for preparing compounds according to formula I-b:

I-b

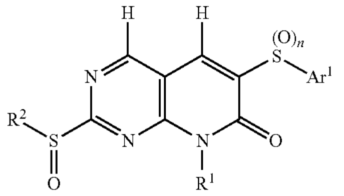

comprising:

(1) treating a compound of formula I-a, or a salt thereof,

I-a

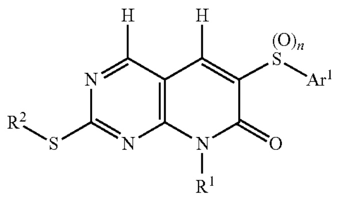

with an oxidizing agent capable of oxidizing a sulfide to a sulfoxide; and (2) isolating from the reaction products a compound of formula I-b, or a salt of such a compound.

In another aspect, a process for preparing a compound of formula I-c:

I-c

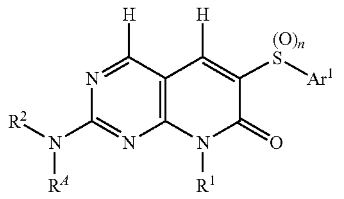

is provided comprising treating a compound of formula I-b, or a salt thereof, with an amine $R^2$—$N(R^A)H$, and isolating a compound of formula I-c, or a salt thereof.

Another aspect of the invention relates to antibody conjugates of compounds of formula I of the formula I-L-Ab, or a salt thereof, wherein I is a compound of formula I; Ab is an antibody; and -L- is a single bond or a linking group covalently linking said compound of formula I to said antibody.

In another aspect of the invention there are provided pharmaceutical compositions comprising a pharmaceutically acceptable carrier, and a compound according to formula I, or a pharmaceutically acceptable salt thereof. A pharmaceutical composition is additionally provided comprising a pharmaceutically acceptable carrier and at least one conjugate according to formula I-L-Ab, or a pharmaceutically acceptable salt thereof.

According to another embodiment of the invention, a method of treating an individual suffering from a cellular proliferative disorder, particularly cancer, is provided, comprising administering to said individual an effective amount of at least one compound according to formula I, or a pharmaceutically acceptable salt thereof, either alone, or in combination with a pharmaceutically acceptable carrier.

Also provided is a method of inducing apoptosis of cancer cells, preferably tumor cells, in an individual afflicted with cancer is provided, comprising administering to said individual an effective amount of at least one compound according to formula I, or a pharmaceutically acceptable salt thereof, either alone, or in combination with a pharmaceutically acceptable carrier.

According to another embodiment of the invention, a method of treating an individual suffering from a cellular proliferative disorder, particularly cancer, is provided, comprising administering to said individual an effective amount of at least one conjugate of the formula I-L-Ab, either alone, or in combination with a pharmaceutically acceptable carrier.

The invention is also directed to the use in medicine of a compound according to formula I, or a pharmaceutically acceptable salt thereof, or a conjugate according to formula I-L-Ab, or a pharmaceutically acceptable salt thereof.

The invention is also directed to the use of a compound according to formula I, or a pharmaceutically acceptable salt thereof, or a conjugate according to formula I-L-Ab, or a pharmaceutically acceptable salt thereof, in the preparation of a medicament for treatment of a cellular proliferative disorder, particularly cancer, or for inducing apoptosis of tumor cells in an individual affected with cancer.

According to preferred embodiments of the aforesaid compounds, conjugates, pharmaceutical compositions, methods and uses, the compound of formula I is a compound according to formula III.

Figure 2:
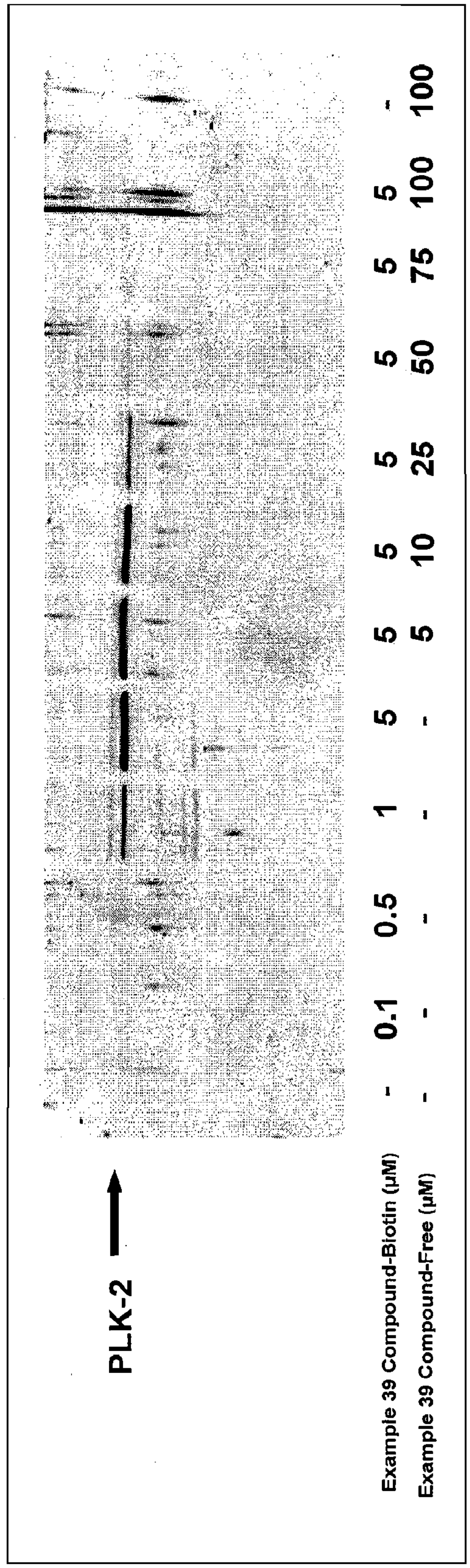
FIG. 2 shows the results of an assay of the affinity of the Example 39 compound for Plk2. Increasing concentrations of a biotinylated form of the compound were incubated with U2OS lysates. Streptavidin-conjugated agarose beads were utilized to pull down the biotinylated compound in complex with its interacting proteins. The beads were run on a denaturing gel, followed by Western blotting with anti-Plk2 antibody ("Example 39 Compound-Biotin"). For competition assays, the biotinylated Example 39 compound was combined with increasing concentrations of free Example 39 compound ("Example 39 Compound-Free").

The results of the study, shown in FIG. 2 demonstrated that Plk2 was able to form a complex with the Example 39 compound-biotin complex in a dose-dependent manner. This interaction could be readily competed out by the free (unbiotinylated) Example 39 compound, also in a dose-dependent manner.

Figure 3:
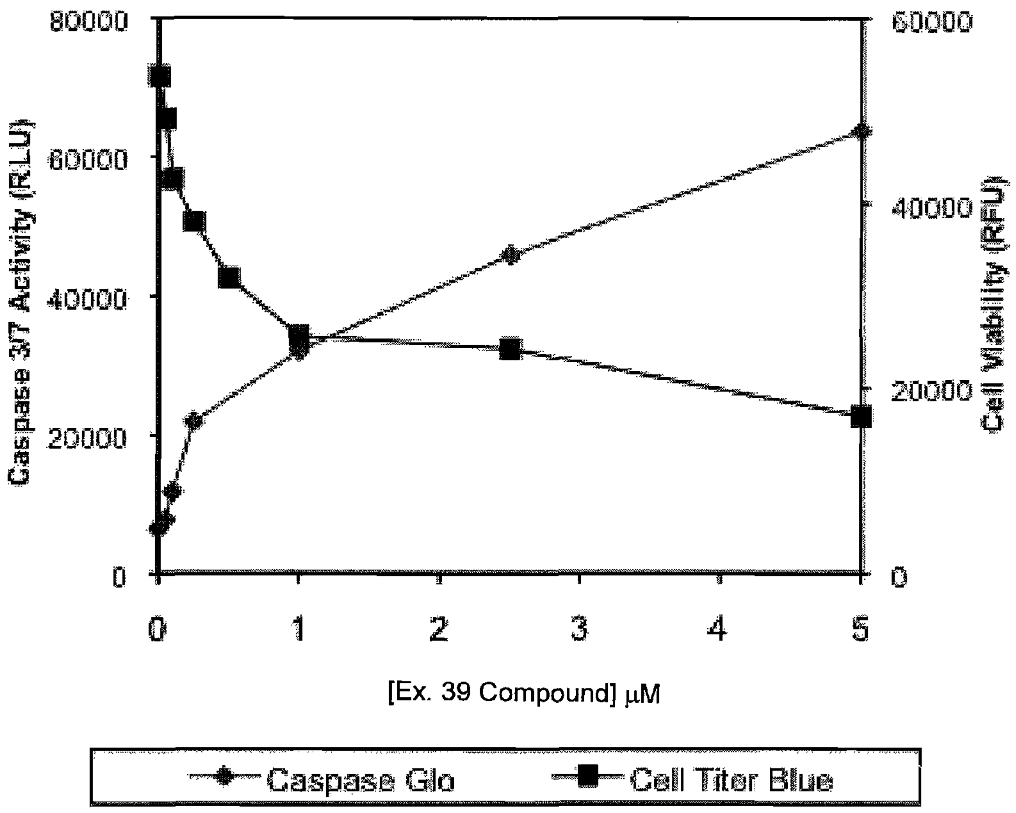

FIG. 3 shows the dose-dependent induction of apoptosis of U2OS osteosarcoma cells by the Example 39 compound, 2-(1H-indol-5-ylamino)-6-(2,4-difluorophenylsulfonyl)-8-methylpyrido[2,3-d]pyrimidin-7(8H)-one. U2OS cells were treated with increasing concentrations of the compound for 24 hours. Cell viability was measured by incubating cells with Cell Titer Blue reagent at 37° C. for 3 hours under 5% $CO_2$. Thereafter the cells were incubated with Caspase Glo reagent for 1 hour at room temperature to assay induction of Caspase 3/7 activity.

DETAILED DESCRIPTION OF THE INVENTION

The compounds and compositions of the invention are believed to selectively inhibit proliferation of cancer cells, and kill various tumor cell types without killing (or with reduced killing of) normal cells.

One compound, 2-(1H-indol-5-ylamino)-6-(2,4-difluorophenylsulfonyl)-8-methylpyrido[2,3-d]pyrimidin-7(8H)-one (Example 39) has high anticancer potency, inducing apoptosis in tumor cells at a concentration of approximately 100 nM. The compound is a highly specific and potent inhibitor of Plk2. This is significant, as inhibitors of polo-like kinases tend to affect both Plk1 and Plk2, and Plk1 inhibitors have been shown to induce severe myelo-suppression in human subjects. Preliminary results indicate that selective inhibition of Plk2 does not induce myelo-suppression in mice, suggesting that such highly selective inhibitors of Plk2, such as 2-(1H-indol-5-ylamino)-6-(2,4-difluorophenylsulfonyl)-8-methylpyrido[2,3-d]pyrimidin-7(8H)-one, are useful as non-toxic therapeutic agents.

The compounds of the invention are believed to inhibit the proliferation of tumor cells, and for some compounds, induce cell death. Cell death results from the induction of apoptosis. The compounds are believed effective against a broad range of tumor types, including but not limited to the following:

ovarian cancer, breast cancer, prostate cancer, lung cancer, renal cancer, colorectal cancer, brain cancer and leukemia.

The compounds are also believed useful in the treatment of non-cancer cellular proliferative disorders, including but not limited to the following: hemangiomatosis in newborn, secondary progressive multiple sclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis and cirrhosis.

I. DEFINITIONS

A. General

As used in the specification and the appended claims, the singular forms "a," "an" and "the" include plural referents unless the context clearly dictates otherwise.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

The expression "effective amount", when used to describe therapy to an individual suffering from a cancer or other cellular proliferative disorder, refers to the amount of a compound according to Formula I that inhibits the abnormal growth or proliferation, or alternatively induces apoptosis of cancer cells, preferably tumor cells, resulting in a therapeutically useful and selective cytotoxic effect on proliferative cells.

The term "cellular proliferative disorder" means a disorder wherein unwanted cell proliferation of one or more subsets of cells in a multicellular organism occurs. In some such disorders, cells are made by the organism at an atypically accelerated rate.

B. Chemical

In the following paragraphs some of the definitions include examples. The examples are intended to be illustrative, and not limiting. It is understood that a hashed bond mark (----) between two carbon atoms represents either a carbon-carbon single bond or a carbon-carbon double bond, as appropriate.

The term "alkyl", by itself or as part of another substituent means, unless otherwise stated, a straight, branched or cyclic chain hydrocarbon (cycloalkyl) having the number of carbon atoms designated (i.e. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$)alkyl, particularly ethyl, methyl and isopropyl. Also, ($C_3$-$C_7$)cycloalkyl is preferred.

The term "alkenyl" employed alone or in combination with other terms, means, unless otherwise stated, a stable mono-unsaturated or di-unsaturated straight chain, the unsaturation meaning a carbon-carbon double bond (—CH═CH—), branched chain or cyclic hydrocarbon group having the stated number of carbon atoms. Examples include vinyl, propenyl (allyl), crotyl, isopentenyl, butadienyl, 1,3-pentadienyl, 1,4-pentadienyl, cyclopentenyl, cyclopentadienyl and the higher homologs and isomers. Functional groups representing an alkene are exemplified by —CH═CH—$CH_2$— and $CH_2$═CH—$CH_2$—.

"Substituted alkyl" or "substituted alkenyl" means alkyl or alkenyl, as defined above, substituted by one, two or three substituents. The substituents may, for example, be selected from the group consisting of halogen, —OH, —$NH_2$, —$N(CH_3)_2$, —C(═O)OH, —C(═O)O($C_1$-$C_4$)alkyl, methoxy, ethoxy, trifluoromethyl, —C(═O)$NH_2$, —$SO_2NH_2$, —C(═NH)$NH_2$, —C≡N and —$NO_2$, preferably containing one or two substituents selected from halogen, —OH, $NH_2$, —$N(CH_3)_2$, trifluoromethyl, and —C(═O)OH, more preferably selected from halogen and —OH. Examples of substituted alkyls include, but are not limited to, 2,2-difluoropropyl, 2-carboxycyclopentyl and 3-chloropropyl.

The term "alkylene", by itself or as part of another substituent means, unless otherwise stated, a divalent straight, branched or cyclic chain hydrocarbon.

The term "alkynyl" employed alone or in combination with other terms, means, unless otherwise stated, a stable carbon-carbon triple bond-containing group branched chain or cyclic hydrocarbon group having the stated number of carbon atoms. Examples include ethynyl and propargyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

The term "alkanoyl" employed alone or in combination with other terms, means, unless otherwise stated, an alkyl group linked to the rest of the molecule through a carbonyl, i.e. ($C_1$-$C_6$)allyl-C(═O)—. Such groups include formyl, acetyl, propionyl, and the like.

The term "acyl" means a radical of the general formula R—C(═O)—, wherein R is hydrogen, hydrocarbyl, aryl, amino or alkoxy. For example, acyl includes a ($C_1$-$C_6$)alkanoyl, including substituted alkanoyl, wherein the alkyl portion can be substituted by —NR'R". Typical acyl groups include, but are not limited to, acetyl, benzoyl, phenacetyl, carboethoxy, dimethylcarbamoyl, and the like.

The term "carbamyl" or "carbamoyl" means the group —C(═O)NRR', wherein R and R' are independently selected from hydrogen or a hydrocarbyl functional group, or wherein R and R' combined form a heterocycle. Examples of carbamyl groups include: —C(═O)$NH_2$ and —C(═O)$N(CH_3)_2$.

The term "cyano" refers to a —C≡N group.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2CH_2$—OH, —$CH_2$—$CH_2$—NH—$CH_3$, —$CH_2$—S—$CH_2$—$CH_3$, and —$CH_2CH_2$—S(═O)—$CH_3$. Up to two heteroatoms may be consecutive, such as, for example, —$CH_2$—NH—$OCH_3$, or —$CH_2$—$CH_2$—S—S—$CH_3$.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—$CH_3$, —CH═CH—$CH_2$—OH, —$CH_2$—CH═N—$OCH_3$, —CH═CH—N($CH_3$)—$CH_3$, and —$CH_2$—CH═CH—$CH_2$—SH.

The terms "halo" or "halogen" by themselves or as part of another substituent mean, unless otherwise stated, a monovalent fluorine, chlorine, bromine, or iodine atom, preferably, fluorine, chlorine, or bromine, more preferably, fluorine or chlorine.

The term "nitro" refers to a —$NO_2$ group.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "($C_x$-$C_y$)perfluoroalkylene," wherein x<y, means an alkylene group with a minimum of x carbon atoms and a maximum of y carbon atoms, wherein all hydrogen atoms are replaced by fluorine atoms. Preferred is —($C_1$-$C_6$)perfluoroalkylene, more preferred is —($C_1$-$C_3$)perfluoroalkylene, most preferred is —$CF_2$—.

The term "phosphonato" means the group —P(═O)$(OH)_2$.

The term "phosphate" means the group —OP(═O)$(OR)_2$, where R can be hydrogen, alkyl, or aryl. As such phosphate esters are contemplated.

The term "sulfamyl" means the group —$SO_2$NRR', wherein R and R' are independently selected from hydrogen or a hydrocarbyl group, or wherein R and R' combined form a heterocycle. Examples of sulfamyl groups include: —$SO_2NH_2$, —$SO_2N(CH_3)_2$ and —$SO_2NH(C_6H_5)$. Preferred are —$SO_2NH_2$, $SO_2N(CH_3)_2$ and —$SO_2NHCH_3$.

The term "aromatic" generally refers to a carbocycle or heterocycle having one or more polyunsaturated rings having aromatic character (i.e. having (4n+2) delocalized π (pi) electrons where n is an integer).

The term "aryl", employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

The term "aryl-($C_1$-$C_3$)alkyl" means a functional group wherein a one to three carbon alkylene chain is attached to an aryl group, e.g., —$CH_2CH_2$-phenyl. Examples include aryl ($CH_2$)— and aryl(CH($CH_3$))—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heterocycle($C_1$-$C_3$)alkyl" means a functional group wherein a one to three carbon alkylene chain is attached to a heterocyclic group, e.g., morpholino-$CH_2CH_2$—. The term "substituted heteroaryl-($C_1$-$C_3$)alkyl" means a heteroaryl-($C_1$-$C_3$)alkyl functional group in which the heteroaryl group is substituted.

The term "arylene," by itself or as part of another substituent means, unless otherwise stated, a structure formed by the removal of a hydrogen atom from two carbons in an arene. Preferred are phenyl arylenes, particularly 1,4-phenyl arylenes.

The term "heterocycle" or "heterocyclyl" or "heterocyclic" by itself or as part of another substituent means, unless otherwise stated, an unsubstituted or substituted, stable, mono- or multi-cyclic heterocyclic ring system which consists of carbon atoms and at least one heteroatom independently selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character. Similarly, the term "heteroaryl($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted. A polycyclic heteroaryl may include fused rings. Examples include, indole, 1H-indazole, 1H-pyrrolo[2,3-b]pyridine, and the like. A polycyclic heteroaryl may include one or more rings which are partially saturated. Examples include indoline, tetrahydroquinoline and 2,3-dihydrobenzofuryl.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, N-methylpiperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Polycyclic heterocycles include both aromatic and non-aromatic polycyclic heterocycles. Examples of polycyclic heterocycles include: indolyl, particularly 3-, 4-, 5-, 6- and 7-indolyl, indolinyl, indazolyl, particularly 1H-indazol-5-yl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumaryl, dihydrocoumaryl, benzofuryl, particularly 3-, 4-, 1,5-naphthyridinyl, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, pyrrolo[2,3-b]pyridinyl, particularly 1H-pyrrolo[2,3-b]pyridin-5-yl, and quinolizidinyl. Particularly preferred are 4-indolyl, 5-indolyl, 6-indolyl, 1H-indazol-5-yl, and 1H-pyrrolo[2,3-b]pyridin-5-yl.

The aforementioned listing of heterocyclyl and heteroaryl moieties is intended to be representative and not limiting.

The term "heteroarylene" by itself or as part of another substituent means, unless otherwise stated, an arylene containing at least one hetero atom. Preferred are five- or six-membered monocyclic heteroarylene. More preferred are heteroarylene moieties comprising heteroaryl rings selected from pyridine, piperazine, pyrimidine, pyrazine, furan, thiophene, pyrrole, thiazole, imidazole and oxazole.

The term "hydrocarbyl" refers to any moiety comprising only hydrogen and carbon atoms. Preferred hydrocarbyl groups are $(C_1-C_{12})$hydrocarbyl, more preferred are $(C_1-C_7)$ hydrocarbyl, and most preferred are benzyl and $(C_1-C_6)$alkyl.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

Where a substituent is an alkyl or alkoxy group, the carbon chain may be branched, straight or cyclic, with straight being preferred.

The term "antibody" is intended to encompass not only intact antigen-binding immunoglobulin molecules, but also to include antigen-binding fragments thereof such as Fab, Fab' and $F(ab')_2$ fragments, or any other fragment retaining the antigen-binding ability of an intact antibody.

The term "monospecific polyclonal antibody" means an antibody preparation comprising multiple antibody species having specificity for a single antigen.

The term "peptidyl group" refers to a peptide functional group. Such a functional group has a chemical structure that varies from the structure of the corresponding peptide in that the structural component of the peptide, i.e., an alpha amino group, a side chain amino group, an alpha carboxyl group or a side chain carboxyl group, will form a different functionality when bonded to the molecule of which it is to be a substituent. For example, for a peptide as shown below:

$H_2N$-Val-Pro-Ala-C(═O)OH which is a substituent on a compound of formula I, the peptide is coupled to the compound of formula I such that a carboxyl moiety of said peptide is coupled to a free amine moiety on the formula I compound. Elimination of water results in the formation of an amide bond. As a practical result, the corresponding monovalent peptidyl substituent is shown to the left of the dotted line in the depiction below of the aforementioned peptide bonded to a compound of formula I:

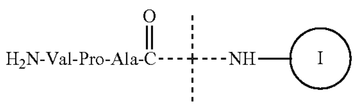

The monovalent peptide group may be attached via either an alpha- or a side chain amino group, or an alpha or side chain carboxyl group. The attachment point on the peptide group will depend on the functionality at the terminus of the group by which the peptide group is connected to the compound of formula I or an antibody.

Specifically, the peptidyl group may be coupled to a connecting group via an alpha amino or a side chain amino group when a connecting group terminates in, for example:

—C(═O)—, —C(═S)—, —S(═O)—, or $SO_2$.

Likewise, the peptidyl group may be coupled to a connecting group via an alpha carboxy or a side chain carboxy group when the connecting group terminates in:

—C(═O)$NR^5$—, —$SO_2NR^5$—, —$NR^5$—, —S— or —O—.

II. COMPOUNDS OF THE INVENTION

In one aspect, the invention is directed to a compound of formula I, or a salt thereof:

I

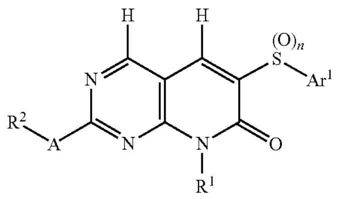

wherein:

A is $S(O)_m$ or $NR^4$;

$R^1$ is selected from the group consisting of hydrogen, $(C_1-C_6)$alkyl, $(C_3-C_7)$cycloalkyl, $(C_2-C_6)$alkenyl, and $(C_2-C_6)$ alkynyl;

$R^2$ is selected from the group consisting of $(C_1-C_6)$alkyl, $(C_3-C_7)$cycloalkyl, unsubstituted —$(CH_2)_r$—$(C_2-C_7)$heterocycle, substituted —$(CH_2)_r$—$(C_2-C_7)$heterocycle, unsubstituted $(C_6-C_{10})$aryl, substituted $(C_6-C_{10})$aryl, unsubstituted $(C_2-C_9)$heterocyclyl, and substituted $(C_2-C_9)$heterocyclyl; wherein the substituted $(C_6-C_{10})$aryl, substituted —$(CH_2)_r$—$(C_2-C_7)$heterocycle, and substituted $(C_2-C_9)$heterocyclyl groups are substituted with one or more substituents independently selected from the group consisting of $(C_1-C_6)$alkyl, $(C_2-C_6)$alkenyl; $(C_2-C_6)$alkynyl; halogen; —$NO_2$; —C(═O)$R^3$; —C(═O)$OR^3$; —C(═O)$NR^3_2$; —C(═$NR^3$)$NR^3_2$; —$OR^3$; —OC(═O)$(C_1-C_6)$alkyl; —OC(═O)O$(C_1-C_6)$alkyl; —OC(═O)$NR^3_2$; —$NR^3_2$; —$NR^3$C(═O)$R^3$; —$NR^3$C(═O)O$(C_1-C_6)$alkyl; —$NR^3$C(═O)$NR^3_2$; —$NR^3SO_2R^3$; —$SR^3$; —S(O)$R^3$; —$SO_2R^3$; —$OSO_2(C_1-C_6)$alkyl; —$SO_2NR^3_2$; $(C_2-C_9)$heterocyclyl; $(C_1-C_3)$perfluoroalkyl; —$(C_2-C_6)$alkylene-$OR^3$, —O$(C_2-C_6)$alkylene-N$((C_1-C_6)alkyl)_2$, —P(═O)$(OR^4)_2$; —OP(═O)$(OR^4)_2$, 4-methylpiperazin-1-yl, 4-BOC-piperazin-1-yl, and 4-acetylpiperazin-1-yl;

m is 0, 1, or 2;

n is 0, 1, or 2;

r is 1, 2, 3, or 4;

$R^4$ is selected from the group consisting of hydrogen and $(C_1-C_6)$alkyl, wherein when $R^4$ and $R^2$ are bonded to the same nitrogen atom, $R^4$ and $R^2$ may combine to form a heterocycle or substituted heterocycle, wherein the substituted heterocycle is substituted with one or more substituents selected from the group consisting of $(C_1-C_6)$alkyl, $(C_2-C_6)$alkenyl; $(C_2-C_6)$alkynyl; halogen; —C≡N; —$NO_2$; —C(═O)$R^3$; —C(═O)$OR^3$; —C(═O)$NR^3_2$; —C(═$NR^3$)$NR^3_2$; —$OR^3$; —OC(═O)$(C_1-C_6)$alkyl; —OC(═O)O$(C_1-C_6)$alkyl; —OC(═O)$NR^3_2$; —$NR^3_2$; —$NR^3$C(═O)$R^3$; —$NR^3$C(═O)O$(C_1-C_6)$alkyl; —$NR^3$C(═O)$NR^3_2$; —$NR^3SO_2R^3$; —$SR^3$; —S(O)$R^3$; —$SO_2R^3$; —$OSO_2(C_1-C_6)$alkyl; —$SO_2NR^3_2$; $(C_1-C_3)$perfluoroalkyl; —$(C_2-C_6)$alkylene-$OR^3$, —O$(C_2-C_6)$alkylene-N$((C_1-C_6)alkyl)_2$, —P(═O)$(OR^4)_2$; —OP(═O)$(OR^4)_2$; $(C_1-C_6)$acyl; pyridyl; 3-trifluoromethylpyridyl; and 4-trifluoromethylpyridyl;

$Ar^1$ is selected from the group consisting of unsubstituted $(C_6-C_{10})$aryl, substituted $(C_6-C_{10})$aryl, unsubstituted $(C_2-C_9)$heteroaryl, substituted $(C_2-C_9)$heteroaryl, wherein the substituted $(C_6-C_{10})$aryl and substituted $(C_2-C_9)$heteroaryl groups are substituted with one to five substituents independently selected from the group consisting of $(C_1\text{-}C_6)$alkyl, $(C_2\text{-}C_6)$alkenyl; $(C_2\text{-}C_6)$alkynyl; halogen; —C≡N; —$NO_2$; —C(═O)$R^3$; —C(═O)O$R^3$; —C(═O)N$R^3_2$; —C(═N$R^3$)N$R^3_2$; —O$R^3$; —OC(═O)$(C_1\text{-}C_6)$alkyl; —OC(═O)O$(C_1\text{-}C_6)$alkyl; —OC(═O)N$R^3_2$; —N$R^3_2$; —N$R^3$C(═O)$R^3$; —N$R^3$C(═O)O$(C_1\text{-}C_6)$alkyl; —N$R^3$C(═O)N$R^3_2$; —N$R^3$S$O_2R^3$; —S$R^3$; —S(O)$R^3$; —S$O_2R^3$; —OS$O_2(C_1\text{-}C_6)$alkyl; —S$O_2$N$R^3_2$; $(C_1\text{-}C_3)$perfluoroalkyl; —$(C_2\text{-}C_6)$alkylene-O$R^3$, —O$(C_2\text{-}C_6)$alkylene-N($(C_1\text{-}C_6)$alkyl$)_2$, —P(═O)(O$R^4)_2$; and —OP(═O)(O$R^4)_2$;

each $R^3$ is independently selected from the group consisting of hydrogen and $(C_1\text{-}C_6)$alkyl; and each $R^4$ is independently selected from the group consisting of hydrogen and $(C_1\text{-}C_6)$alkyl.

Particular embodiments of the invention are compounds according to formula I wherein:

A is $S(O)_m$; m is 0 or 1; and $R^2$ is $(C_1\text{-}C_6)$alkyl.

Particular compounds that are embodiments of the invention wherein A is $S(O)_m$; m is 0 or 1; and $R^2$ is $(C_1\text{-}C_6)$alkyl include: 2-(methylsulfanyl)-6-(phenylsulfonyl)-8-propylpyrido[2,3-d]pyrimidin-7(8H)-one; 8-cyclopentyl-2-(methylsulfanyl)-6-(phenylsulfonyl)pyrido[2,3-d]pyrimidin-7(8H)-one; 8-cyclopentyl-2-(methylsulfinyl)-6-(phenyl sulfonyl)pyrido[2,3-d]pyrimidin-7(8H)-one; 6-(4-chlorophenylsulfonyl)-8-cyclopentyl-2-(methylsulfanyl)pyrido[2,3-d]pyrimidin-7(8H)-one; and 6-(4-chlorophenylsulfonyl)-8-cyclopentyl-2-(methyl sulfinyl)pyrido[2,3-d]pyrimidin-7(8H)-one; 6-(2,4-di fluorophenyl sulfonyl)-8-methyl-2-(methylsulfanyl)pyrido[2,3-d]pyrimidin-7(8H)-one; and 6-(2,4-difluorophenylsulfonyl)-8-methyl-2-(methylsulfinyl)pyrido[2,3-d]pyrimidin-7(8H)-one.

Particular embodiments of the invention are compounds according to formula I wherein:

A is $S(O)_m$; m is 0 or 1; and $R^2$ is $(C_6\text{-}C_{10})$aryl.

A particular compound according to this embodiment is 6-(phenylsulfonyl)-2-(phenylsulfanyl)-8-propylpyrido[2,3-d]pyrimidin-7(8H)-one.

Particular embodiments of the invention are compounds according to formula I wherein:

A is $NR^A$;

$R^1$ is $(C_3\text{-}C_7)$cycloalkyl; and $Ar^1$ is unsubstituted $(C_6\text{-}C_{10})$aryl or substituted $(C_6\text{-}C_{10})$aryl.

Particular compounds that are embodiments of the invention wherein A is $NR^A$; $R^1$ is $(C_3\text{-}C_7)$cycloalkyl; and $Ar^1$ is unsubstituted $(C_6\text{-}C_{10})$aryl or substituted $(C_6\text{-}C_{10})$aryl include: 2-(5-(4-tert-butoxy carbonylpiperazin-1-yl)pyridin-2-ylamino)-8-cyclopentyl-6-(phenylsulfonyl)pyrido[2,3-d]pyrimidin-7(8H)-one; 2-(4-(4-methylpiperazin-1-yl)phenylamino)-8-cyclopentyl-6-(phenyl sulfonyl)pyrido[2,3-d]pyrimidin-7(8H)-one; 2-(4-morpholinophenylamino)-8-cyclopentyl-6-(phenylsulfonyl)pyrido[2,3-d]pyrimidin-7(8H)-one; 2-(3,4,5-trimethoxyphenylamino)-8-cyclopentyl-6-(phenylsulfonyl)pyrido[2,3-d]pyrimidin-7(8H)-one; 2-(4-(4-methylpiperazin-1-yl)phenylamino)-6-(4-chlorophenylsulfonyl)-8-cyclopentylpyrido[2,3-d]pyrimidin-7(8H)-one; 8-cyclopentyl-2-(4-(5-(trifluoromethyl)pyridin-2-yl)piperazin-1-yl)-6-(phenylsulfonyl)pyrido[2,3-d]pyrimidin-7(8H)-one; 2-(4-methoxyphenylamino)-8-cyclopentyl-6-(phenylsulfonyl)pyrido[2,3-d]pyrimidin-7(8H)-one; 6-(4-chlorophenylsulfonyl)-2-(4-morpholinophenylamino)-8-cyclohexylpyrido[2,3-d]pyrimidin-7(8H)-one; 2-(4-(4-methylpiperazin-1-yl)phenylamino)-6-(4-chlorophenyl sulfonyl)-8-cyclohexylpyrido[2,3-d]pyrimidin-7(8H)-one; and salts thereof.

In the immediately aforementioned embodiment, one preferred A is —NH—.

Particular embodiments of the invention are compounds according to formula I wherein:

A is $NR^A$;

$R^1$ is $(C_1\text{-}C_6)$alkyl; and $Ar^1$ is unsubstituted $(C_6\text{-}C_{10})$aryl or substituted $(C_6\text{-}C_{10})$aryl.

Particular compounds that are embodiments of the invention wherein A is $NR^A$; $R^1$ is $(C_1\text{-}C_6)$alkyl; and $Ar^1$ is unsubstituted $(C_6\text{-}C_{10})$aryl or substituted $(C_6\text{-}C_{10})$aryl include: 2-(4-chlorophenylamino)-6-(4-chlorophenylsulfonyl)-8-methylpyrido[2,3-d]pyrimidin-7(8H)-one; 6-(4-chlorophenylsulfonyl)-2-(4-methoxyphenylamino)-8-methylpyrido[2,3-d]pyrimidin-7(8H)-one; 6-(4-chlorophenylsulfonyl)-8-methyl-2-(quinolin-3-ylamino)pyrido[2,3-d]pyrimidin-7(8H)-one; 2-(3-morpholinopropylamino)-6-(4-chlorophenylsulfonyl)-8-methylpyrido[2,3-d]pyrimidin-7(8H)-one; 6-(4-chlorophenylsulfonyl)-2-(4-acetylpiperazin-1-yl)-8-methylpyrido[2,3-d]pyrimidin-7(8H)-one; 2-(2-(4-methylpiperazin-1-yl)ethylamino)-6-(4-chlorophenylsulfonyl)-8-methylpyrido[2,3-d]pyrimidin-7(8H)-one; 8-methyl-2-(quinolin-8-ylamino)-6-tosylpyrido[2,3-d]pyrimidin-7(8H)-one; 8-methyl-2-(quinolin-5-ylamino)-6-tosylpyrido[2,3-d]pyrimidin-7(8H)-one; 2-(4-methoxyphenylamino)-8-methyl-6-tosylpyrido[2,3-d]pyrimidin-7(8H)-one; 8-methyl-6-(phenylsulfonyl)-2-(quinolin-6-ylamino)pyrido[2,3-d]pyrimidin-7(8H)-one; 6-(2,4-difluorophenylsulfonyl)-2-(2-morpholinoethylamino)-8-methylpyrido[2,3-d]pyrimidin-7(8H)-one; and salts thereof.

In the immediately aforementioned embodiment, one preferred A is NH.

In a preferred sub-embodiment of the invention are compounds according to formula II, or a salt thereof:

II

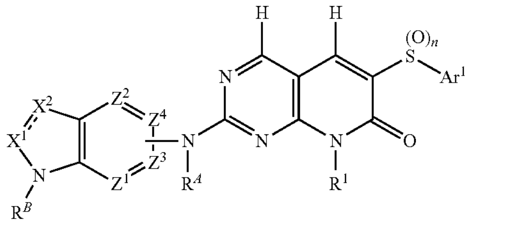

wherein:

$X^1$ is selected from the group consisting of nitrogen, $CR^5$, and C(═O);

$X^2$ is nitrogen or $CR^5$;

$Z^1$ is nitrogen or $CR^5$;

$Z^2$ is nitrogen or $CR^5$;

$Z^3$ is nitrogen or $CR^5$;

$Z^4$ is nitrogen or $CR^5$;

$R^A$ is selected from the group consisting of hydrogen and $(C_1\text{-}C_6)$alkyl;

$R^B$ is selected from the group consisting of hydrogen, $(C_1\text{-}C_6)$alkyl, $(C_1\text{-}C_6)$acyl, unsubstituted —C(═O)—$(C_6\text{-}C_{10})$aryl, substituted —C(═O)—$(C_6\text{-}C_{10})$aryl, unsubstituted —$(CH_2)_q$—$(C_6\text{-}C_{10})$aryl, substituted —$(CH_2)_q$—$(C_6\text{-}C_{10})$aryl, and —C(═O)O—$(C_1\text{-}C_6)$alkyl; wherein the substituted —C(═O)—$(C_6\text{-}C_{10})$aryl and substituted —$(CH_2)_q$—$(C_6\text{-}$ $C_{10}$)aryl groups are substituted with one or more substituents independently selected from the group consisting of ($C_1$-$C_6$) alkyl, ($C_2$-$C_6$)alkenyl; ($C_2$-$C_6$)alkynyl; halogen; —C≡N; —$NO_2$; —C(═O)$R^6$; —C(═O)$OR^6$; —C(═O)$NR^6{}_2$; —C(═$NR^6$)$NR^6{}_2$; —$OR^6$; —OC(═O)($C_1$-$C_6$)alkyl; —OC(═O)O($C_1$-$C_6$)alkyl; —OC(═O)$NR^6{}_2$; —$NR^6{}_2$; —$NR^6$C(═O)$R^6$; —$NR^6$C(═O)O($C_1$-$C_6$)alkyl; —$NR^6$C(═O)$NR^6{}_2$; —$NR^6SO_2R^6$; —$SR^6$; —S(O)$R^6$; —$SO_2R^6$; —$OSO_2$($C_1$-$C_6$)alkyl; —$SO_2NR^6{}_2$; ($C_2$-$C_9$)heterocyclyl; ($C_1$-$C_3$) perfluoro alkyl; —($C_2$-$C_6$)alkylene-$OR^6$, —O($C_2$-$C_6$) alkylene-N(($C_1$-$C_6$)alkyl)$_2$, —P(═O)$(OR^7)_2$; and —OP(═O)$(OR^7)_2$;

q is 1, 2, 3, or 4;

each $R^5$ is independently selected from the group consisting of hydrogen, ($C_1$-$C_6$)alkyl, ($C_2$-$C_6$)alkenyl; ($C_2$-$C_6$)alkynyl; halogen; —C≡N; —$NO_2$; —C(═O)$R^3$; —C(═O)$OR^3$; —C(═O)$NR^3{}_2$; —C(═$NR^3$)$NR^3{}_2$; —$OR^3$; —OC(═O)($C_1$-$C_6$)alkyl; —OC(═O)O($C_1$-$C_6$)alkyl; —OC(═O)$NR^3{}_2$; —$NR^3{}_2$; —$NR^3$C(═O)$R^3$; —$NR^3$C(═O)O($C_1$-$C_6$)alkyl; —$NR^3$C(═O)$NR^3{}_2$; —$NR^3SO_2R^3$; —$SR^3$; —S(O)$R^3$; —$SO_2R^3$; —$OSO_2$($C_1$-$C_6$)alkyl; —$SO_2NR^3{}_2$; ($C_1$-$C_3$) perfluoroalkyl; —($C_2$-$C_6$)alkylene-$OR^3$, —O($C_2$-$C_6$) alkylene-N(($C_1$-$C_6$)alkyl)$_2$, —P(═O)$(OR^4)_2$; and —OP(═O)$(OR^4)_2$;

each $R^6$ is independently selected from the group consisting of hydrogen and ($C_1$-$C_6$)alkyl; and each $R^7$ is independently selected from the group consisting of hydrogen and ($C_1$-$C_6$)alkyl.

Other substituents including $Ar^1$, $R^1$, $R^3$, K and $R^4$, have been defined above with respect to formula I.

In other particular embodiments of this sub-embodiment according to formula II, $R^1$ is ($C_1$-$C_6$)alkyl or ($C_3$-$C_7$)cycloalkyl.

In other particular embodiments of this sub-embodiment according to formula II, $Ar^1$ is unsubstituted ($C_6$-$C_{10}$)aryl or substituted ($C_6$-$C_{10}$)aryl.

In other particular embodiments of this sub-embodiment according to formula II, $R^A$ is hydrogen.

In other particular embodiments of this sub-embodiment according to formula II, n is 1 or 2.

In a preferred sub-embodiment of the invention are compounds according to formula III, or a salt thereof:

III

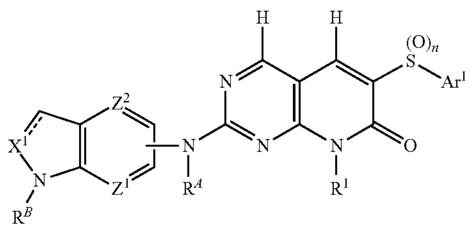

wherein:

$X^1$ is selected from the group consisting of nitrogen, $CR^5$, and C(═O);

$Z^1$ is nitrogen or $CR^5$;

$Z^2$ is nitrogen or $CR^5$;

$R^A$ is selected from the group consisting of hydrogen and ($C_1$-$C_6$)alkyl;

$R^B$ is selected from the group consisting of hydrogen, ($C_1$-$C_6$)alkyl, ($C_1$-$C_6$)acyl, unsubstituted —C(═O)—($C_6$-$C_{10}$) aryl, substituted —C(═O)—($C_6$-$C_{10}$)aryl, unsubstituted —$(CH_2)_q$—($C_6$-$C_{10}$)aryl, substituted —$(CH_2)_q$—($C_6$-$C_{10}$) aryl, and —C(═O)O—($C_1$-$C_6$)alkyl; wherein the substituted —C(═O)—($C_6$-$C_{10}$)aryl and substituted —$(CH_2)_q$—($C_6$-$C_{10}$)aryl groups are substituted with one or more substituents independently selected from the group consisting of ($C_1$-$C_6$) alkyl, ($C_2$-$C_6$)alkenyl; ($C_2$-$C_6$)alkynyl; halogen; —CN; —$NO_2$; —C(═O)$R^6$; —C(═O)$OR^6$; —C(═O)$NR^6{}_2$; —C(═$NR^6$)$NR^6{}_2$; —$OR^6$; —OC(═O)($C_1$-$C_6$)alkyl; —OC(═O)O($C_1$-$C_6$)alkyl; —OC(═O)$NR^6{}_2$; —$NR^6{}_2$; —$NR^6$C(═O)$R^6$; —$NR^6$C(═O)O($C_1$-$C_6$)alkyl; —$NR^6$C(═O)$NR^6{}_2$; —$NR^6SO_2R^6$; —$SR^6$; —S(O)$R^6$; —$SO_2R^6$; —$OSO_2$($C_1$-$C_6$)alkyl; —$SO_2NR^6{}_2$; ($C_2$-$C_9$)heterocyclyl; ($C_1$-$C_3$) perfluoroalkyl; —($C_2$-$C_6$)alkylene-$OR^6$, —O($C_2$-$C_6$) alkylene-N(($C_1$-$C_6$)alkyl)$_2$, —P(═O)$(OR^7)_2$; and —OP(═O)$(OR^7)_2$;

q is 1, 2, 3, or 4;

each $R^5$ is independently selected from the group consisting of hydrogen, ($C_1$-$C_6$)alkyl, ($C_2$-$C_6$)alkenyl; ($C_2$-$C_6$)alkynyl; halogen; —C≡N; —$NO_2$; —C(═O)$R^3$; —C(═O)$OR^3$; —C(═O)$NR^3{}_2$; —C(═$NR^3$)$NR^3{}_2$; —$OR^3$; —OC(═O)($C_1$-$C_6$)alkyl; —OC(═O)O($C_1$-$C_6$)alkyl; —OC(═O)$NR^3{}_2$; —$NR^3{}_2$; —$NR^3$C(═O)$R^3$; —$NR^3$C(═O)O($C_1$-$C_6$)alkyl; —$NR^3$C(═O)$NR^3{}_2$; —$NR^3SO_2R^3$; —$SR^3$; —S(O)$R^3$; —$SO_2R^3$; —$OSO_2$($C_1$-$C_6$)alkyl; —$SO_2NR^3{}_2$; ($C_1$-$C_3$) perfluoroalkyl; —($C_2$-$C_6$)alkylene-$OR^3$, —O($C_2$-$C_6$) alkylene-N(($C_1$-$C_6$)alkyl)$_2$, —P(═O)$(OR^4)_2$; and —OP(═O)$(OR^4)_2$;

each $R^6$ is independently selected from the group consisting of hydrogen and ($C_1$-$C_6$)alkyl; and each $R^7$ is independently selected from the group consisting of hydrogen and ($C_1$-$C_6$)alkyl.

Other substituents including $Ar^1$, $R^1$, $R^3$, and $R^4$, have been defined above with respect to formula I and formula II.

In other particular embodiments of this sub-embodiment according to formula III, $R^A$ is hydrogen.

In other particular embodiments of this sub-embodiment according to formula III, $R^1$ is ($C_3$-$C_7$)cycloalkyl.

In other particular embodiments of this sub-embodiment according to formula III, $Ar^1$ is unsubstituted ($C_6$-$C_{10}$)aryl or substituted ($C_6$-$C_{10}$)aryl.

In other particular embodiments of this sub-embodiment according to formula III, n is 1 or 2.

Particular compounds of formula III that are embodiments of the invention wherein $R^A$ is hydrogen; $R^1$ is ($C_3$-$C_7$)cycloalkyl; n is 2; and $Ar^1$ is unsubstituted ($C_6$-$C_{10}$)aryl or substituted ($C_6$-$C_{10}$)aryl include: 2-(1H-indol-5-ylamino)-8-cyclopentyl-6-(phenyl sulfonyl)pyrido[2,3-d]pyrimidin-7(8H)-one; and 2-(1H-indol-5-ylamino)-6-(4-chlorophenyl sulfonyl)-8-cyclohexylpyrido[2,3-d]pyrimidin-7(8H)-one.

In other particular embodiments of this sub-embodiment according to formula III, $R^1$ is ($C_1$-$C_6$)alkyl.

In other particular embodiments of this sub-embodiment according to formula III, $X^1$ is selected from the group consisting of nitrogen and C(═O).

Particular compounds of formula III that are embodiments of the invention wherein $R^A$ is hydrogen; $R^1$ is ($C_1$-$C_6$)alkyl; n is 2; $Ar^1$ is unsubstituted ($C_6$-$C_{10}$)aryl or substituted ($C_6$-$C_{10}$)aryl; and $X^1$ is selected from the group consisting of nitrogen and C(═O) include: 2-(1H-indazol-5-ylamino)-6-(4-fluorophenyl sulfonyl)-8-methylpyrido[2,3-d]pyrimidin-7(8H)-one; 2-(2-oxoindolin-5-ylamino)-8-methyl-6-tosylpyrido[2,3-d]pyrimidin-7(8H)-one; 2-(2-oxo indolin-5-ylamino)-6-(3-chloro-4-fluorophenylsulfonyl)-8-methylpyrido[2,3-d]pyrimidin-7(8H)-one; 2-(1H-indazol-5-ylamino)-6-(3-chloro-4-fluorophenyl sulfonyl)-8-methylpyrido[2,3-d]pyrimidin-7(8H)-one; 2-(1H-indazol-5-ylamino)-6-(2,4-difluorophenyl sulfonyl)-8-methylpyrido[2, 3-d]pyrimidin-7(8)-one; and 6-(2,4-difluorophenylsulfonyl)-2-(2-oxoindolin-5-ylamino)-8-methylpyrido[2,3-d]pyrimidin-7(8H)-one.

In other particular embodiments of this sub-embodiment according to formula III, $X^1$ is CH, and hashed bond (----) represents a carbon-carbon double bond.

In other particular embodiments of this sub-embodiment according to formula III, $Z^2$ is CH, and hashed bond (----) represents a carbon-carbon double bond.

In other particular embodiments of this sub-embodiment according to formula III, $X^1$ is CH, $Z^2$ is CH, and hashed bond (----) represents a carbon-carbon double bond.

In other particular embodiments of this sub-embodiment according to formula III, $X^1$ is CH, $Z^1$ is CH, $Z^2$ is CH, and hashed bond (----) represents a carbon-carbon double bond.

Particular compounds of formula III that are embodiments of the invention wherein $R^A$ is hydrogen; $R^1$ is $(C_1\text{-}C_6)$alkyl; n is 2; $Ar^1$ is unsubstituted $(C_6\text{-}C_{10})$aryl or substituted $(C_6\text{-}C_{10})$aryl; $X^1$ is CH; $Z^2$ is CH; and hashed bond (----) represents a carbon-carbon double bond include: 2-(1H-indol-5-ylamino)-6-(4-chlorophenylsulfonyl)-8-methylpyrido[2,3-d]pyrimidin-7(8H)-one; 2-(1H-indol-4-ylamino)-6-(4-fluorophenylsulfonyl)-8-methylpyrido[2,3-d]pyrimidin-7(8H)-one; 2-(1H-indol-5-ylamino)-6-(4-fluorophenylsulfonyl)-8-methylpyrido[2,3-d]pyrimidin-7(8H)-one; 2-(1H-indol-5-ylamino)-6-(2,4-difluorophenylsulfonyl)-8-methylpyrido[2,3-d]pyrimidin-7(8H)-one; 2-(1H-pyrrolo[2,3-b]pyridin-5-ylamino)-6-(4-fluorophenyl sulfonyl)-8-methylpyrido[2,3-d]pyrimidin-7(8H)-one; 2-(1H-indol-4-ylamino)-8-methyl-6-tosylpyrido[2,3-d]pyrimidin-7(8H)-one; 2-(1H-indol-5-ylamino)-8-methyl-6-tosylpyrido[2,3-d]pyrimidin-7(8H)-one; 2-(1H-indol-5-ylamino)-6-(4-bromophenylsulfonyl)-8-methylpyrido[2,3-d]pyrimidin-7(8H)-one; 2-(1H-pyrrolo[2,3-b]pyridin-5-ylamino)-8-methyl-6-tosylpyrido[2,3-d]pyrimidin-7(8H)-one; 2-(1H-indol-5-ylamino)-8-methyl-6-(phenylsulfonyl)pyrido[2,3-d]pyrimidin-7(8H)-one; 2-(1H-pyrrolo[2,3-b]pyridin-5-ylamino)-8-methyl-6-(phenylsulfonyl)pyrido[2,3-d]pyrimidin-7(8H)-one; 2-(1H-indol-6-ylamino)-6-(4-fluorophenylsulfonyl)-8-methylpyrido[2,3-d]pyrimidin-7(8H)-one; 2-(1H-indol-6-ylamino)-8-methyl-6-(phenylsulfonyl)pyrido[2,3-d]pyrimidin-7(8H)-one; methyl 4-(2-(1H-indol-5-ylamino)-7,8-dihydro-8-methyl-7-oxopyrido[2,3-d]pyrimidin-6-ylsulfonyl)benzoate; 2-(1H-indol-5-ylamino)-8-ethyl-6-(phenylsulfonyl)pyrido[2,3-d]pyrimidin-7(8H)-one; 2-(1H-indol-6-ylamino)-8-methyl-6-tosylpyrido[2,3-d]pyrimidin-7(8H)-one; 2-(1H-indol-5-ylamino)-6-(4-methoxyphenylsulfonyl)-8-methylpyrido[2,3-d]pyrimidin-7(8H)-one; 2-(1H-indol-4-ylamino)-6-(4-methoxyphenylsulfonyl)-8-methylpyrido[2,3-d]pyrimidin-7(8H)-one; 2-(1H-indol-5-ylamino)-6-(phenylsulfonyl)-8-propylpyrido[2,3-d]pyrimidin-7(8H)-one; 2-(1H-indol-4-ylamino)-6-(4-chlorophenylsulfonyl)-8-methylpyrido[2,3-d]pyrimidin-7(8H)-one; 2-(1H-pyrrolo[2,3-b]pyridin-5-ylamino)-6-(4-chlorophenylsulfonyl)-8-methylpyrido[2,3-d]pyrimidin-7(8H)-one; 2-(1H-indol-5-ylamino)-6-(3-chloro-4-fluorophenylsulfonyl)-8-methylpyrido[2,3-d]pyrimidin-7(8H)-one; 2-(1H-indol-4-ylamino)-6-(phenylsulfonyl)-8-propylpyrido[2,3-d]pyrimidin-7(8H)-one; 2-(1H-indol-6-ylamino)-6-(phenylsulfonyl)-8-propylpyrido[2,3-d]pyrimidin-7(8H)-one; 2-(1H-indol-4-ylamino)-6-(3-chloro-4-fluorophenylsulfonyl)-8-methylpyrido[2,3-d]pyrimidin-7(8H)-one; 2-(1H-pyrrolo[2,3-b]pyridin-5-ylamino)-6-(3-chloro-4-fluorophenylsulfonyl)-8-methylpyrido[2,3-d]pyrimidin-7(8H)-one; 2-(1H-indol-5-ylamino)-6-(2,4-difluorophenylsulfonyl)-8-methylpyrido[2,3-d]pyrimidin-7(8H)-one; 2-(1H-indol-5-ylamino)-6-(4-hydroxyphenylsulfonyl)-8-methylpyrido[2,3-d]pyrimidin-7(8H)-one; 4-(2-(1H-indol-5-ylamino)-7,8-dihydro-8-methyl-7-oxopyrido[2,3-d]pyrimidin-6-ylsulfonyl)benzoic acid; and salts thereof.

In other particular embodiments of this sub-embodiment according to formula III, $R^1$ is hydrogen. A particular compound of this embodiment is 2-(1H-indol-5-ylamino)-6-(3-chloro-4-fluorophenylsulfonyl)pyrido[2,3-d]pyrimidin-7(8H)-one.

In other particular embodiments of the invention, $Ar^1$ is independently selected from the group consisting of unsubstituted and substituted phenyl, preferably substituted phenyl.

In particular embodiments of the invention, $R^2$ is unsubstituted $(C_2\text{-}C_9)$heteroaryl or substituted $(C_2\text{-}C_9)$heteroaryl. Particularly preferred are 4-indolyl, 5-indolyl, 6-indolyl, 1H-indazol-5-yl, 1H-pyrrolo[2,3-b]pyridin-5-yl, and the like, which can be further substituted with one, two, three, four, or five substituents independently selected from the group consisting of $(C_1\text{-}C_6)$alkyl, $(C_2\text{-}C_6)$alkenyl; $(C_2\text{-}C_6)$alkynyl; halogen; —C≡N; $—NO_2$; $—C(=O)R^3$; $—C(=O)OR^3$; $—C(=O)NR^3_2$; $—C(=NR^3)NR^3_2$; $—OR^3$; $—OC(=O)(C_1\text{-}C_6)$alkyl; $—OC(=O)O(C_1\text{-}C_6)$alkyl; $—OC(=O)NR^3_2$; $—NR^3_2$; $—NR^3C(=O)R^3$; $—NR^3C(=O)O(C_1\text{-}C_6)$alkyl; $—NR^3C(=O)NR^3_2$; $—NR^3SO_2R^3$; $—SR^3$; $—S(O)R^3$; $—SO_2R^3$; $—OSO_2(C_1\text{-}C_6)$alkyl; $—SO_2NR^3_2$; $(C_2\text{-}C_9)$heterocyclyl; $(C_1\text{-}C_3)$perfluoroalkyl; $—(C_2\text{-}C_6)$alkylene-$OR^3$, $—O(C_2\text{-}C_6)$alkylene-$N((C_1\text{-}C_6)alkyl)_2$, $—P(=O)(OR^4)_2$; $—OP(=O)(OR^4)_2$, 4-methylpiperazin-1-yl, 4-BOC-piperazin-1-yl, and 4-acetylpiperazin-1-yl.

It is to be understood that other particular and preferred embodiments of the compounds of the invention will combine the features of the particular and preferred embodiments of the invention explicitly described above. Embodiments defined by such combinations are contemplated as particular embodiments of the invention.

In other preferred embodiments the compound of formulas I, or any of the embodiments thereof, is an isolated compound. In other preferred embodiments, the compound of formulas I, and compositions containing the compounds, including pharmaceutical compositions, are substantially free of pharmaceutically unacceptable contaminants. A pharmaceutically unacceptable contaminant is a substance which, if present in more than an insubstantial amount, would render the compound or composition unsuitable for use as a pharmaceutical for therapeutic administration. Examples include toxic materials such as halogenated solvents and heavy metals, and potentially infectious materials such as bacteria, fungi, viruses, and bacterial and fungal spores.

III. METHODS FOR PREPARING COMPOUNDS OF THE INVENTION AND INTERMEDIATES USEFUL IN THE SYNTHESIS OF COMPOUNDS OF THE INVENTION

There are provided processes for preparing compounds according to formula I, intermediates that are useful in the preparation of such compounds, and processes for preparing such intermediates.

A method for preparing a compound of formula I-a:

I-a

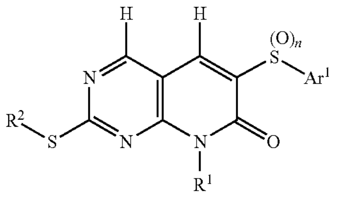

is provided.

The compound of formula I-a may be prepared by a process comprising:

(1) treating an aldehyde of the formula:

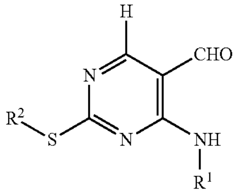

with an arylsulfonylacetic acid or ester of the formula $Ar^1$—$SO_2$—$CH_2CO_2R$, wherein R is hydrogen or $(C_1\text{-}C_6)$alkyl; and (2) isolating from the reaction products a compound of formula I-a, or a salt of such a compound.

In one embodiment of the aforesaid process for preparing a compound of formula I-a, n is 2, R' is methyl, and $R^2$ is methyl. According to a particularly preferred process, n is 2, $R^1$ is methyl, $R^2$ is methyl, and $Ar^1$ is 2,4-difluorophenyl.

A method for preparing a compound of formula I-b:

I-b

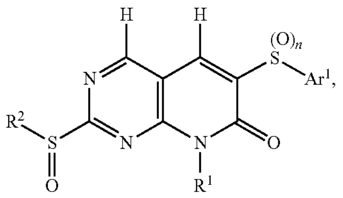

is provided.

The compound of formula I-b may be prepared by a process comprising:

(1) treating a compound of formula I-a, or a salt thereof,

I-a

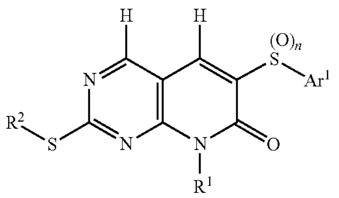

with an oxidizing agent capable of oxidizing a sulfide to a sulfoxide; and (2) isolating from the reaction products a compound of formula I-b, or a salt of such a compound.

In one embodiment of the aforesaid process for preparing a compound of formula I-b, n is 2, $R^1$ is methyl, and $R^2$ is methyl. According to a particularly preferred process, n is 2, $R^1$ is methyl, $R^2$ is methyl, and $Ar^1$ is 2,4-difluorophenyl.

In another aspect, a process for preparing a compound of formula I-c:

I-c

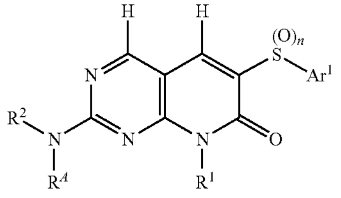

is provided comprising treating a compound of formula I-b, or a salt thereof, with an amine $R^2$—$N(R^A)H$, and isolating a compound of formula I-c, or a salt thereof.

Further, there are provided processes for preparing compounds according to formula III. In one embodiment, there is provided a process for preparing compounds according to the formula III:

III

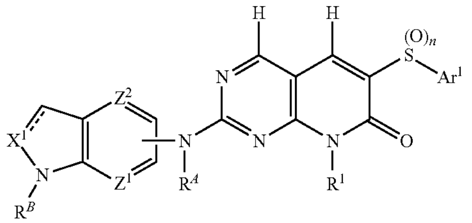

comprising, (1) treating a compound of formula I-b, or a salt thereof,

I-b

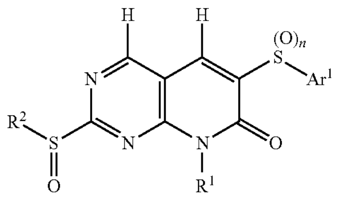

with an amine of the formula A:

A

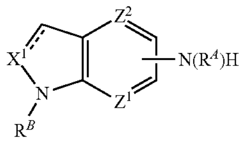

wherein:

$X^1$ is selected from the group consisting of nitrogen, $CR^5$, and C(═O);

$Z^1$ is nitrogen or $CR^5$;

$Z^2$ is nitrogen or $CR^5$;

$R^B$ is selected from the group consisting of hydrogen, ($C_1$-$C_6$)alkyl, ($C_1$-$C_6$)acyl, unsubstituted —C(═O)—($C_6$-$C_{10}$) aryl, substituted —C(═O)—($C_6$-$C_{10}$)aryl, unsubstituted —$(CH_2)_q$—($C_6$-$C_{10}$)aryl, substituted —$(CH_2)_q$—($C_6$-$C_{10}$) aryl, and —C(═O)O—($C_1$-$C_6$)alkyl; wherein the substituted —C(═O)—($C_6$-$C_{10}$)aryl and substituted —$(CH_2)_q$—($C_6$-$C_{10}$)aryl groups are substituted with one or more substituents independently selected from the group consisting of ($C_1$-$C_6$) alkyl, ($C_2$-$C_6$)alkenyl; ($C_2$-$C_6$)alkynyl; halogen; —CN; —$NO_2$; —C(═O)$R^6$; —C(═O)$OR^6$; —C(═O)$NR^6_2$; —C(═$NR^6$)$NR^6_2$; —$OR^6$; —OC(═O)($C_1$-$C_6$)alkyl; —OC(═O)O($C_1$-$C_6$)alkyl; —OC(═O)$NR^6_2$; —$NR^6_2$; —$NR^6$C(═O)$R^6$; —$NR^6$C(═O)O($C_1$-$C_6$)alkyl; —$NR^6$C(═O)$NR^6_2$; —$NR^6SO_2R^6$; —$SR^6$; —S(O)$R^6$; —$SO_2R^6$; —$OSO_2$($C_1$-$C_6$)alkyl; —$SO_2NR^6_2$; ($C_2$-$C_9$)heterocyclyl; ($C_1$-$C_3$) perfluoroalkyl; —($C_2$-$C_6$)alkylene-$OR^6$, —O($C_2$-$C_6$) alkylene-N(($C_1$-$C_6$)alkyl)$_2$, —P(═O)$(OR^7)_2$; and —OP(═O)$(OR^7)_2$;

q is 1, 2, 3, or 4;

each $R^5$ is independently selected from the group consisting of hydrogen, ($C_1$-$C_6$)alkyl, ($C_2$-$C_6$)alkenyl; ($C_2$-$C_6$)alkynyl; halogen; —C≡N; —$NO_2$; —C(═O)$R^3$; —C(═O)$OR^3$; —C(═O)$NR^3_2$; —C(═$NR^3$)$NR^3_2$; —$OR^3$; —OC(═O)($C_1$-$C_6$)alkyl; —OC(═O)O($C_1$-$C_6$)alkyl; —OC(═O)$NR^3_2$; —$NR^3_2$; —$NR^3$C(═O)$R^3$; —$NR^3$C(═O)O($C_1$-$C_6$)alkyl; —$NR^3$C(═O)$NR^3_2$; —$NR^3SO_2R^3$; —$SR^3$; —S(O)$R^3$; —$SO_2R^3$; —$OSO_2$($C_1$-$C_6$)alkyl; —$SO_2NR^3_2$; ($C_1$-$C_3$) perfluoroalkyl; —($C_2$-$C_6$)alkylene-$OR^3$, —O($C_2$-$C_6$) alkylene-N(($C_1$-$C_6$)alkyl)$_2$, —P(═O)$(OR^4)_2$; and —OP(═O)$(OR^4)_2$;

each $R^6$ is independently selected from the group consisting of hydrogen and ($C_1$-$C_6$)alkyl; and each $R^7$ is independently selected from the group consisting of hydrogen and ($C_1$-$C_6$)alkyl; and (2) isolating from the reaction products a compound of formula III, or a salt of such a compound.

In one embodiment of the aforesaid process for preparing a compound of formula III, n is 2, $R^1$ is methyl, $R^2$ is methyl, $Z^1$ is carbon, $Z^2$ is carbon, $R^A$ is hydrogen, $R^B$ is hydrogen. According to a particularly preferred embodiment, n is 2, $R^1$ is methyl, $R^2$ is methyl, $Z^1$ is carbon, $Z^2$ is carbon, $R^A$ is hydrogen, $R^B$ is hydrogen and $Ar^1$ is 2,4-difluorophenyl. In one such embodiment, the amine of formula A is 5-aminoindole.

The compounds can be prepared by a variety of synthetic routes. Representative procedures are shown in Schemes 1-6. It will be readily apparent that the compounds can be synthesized by substitution of the appropriate starting materials, reactants, and reagents in the syntheses shown below. It will also be apparent that the selective protection and deprotection steps, as well as the order of the steps themselves, can be carried out in varying order, depending on the nature of the reactions. Precursor compounds, intermediates, and reagents are commercially available or can be prepared from commercially available starting materials. The following schemes are representative, and are in no way intended to limit the scope of the compounds in the embodiments of the present invention.

In the text, formulae and schemes that follow, unless otherwise indicated A, $R^1$, $R^2$, $R^A$, $R^B$, m, and n are as defined above for formulas I and III.

Scheme 1

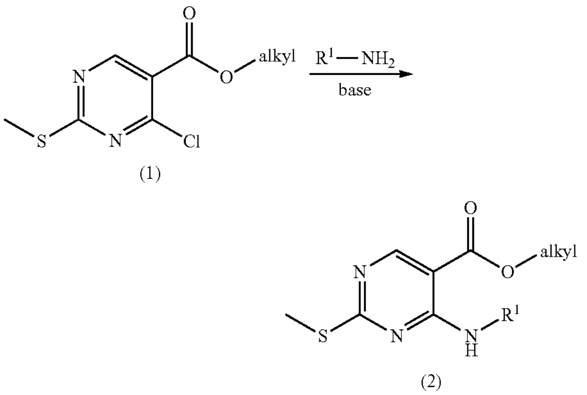

(1)

(2)

A synthesis of compounds of formula (2) is shown in Scheme 1. Alkyl 4-substituted-amino-2-methylsulfanyl-pyrimidine-5-carboxylates (2) can be prepared by reaction of a 4-halopyrimidine carboxylate such as alkyl 4-chloro-2-methylsulfanyl-pyrimidine-5-carboxylate (1) with an amine $R^1$—$NH_2$ in the presence of a base in a polar or aprotic solvent with heating. Useful bases include organic bases, for example, tertiary amines such as diisopropylethylamine (DIPEA) or triethylamine (TEA). Useful solvents can include acetonitrile, p-dioxane, or N,N,-dimethylformamide (DMF). Heating at about 100° C. can be employed.

Scheme 2

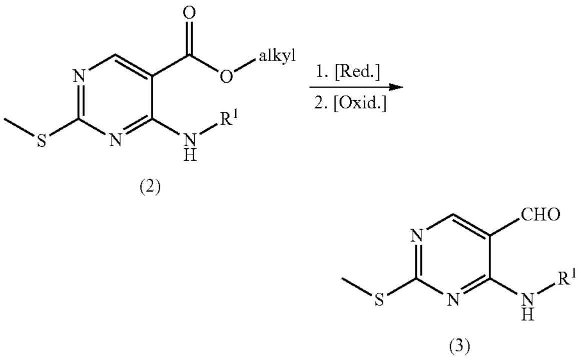

(2)

(3)

A synthesis of compounds of formula (3) is shown in Scheme 2. Ester (2) can be reduced using a reducing agent such as lithium aluminum hydride (LAH) in a polar solvent, to provide an alcohol intermediate (—$CH_2OH$). Other useful reducing agents include diisobutylaluminum hydride (DIBAL-H), borane-THF complex, and the like. Useful solvents include tetrahydrofuran (THF), diethyl ether, and the like. The intermediate alcohol can be oxidized to aldehyde (3) using an oxidizing agent such as manganese dioxide in a halogenated solvent. Other useful oxidizing agents include pyridinium dichromate (PDC), and the like. Useful halogenated solvents include dichloromethane, chloroform, and the like. Alternatively, the ester (2) can be converted directly to aldehyde (3) by treatment with DIBAL-H in a solvent such as dichloromethane, THF, or toluene.

Scheme 3

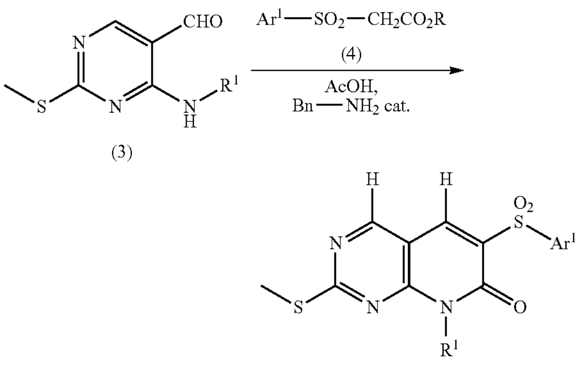

(3)

(I-a')

A synthesis of compounds of formula (I-a') is shown in Scheme 3. 4-Substituted-amino-2-methylsulfanylpyrimidine-5-carboxaldehyde (3) can be condensed with arylsulfonyl acetic acid or ester compounds of formula (4) (R=hydrogen or ($C_1$-$C_6$)alkyl) in acetic acid under heating, to provide a 6,8-substituted-2-methylsulfanylpyrido[2,3-d]pyrimidin-7(8H)-one compound of formula (I-a'). A catalytic amount of benzylamine can be used in the condensation reaction. Temperatures for the condensation reaction can range from about 100° C. to about 120° C. (reflux).

Scheme 4

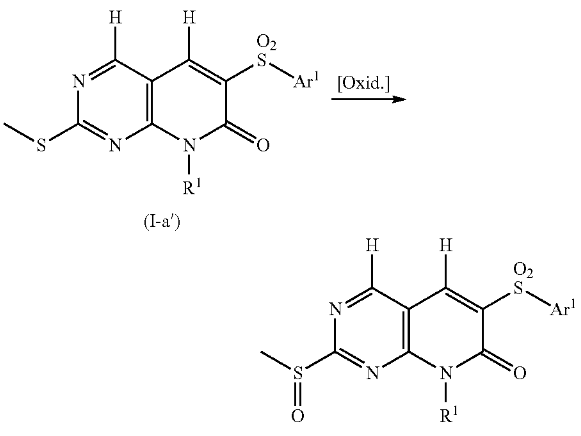

(I-a')

(I-b')

A synthesis of compounds of formula (I-b') is shown in Scheme 4. The 2-methylsulfanylpyrido[2,3-d]pyrimidin-7(8H)-one compound of formula (I-a') can be oxidized to a sulfoxide, that is a 2-methylsulfinylpyrido[2,3-d]pyrimidin-7(8H)-one compound of formula (I-b'), by treatment of (I-a') with an oxidizing agent. Useful oxidizing agents can include, but are not limited to, meta-chloroperoxybenzoic acid (m-CPBA), hydrogen peroxide, sodium hypochlorite, sodium periodate, tert-butyl hypochlorite, and peracids such as peracetic acid. Stoichiometric use of the oxidizing agent can be employed if necessary to control the oxidation state of sulfur. Useful solvents include acetic acid and halogenated solvents such as chloroform or dichloromethane, and the like. A preferred oxidizing reagent is m-CPBA in chloroform.

Scheme 5

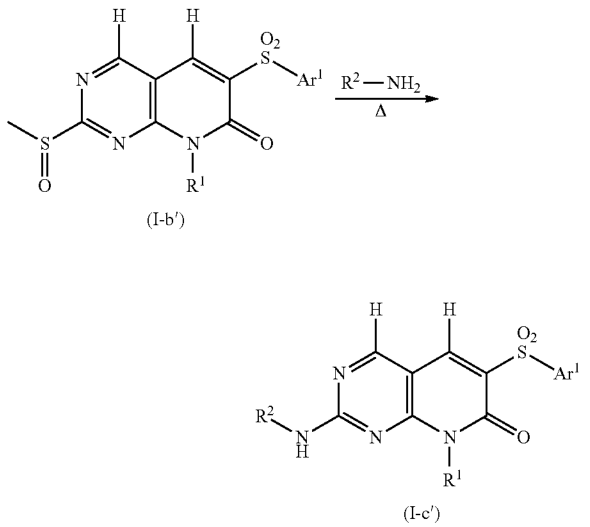

(I-b')

(I-c')

A synthesis of compounds of formula (I-c') is shown in Scheme 5. The 2-methylsulfinylpyrido[2,3-d]pyrimidin-7(8H)-one compound of formula (I-b') can be treated with an amine compound of formula $R^2$—$NH_2$ (5) to provide a compound of formula (I-c'), a 2-amino-substituted-6-arylsulfonylpyrido[2,3-d]pyrimidin-7(8H)-one. The sulfinyl group of compound (1-b') is susceptible to nucleophilic substitution with diverse amine compounds (5). Exemplary solvents include benzenoid solvents such as toluene, o-xylene, m-xylene, o-xylene, xylene mixtures, anisole, and mixtures thereof. Other useful solvents include p-dioxane, 1,2-dimethoxyethane (DME), THF, and the like. Useful temperatures to effect substitution reaction can range from about 100° C. to about 150° C. (reflux). A molar excess of the amine (5) can be used, for example up to 1.5 to 2.0 equivalents.

Preferred amine compounds (5) include anilines, substituted anilines, and other fused-ring anilines. Particularly preferred amine compounds (5) include heteroaryl amines, substituted heteroaryl amines, heterocyclic amines, and substituted heterocyclic amines. Exemplary heteroaryl amines include 4-aminoindole, 5-aminoindole, 6-aminoindole, 5-aminoindazole, 1H-pyrrolo[2,3-b]pyridin-5-amine, and the like.

In order to further illustrate the above nucleophilic substitution, a synthesis of compounds of formula III is shown in Scheme 6 below.

Scheme 6

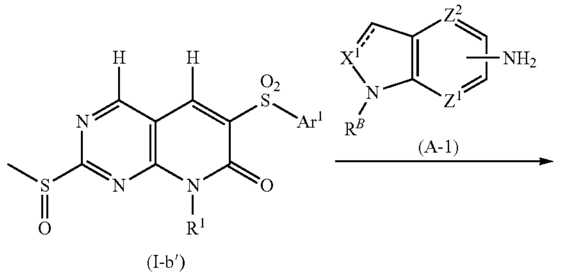

(A-1)

(I-b')

-continued

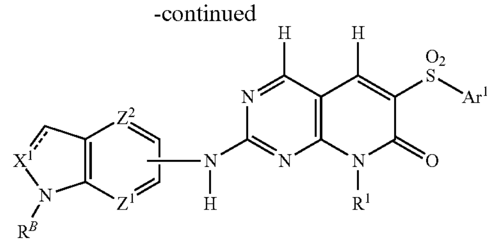

(III-a)

In the preparation of a compound of formula (III-a) as shown in Scheme 6, a heteroaryl amine compound of formula (A-1) can be used as a nucleophile in a substitution reaction of the compound of formula (I-b'). A useful solvent is toluene (reflux).

The aforementioned oxidation processes are carried out by reacting the starting material with an appropriate oxidizing agent in a suitable solvent at an appropriate temperature. Suitable solvents for such oxidation processes typically include alcohols, for example methanol or ethanol, carboxylic acids, for example acetic acid, or chlorinated solvents, for example dichloromethane or chloroform. Suitable oxidizing agents typically include hydrogen peroxide, carboxylic peracids, such as m-chloroperoxybenzoic acid, or persulfate salts, such as potassium peroxymonosulfate. In the case of inorganic oxidizing agents such as potassium peroxymonosulfate, hydroxylic solvents such as alcohols are preferred, and the solvent typically contains water in an amount sufficient to cause the oxidizing agent to remain in solution. The reactions are typically carried out at a temperature between 0° C. and the reflux temperature of the solvent, which is typically about 100° C. The person skilled in the art will know how to select suitable oxidizing agents and reaction conditions. For example, under mild conditions such as low temperature and using a limiting amount of oxidizing agent, selective oxidation of thioethers to sulfoxides can often be achieved, whereas under more forcing conditions such as using excess oxidizing agent, higher temperature, or prolonged reaction times oxidation of thioethers or sulfoxides to sulfones can be achieved. Certain reagents (e.g. sodium periodate) are known to oxidize thioethers selectively to sulfoxides.

The above-described reactions, unless otherwise noted, are usually conducted at a pressure of about one to about three atmospheres, preferably at ambient pressure (about one atmosphere).

The present invention further embraces isolated compounds according to formula I. The expression "isolated compound" refers to a preparation of a compound of formula I, or a mixture of compounds according to formula I, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula I or a mixture of compounds according to formula I, which contains the named compound or mixture of compounds according to formula I in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC. The preferred method for purification of the compounds according to formula I or salts thereof comprises crystallizing the compound or salt from a solvent to form, preferably, a crystalline form of the compounds or salts thereof. Following crystallization, the crystallization solvent is removed by a process other than evaporation, for example filtration or decanting, and the crystals are then preferably washed using pure solvent (or a mixture of pure solvents). Preferred solvents for crystallization include water, alcohols, particularly alcohols containing up to four carbon atoms such as methanol, ethanol, isopropanol, and butan-1-ol, butan-2-ol, and 2-methyl-2-propanol, ethers, for example diethyl ether, diisopropyl ether, t-butyl methyl ether, 1,2-dimethoxyethane, tetrahydrofuran and 1,4-dioxane, carboxylic acids, for example formic acid and acetic acid, and hydrocarbon solvents, for example pentane, hexane, toluene, and mixtures thereof, particularly aqueous mixtures such as aqueous ethanol. Pure solvents, preferably at least analytical grade, and more preferably pharmaceutical grade are preferably used. In a preferred embodiment of the processes of the invention, the products are so isolated. In the compounds of the invention according to formula I or salt thereof, and pharmaceutical compositions thereof, the compound according to formula I or salt thereof is preferably in or prepared from a crystalline form, preferably prepared according to such a process.

The synthetic methods described above reflect a convergent synthesis strategy. Thus two components may be synthesized and elaborated separately prior to condensing or coupling the two components to form the target compounds. These convergent synthetic schemes allow for arrangement of the assembly steps of the backbone of the target compounds and derivatization of derivatizable functionalities to accommodate functional group sensitivity and/or to allow for functional groups or elements to be introduced either before or after the assembly of the backbone of the target compounds via the condensation or coupling reactions described.

It will be appreciated by one skilled in the art that certain aromatic substituents in the compounds of the invention, intermediates used in the processes described above, or precursors thereto, may be introduced by employing aromatic substitution reactions to introduce or replace a substituent, or by using functional group transformations to modify an existing substituent, or a combination thereof. Such reactions may be effected either prior to or immediately following the processes mentioned above, and are included as part of the process aspect of the invention. The reagents and reaction conditions for such procedures are known in the art. Specific examples of procedures which may be employed include, but are not limited to, electrophilic functionalization of an aromatic ring, for example via nitration, halogenation, or acylation; transformation of a nitro group to an amino group, for example via reduction, such as by catalytic hydrogenation; acylation, alkylation, or sulfonylation of an amino or hydroxyl group; replacement of an amino group by another functional group via conversion to an intermediate diazonium salt followed by nucleophilic or free radical substitution of the diazonium salt; or replacement of a halogen by another group, for example via nucleophilic or organometallically-catalyzed substitution reactions.

Additionally, in the aforesaid processes, certain functional groups which would be sensitive to the reaction conditions may be protected by protecting groups. A protecting group is a derivative of a chemical functional group which would otherwise be incompatible with the conditions required to perform a particular reaction which, after the reaction has been carried out, can be removed to re-generate the original functional group, which is thereby considered to have been "protected". Any chemical functionality that is a structural component of any of the reagents used to synthesize compounds of this invention may be optionally protected with a chemical protecting group if such a protecting group is useful in the synthesis of compounds of this invention. The person skilled in the art knows when protecting groups are indicated, how to select such groups, and processes that can be used for selectively introducing and selectively removing them, because methods of selecting and using protecting groups have been extensively documented in the chemical literature. Techniques for selecting, incorporating and removing chemical protecting groups may be found, for example, in *Protective Groups in Organic Synthesis* by Theodora W. Greene, Peter G. M. Wuts (John Wiley & Sons, Inc. 1999), the entire disclosure of which is incorporated herein by reference.

In addition to use of a protecting group, sensitive functional groups may be introduced as synthetic precursors to the functional group desired in the intermediate or final product. An example of this is an aromatic nitro ($—NO_2$) group. The aromatic nitro group goes not undergo any of the nucleophilic reactions of an aromatic amino group. However, the nitro group can serve as the equivalent of a protected amino group because it is readily reduced to the amino group under mild conditions that are selective for the nitro group over most other functional groups.

It will be appreciated by one skilled in the art that the processes described are not the exclusive means by which compounds of the invention may be synthesized and that an extremely broad repertoire of synthetic organic reactions is available to be potentially employed in synthesizing compounds of the invention. The person skilled in the art knows how to select and implement appropriate synthetic routes. Suitable synthetic methods may be identified by reference to the literature, including reference sources such as *Comprehensive Organic Synthesis*, Ed. B. M. Trost and I. Fleming (Pergamon Press, 1991), *Comprehensive Organic Functional Group Transformations*, Ed. A. R. Katritzky, O. Meth-Cohn, and C. W. Rees (Pergamon Press, 1996), *Comprehensive Organic Functional Group Transformations II*, Ed. A. R. Katritzky and R. J. K. Taylor (Editor) (Elsevier, 2$^{nd}$ Edition, 2004), *Comprehensive Heterocyclic Chemistry*, Ed. A. R. Katritzky and C. W. Rees (Pergamon Press, 1984), *Comprehensive Heterocyclic Chemistry II*, Ed. A. R. Katritzky, C. W. Rees, and E. F. V. Scriven (Pergamon Press, 1996), and *Advanced Organic Chemistry*, 4$^{th}$ Ed., J. March (John Wiley & Sons, 1992).

IV. ANTIBODY CONJUGATES

Another aspect of the invention relates to antibody conjugates of compounds of formula I of the formula I-L-Ab, or a salt thereof, wherein I is a compound of formula I; Ab is an antibody; and -L- is a single bond or a linking group covalently linking said compound of formula I to said antibody. In one embodiment, the invention relates to antibody conjugates of compounds of formula III of the formula III-L-Ab, or a salt thereof, wherein III is a compound of formula III; Ab is an antibody; and -L- is a single bond or a linking group covalently linking said compound of formula III to said antibody.

In a preferred sub-embodiment of the aforesaid conjugates of the formula I-L-Ab, or III-L-Ab, said antibody (Ab) is a monoclonal antibody or a monospecific polyclonal antibody.

In a more preferred sub-embodiment of the aforesaid conjugates of the formulae I-L-Ab, or III-L-Ab, the aforesaid antibody (Ab) is a tumor-specific antibody.

Antibodies, preferably monoclonal antibodies and monospecific polyclonal antibodies, and most preferably tumor-specific antibodies, may be covalently linked to compounds of the present invention. A "tumor-specific antibody" is an antibody which specifically binds to a tumor antigen, e.g., an antigen on a tumor cell.

The covalent linker between a compound of formula I and an antibody may, in its simplest form, comprise a single covalent bond connecting the compound of formula I to the antibody. More commonly the compound of formula I is attached to the antibody using a suitable bifunctional linking reagent. The term "bifunctional linking reagent" refers generally to a molecule that comprises two reactive moieties which are connected by a spacer element. The term "reactive moieties", in this context, refers to chemical functional groups capable of coupling with an antibody or a compound of formula I by reacting with functional groups on the antibody and the compound of formula I.

An example of a covalent bond formed as a linker between a compound of formula I and an antibody is a disulfide bond formed by the oxidation of an antibody and a compound of formula I, wherein a linking group is used that contains one or more cysteine amino acids. The cysteine residues can be oxidized to form disulfide links by dissolving 1 mg of the a suitable compound of formula I and 0.5 equivalents of the desired antibody in 1.5 ml of 0.1% (v/v) 17.5 mM acetic acid, pH 8.4, followed by flushing with nitrogen and then 0.01 M $K_2Fe(CN)_6$. After incubation for one hour at room temperature, the adduct peptide is purified by HPLC.

Another example of a suitable covalent bond formed as a linker between a compound of formula I and an antibody is an amide bond formed by reacting an amino group on a compound of the invention with a carboxylic acid group which forms part of the primary structure of the antibody (Ab) (such as, for example a glutamic or aspartic amino acid residue). Alternately, an amide bond could be formed if the reacting moieties were reversed, i.e., the compound of formula I could contain a carboxylic acid functionality and react with an amino functionality within the Ab structure.

Alternatively, a compound of formula I and an antibody Ab may be covalently linked using a bifunctional linking reagent.

For example, adducts can be prepared by first preparing S—(—N-hexylsuccinimido)-modified derivatives of an antibody and of a compound of formula I, according to the method of Cheronis et al., *J. Med. Chem.* 37: 348 (1994)(the entire disclosure of which is incorporated herein by reference). N-hexylmaleimide, a precursor for the modified antibody and compound of formula I, is prepared from N-(methoxycarbonyl)maleimide and N-hexylamine by mixing the two compounds in saturated $NaHCO_3$ at 0° C. according to the procedure of Bodanszky and Bodanszky, *The Practice of Peptide Synthesis*; Springer-Verlag, New York, pp. 29-31 (1984)(the entire disclosure of which is incorporated herein by reference). The product of the resulting reaction mixture is isolated by extraction into ethyl acetate, followed by washing with water, dried over $Na_2SO_4$, and is then concentrated in vacuo to produce N-hexylmaleimide as a light yellow oil. S—(N-Hexylsuccinimido)-modified antibody and formula I compound are then prepared from a cysteine-containing peptide and N-hexylmaleimide by mixing one part peptide with 1.5 parts N-hexylmaleimide in N,N-dimethylformamide (3.3 mL/mM peptide) followed by addition to 30 volumes of 0.1 M ammonium bicarbonate, pH 7.5. The S-alkylation reaction carried out in this manner is complete in 30 minutes. The resulting S—(N-hexylsuccinimido)-modified peptide monomer is purified by preparative reverse-phase HPLC, followed by lyophilization as a fluffy, white powder.

Bis-succinimidohexane peptide heterodimers (wherein one peptide is the antibody and the other peptide is attached to the formula I compound) may be prepared according to the method of Cheronis et al., supra from cysteine-substituted peptides. A mixture of one part bismaleimidohexane is made with two parts peptide monomer in N,N-dimethylformamide (3.3 mL/mM peptide) followed by addition to 0.1 ammonium bicarbonate, pH 7.5. The reaction mixture is stirred at room temperature and is usually completed within 30 minutes. The resulting bis-succinimidohexane peptide dimer is purified by preparative reverse-phase HPLC. After lyophilization the material is a fluffy, white powder.

Covalently linked adducts of the general formula I-L-Ab of the present invention may be prepared by utilizing homo-bifunctional linking reagents (wherein the two reactive moieties are the same), such as, for example, disuccinimidyl tartrate, disuccinimidyl suberate, ethylene glycolbis-(succinimidyl succinate), 1,5-difluoro-2,4-dinitrobenzene ("DFNB"), 4,4'-diisothiocyano-2,2'-disulfonic acid stilbene ("DIDS"), and bis-maleimidohexane ("BMH").

Alternatively, hetero-bifunctional linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxy-succinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl)aminobenzoate ("sulfo-SIAB"), sulfosuccinimidyl 4-(N-maleimidomethyl)cyclohexane-1-carboxylate ("sulfo-SMCC"), sulfosuccinimidyl 4-(p-maleimidophenyl)-butyrate ("sulfo-SMPB"), bromo acetyl-p-aminobenzoyl-N-hydroxy-succinimidyl ester, iodoacetyl-N-hydroxysuccinimidyl ester, and the like.

For hetero-bifunctional linking, a compound of formula I is derivatized with, for example, the N-hydroxysuccinimidyl portion of the bifunctional reagent, and the resulting derivatized compound is purified by chromatography. Next, a suitable tumor-specific Mab is reacted with the second functional group of the bifunctional linking reagent, assuring a directed sequence of binding between components of the desired adduct.

Typical hetero-bifunctional linking agents for forming protein-protein conjugates have an amino-reactive N-hydroxysuccinimide ester (NHS-ester) as one functional group and a sulfhydryl reactive group as the other functional group. First, epsilon-amino groups of surface lysine residues of either the Mab or the formula I compound are acylated with the NHS-ester group of the cross-linking agent. The remaining component, possessing free sulfhydryl groups, is reacted with the sulfhydryl reactive group of the cross-linking agent to form a covalently cross-linked dimer. Common thiol reactive groups include, for example, maleimides, pyridyl disulfides, and active halogens. For example, MBS contains a NHS-ester as the amino reactive group, and a maleimide moiety as the sulfhydryl reactive group.

Photoactive hetero-bifunctional linking reagents, e.g., photoreactive phenyl azides, may also be employed. One such reagent, SASD, may be linked to either a Mab or to a formula I compound wherein with an attached peptidyl group, via its NHS-ester group. The conjugation reaction is carried out at pH 7 at room temperature for about 10 minutes. Molar ratios between about 1 and about 20 of the cross-linking agent to the compounds to be linked may be used.

Numerous bifunctional linkers, useful as linkers (-L-), exist which have been used specifically for coupling small molecules to monoclonal antibodies, and many of these are commercially available. Examples include N-succinimidyl-3-(2-pyridyldithio)-propionate (SPDP), 2-iminothiolane (2-IT), 3-(4-carboxamidophenyl dithio)propionthioimidate (CDPT), N-succinimidyl-acetylthioacetate (SATA), ethyl-5-acetyl-propionthioimidate (AMPT) and N-succinimidyl-3-(4-carboxamidophenyldithio)propionate (SCDP). Procedures for preparation of immunoconjugates using these linkers is detailed in Cattel, et al, "Toxin-Targeted Design for Anticancer Therapy II: Preparation and Biological Comparison of Different Chemically Linked Gelonin-Antibody Conjugates", *J. Pharm. Sci.*, 1993, 82, 699-704, the entire disclosure of which is incorporated herein by reference.

V. TREATMENT OF CELLULAR PROLIFERATIVE DISORDERS USING COMPOUNDS OF THE INVENTION

According to another embodiment of the invention, a method of treating an individual suffering from a cellular proliferative disorder, particularly cancer, is provided, comprising administering to said individual an effective amount of at least one compound according to formula I, or a pharmaceutically acceptable salt thereof, either alone, or in combination with a pharmaceutically acceptable carrier.

According to another embodiment of the invention, a method of inducing apoptosis of cancer cells, preferably tumor cells, in an individual afflicted with cancer is provided, comprising administering to said individual an effective amount of at least one compound according to formula I, or a pharmaceutically acceptable salt thereof, either alone, or in combination with a pharmaceutically acceptable carrier.

According to another embodiment of the invention, a method of treating an individual suffering from a cellular proliferative disorder, particularly cancer, is provided, comprising administering to said individual an effective amount of at least one conjugate of the formula I-L-Ab, either alone, or in combination with a pharmaceutically acceptable carrier.

The invention is also directed to the use in medicine of a compound according to formula I, or a pharmaceutically acceptable salt thereof, or a conjugate according to formula I-L-Ab, or a pharmaceutically acceptable salt thereof.

The invention is also directed to the use of a compound according to formula I, or a pharmaceutically acceptable salt thereof, or a conjugate according to formula I-L-Ab, or a pharmaceutically acceptable salt thereof, in the preparation of a medicament for treatment of a cellular proliferative disorder, particularly cancer, or for inducing apoptosis of tumor cells in an individual affected with cancer.

Particular and preferred embodiments of this aspect of the invention are those wherein the compound of formula I used in the method of treatment, either alone or as part of a composition, or as a component of the antibody conjugate, is a particular or preferred embodiment of the compound of formula I in the description of the compounds and compositions of the invention as provided herein. In one preferred embodiment, a compound of formula I is a compound of formula III.

The compounds according to the invention may be administered to individuals (mammals, including animals and humans) afflicted with a cellular proliferative disorder such as cancer, malignant and benign tumors, blood vessel proliferative disorders, autoimmune disorders, and fibrotic disorders. In a particular embodiment of the invention, the individual treated is a human.

The compounds are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

The compounds are also believed useful in the treatment of non-cancer cellular proliferative disorders, that is, cellular proliferative disorders which are characterized by benign indications. Such disorders may also be known as "cytoproliferative" or "hyperproliferative" in that cells are made by the body at an atypically elevated rate. Non-cancer cellular proliferative disorders believed treatable by compounds according to the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X-linked lymphocellular proliferative disorder (Duncan disease), post-transplantation lymphocellular proliferative disorder (PTLD), macular degeneration, and retinopathies, such as diabetic retinopathies and proliferative vitreoretinopathy (PVR)

Other non-cancer cellular proliferative disorders believed treatable by compounds according to the invention include the presence of pre-cancerous lymphoproliferative cells associated with an elevated risk of progression to a cancerous disorder. Many non-cancerous lymphocellular proliferative disorders are associated with latent viral infections such as Epstein-Barr virus (EBV) and Hepatitis C. These disorders often begin as a benign pathology and progress into lymphoid neoplasia as a function of time.

Without wishing to be bound by any theory, at least one compound of the invention, 2-(1H-indol-5-ylamino)-6-(2,4-difluorophenylsulfonyl)-8-methylpyrido[2,3-d]pyrimidin-7(8H)-one, and salts thereof, is effective in inhibiting the activity of the kinase Plk2, and may exert its antiproliferative and apoptotic effects on tumor cells by inhibition of Plk2.

VI. SALTS OF COMPOUNDS ACCORDING TO THE INVENTION

The compounds of the present invention may take the form of salts. The term "salts" embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, trifluoromethanesulfonic, 2-hydroxyethanesulfonic, p-toluenesulfonic, sulfanilic, cyclohexylaminosulfonic, stearic, alginic, p-hydroxybutyric, salicylic, galactaric, pivalic and galacturonic acid. Examples of pharmaceutically unacceptable acid addition salts include, for example, perchlorates and tetrafluoroborates. In the present examples of compounds of formula I, compounds containing pyridine groups, or fused-ring pyridines, such as azaindoles, can be isolated as salts of inorganic acids or strong organic acids, e.g. hydrochloric acid or trifluoroacetic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine), tromethamine(tris(hydroxymethyl)aminomethane), and procaine. Examples of pharmaceutically unacceptable base addition salts include lithium salts and cyanate salts. Although pharmaceutically unacceptable salts are not generally useful as medicaments, such salts may be useful, for example, as intermediates in the synthesis of compounds of Formula I, for example in their purification by recrystallization.

All of these salts may be prepared by conventional means from the corresponding compound according to Formula I by reacting, for example, the appropriate acid or base with the compound according to Formula I. Preferably the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

VII. PHARMACEUTICAL COMPOSITIONS

The compounds of the invention may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a cellular proliferative disorder will, of course, be determined by the particular circumstances of the individual patient including the size, weight, age and sex of the patient, the nature and stage of the cellular proliferative disorder, the aggressiveness of the cellular proliferative disorder, and the route of administration of the compound.

For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

VIII. ROUTES OF ADMINISTRATION OF COMPOUNDS AND COMPOSITIONS OF THE INVENTION

The compounds may be administered by any route, including but not limited to oral, rectal, sublingual, buccal, ocular, pulmonary, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated within the scope of the invention is the instillation of a drug in the body of the patient in a controlled formulation, with systemic or local release of the drug to occur at a later time. For example, the drug may be localized in a depot for controlled release to the circulation, or for release to a local site of tumor growth.

One or more compounds useful in the practice of the present inventions may be administered simultaneously, by the same or different routes, or at different times during treatment. The compounds may be administered before, along with, or after other medications, including other anti-proliferative compounds.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about sixteen weeks. The treatment schedule may be repeated as required.

IX. ISOMERISM IN COMPOUNDS OF THE INVENTION

A. Geometrical Isomerism

The compounds of the invention may possess an olefinic double bond. The stereochemistry of compounds possessing an olefinic double bond is designated using the nomenclature using E and Z designations. The compounds are named according to the Cahn-Ingold-Prelog system, described in the IUPAC 1974 Recommendations, Section E: Stereochemistry, in *Nomenclature of Organic Chemistry*, John Wiley & Sons, Inc., New York, N.Y., 4$^{th}$ ed., 1992, pp. 127-38, the entire contents of which is incorporated herein by reference. Using this system of nomenclature, the four groups about a double bond are prioritized according to a series of rules wherein various functional groups are ranked. The isomer with the two higher ranking groups on the same side of the double bond is designated Z and the other isomer, in which the two higher ranking groups are on opposite sides of the double bond, is designated E. This is illustrated schematically in Scheme 7, where the Cahn-Ingold-Prelog system priority of the double bond substituents A is greater than that of B, and the priority of A' is greater than that of B'.

Scheme 7

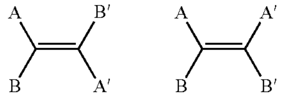

(E) isomer (Z) isomer

B. Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention which are biologically active in the treatment of cancer or other proliferative disease states.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 8, the Cahn-Ingold-Prelog ranking is A>B>C>D. The lowest ranking atom, D is oriented away from the viewer.

Scheme 8

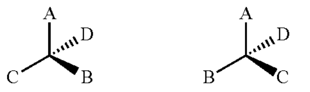

(R) configuration (S) configuration

Chiral centers in the compounds of the invention may occur, for example in the substituents attached to the aryl, heteroaryl, or heterocyclic groups $Ar^1$ and/or $R^2$. In addition, compounds wherein n is 1 (sulfoxides), are chiral, having two possible configurations at the sulfur atom, as shown in the example of Scheme 9.

Scheme 9

(S)-(I-b′)

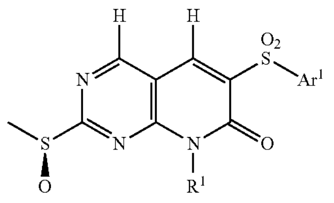

-continued (R)-(I-b′)

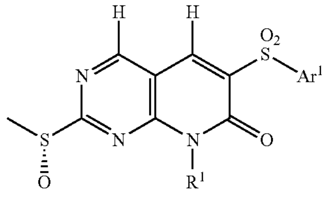

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization. For example, a compound of Formula I could possess two distinct sulfoxide groups which could provide, in theory, $2^2=4$ diastereomers, namely S,S-, S,R-, R,S-, and R,R-forms.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound having the structure of Formula I, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

C. Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (Scheme 10). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula I which are biologically active in the treatment of cancer or other proliferative disease states.

Scheme 10

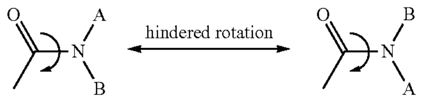

D. Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below (Scheme 11).

Scheme 11

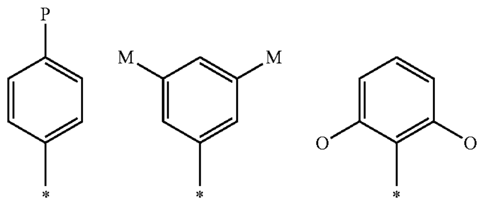

"para-" "meta-" "ortho-"

Another example of regioisomerism pertinent to the compounds of Formula II, a sub-embodiment of the compounds of Formula I. As discussed below in Scheme 12, benzimidazoles can exist in two isomeric forms (i.e., tautomers). Further derivatization of such benzimidazoles can produce regioisomers. For example, substitution of benzimidazoles by alkylation can provide two N-alkylated regioisomers, which can be separated to provide compounds of Formula I.

E. Tautomerism

Within the present invention it is to be understood that a compound of the formula I, or sub-embodiment compound of formula II, or sub-embodiment compound of formula III, or salts thereof, may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form which can be used to treat an individual suffering from a cellular proliferative disorder, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein.

By way of example, it is to be particularly understood that the compounds of Formula II wherein $R^B$ is hydrogen (i.e. II-a) may exist in tautomeric equilibrium with the form of the compounds wherein the $R^B$ hydrogen exchanges with the nitrogen at the position represented by $X^2$ in the generic Formula II represented above. The equilibrium is illustrated graphically below in Scheme 12. It is to be particularly understood that when $R^B$ is hydrogen, that although the specification and claims may read only upon the compounds of the Formula II-a ($R^B$=H), the compounds of Formula II-a' are also included within the scope of the invention, provided that all other bonded positions are held fixed.

Scheme 12

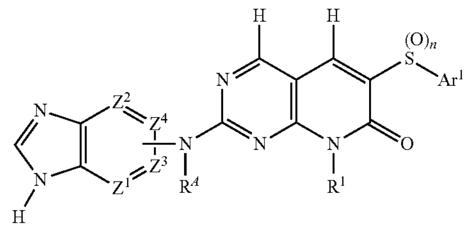

(II-a)

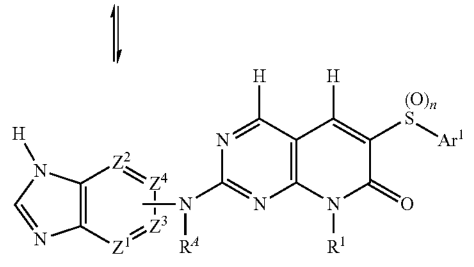

(II-a')

EXAMPLES

The following non-limiting examples are provided to illustrate the invention. The illustrated synthetic pathways are applicable to other embodiments of the invention. The synthetic procedures described as "general methods" describe what it is believed will be typically effective to perform the synthesis indicated. However, the person skilled in the art will appreciate that it may be necessary to vary the procedures for any given embodiment of the invention. For example, reaction monitoring, such as by using thin layer chromatography (TLC), or HPLC may be used to determine the optimum reaction time. Products may be purified by conventional techniques that will vary, for example, according to the amount of side products produced and the physical properties of the compounds. On a laboratory scale, recrystallization from a suitable solvent, column chromatography, normal or reverse phase HPLC, or distillation are all techniques which may be useful. The person skilled in the art will appreciate how to vary the reaction conditions to synthesize any given compound within the scope of the invention without undue experimentation. See, e.g., *Vogel's Textbook of Practical Organic Chemistry*, by A. I. Vogel, et al, *Experimental Organic Chemistry: Standard and Microscale*, by L. M. Harwood et al. ($2^{nd}$ Ed., Blackwell Scientific Publications, 1998), and *Advanced Practical Organic Chemistry*, by J. Leonard, et al. ($2^{nd}$ Edition, CRC Press 1994).

Synthetic Examples

The precursor compounds of Synthetic Examples 1-3 were prepared.

Synthetic Example 1 ethyl 4-(methylamino)-2-(methylsulfanyl)pyrimidine-5-carboxylate

4-Chloro-2-methylsulfanyl-pyrimidine-5-carboxylic acid ethyl ester (10 g, 429 mmol) was dissolved in acetonitrile to which DIPEA (4.34 g, 642 mmol) and methylamine hydrochloride (11.10 g, 858 mmol) was added. The reaction mixture was stirred at 100° C. for 3 hours, then cooled to room temperature and poured in to ice water. Off-white crystalline solid precipitated out. The solid was collected by filtration on a Buchner funnel and dried under vacuum to give the desired product (11 g). $^1$H NMR (DMSO-$d_6$): δ 1.30 (t, J=7 Hz, 3H), δ 2.46 (s, 3H), δ 2.99 (d, J=5 Hz, 3H), δ 4.29 (q, J=7 Hz, 2H), δ 8.09 (br, s, 1H), δ 8.53 (s, 1H).

Synthetic Example 2

(4-(methylamino)-2-(methylsulfanyl)pyrimidin-5-yl) methanol

Lithium aluminum hydride (3.86 g, 97.7 mmol) was suspended in THF under nitrogen atmosphere and cooled with dry ice. The compound of Synthetic Example 1 (9 g, 48.5 mmol) was dissolved in THF and added dropwise to the cooled LAH solution while keeping the reaction temperature below −20° C. The reaction was brought to room temperature and stirred overnight. After the completion of the reaction (monitored by TLC), the reaction mixture was quenched by the addition of water (5 ml), 15% NaOH (10 ml), and then water (15 ml) again. The precipitated white solid was filtered and the filtrate was evaporated under vacuum to give the desired product as a light yellow solid (6 g). $^1$H NMR (DMSO-$d_6$): δ 2.57 (s, 3H), δ 3.00 (d, 3H), δ 4.40 (s, 2H), δ 5.22 (m, 1H), δ 6.95 (br, s, 1H), δ 7.96 (s, 1H).

Synthetic Example 3

4-(methylamino)-2-(methylsulfanyl)pyrimidine-5-carboxaldehyde

The compound of Synthetic Example 2 (6 g, 32.3 mmol) was dissolved in chloroform to which $MnO_2$ (14.46 g, 166.3 mmol) was added. The reaction mixture was stirred overnight, an additional portion of $MnO_2$ (6.19 g, 71.2 mmol) was added, and stirring continued for 6 hours. The solids were removed by filtration through celite pad and washed thoroughly with chloroform. The chloroform was evaporated under vacuum to provide the desired product as a white crystalline solid (4.8 g). $^1$H NMR (DMSO-$d_6$): 2.50 (s, 3H), δ 3.12 (d, J=5 Hz, 3H), δ 8.47 (s, 1H), δ 8.60 (br, s, 1H), δ 9.72 (s, 1H).

Working Examples

Examples 1a-1h

Preparation of 6-aryl sulfonyl-8-methyl-2-methylsulfanylpyrido[2,3-d]pyrimidin-7(8H)-one compounds

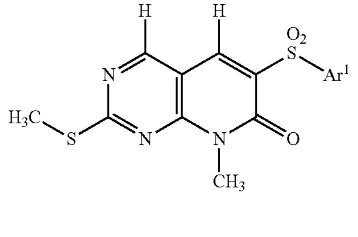

A mixture of the compound of Synthetic Example 3 (1 g, 7.2 mmol), 1.2 equivalents of a substituted or unsubstituted arylsulfonyl acetic acid ($Ar^1$—$SO_2CH_2CO_2H$), and a catalytic amount of benzylamine, was taken up in acetic acid (10 ml) and refluxed overnight. After the completion of the reaction (monitored by TLC), the reaction mixture was cooled to ambient temperature. The precipitated product was filtered and dried. Where appropriate the reaction mixture was diluted with hexane to precipitate the solid product. The solid was washed with saturated sodium bicarbonate, water, and dried under vacuum. The crude product was recrystallized in 2-propanol to give the compounds of Examples 1a-1i, as listed below, as pure products.

Example 1a $Ar^1$=phenyl: 8-methyl-2-(methylsulfanyl)-6-(phenylsulfonyl)pyrido[2,3-d]pyrimidin-7(8H)-one. $^1$H NMR (DMSO-$d_6$): δ 2.60 (s, 3H), δ 3.50 (s, 3H), 7.61-7.63 (m, 2H), 7.71-7.74 (m, 1H), S 8.00-8.02 (m, 2H), S 9.02 (s, 1H), S 9.19 (s, 1H).

Example 1b $Ar^1$=4-chlorophenyl: 6-(4-chlorophenylsulfonyl)-8-methyl-2-(methylsulfanyl)pyrido[2,3-d]pyrimidin-7(8H)-one. $^1$H NMR ($CDCl_3$): δ 2.57 (s, 3H), δ 3.60 (s, 3H), 7.25 (d, J=7.8 Hz, 2H), δ 8.00 (d, J=7.8 Hz, 2H), δ 8.64 (s, 1H), δ 8.73 (s, 1H).

Example 1c $Ar^1$=4-fluorophenyl: 6-(4-fluorophenylsulfonyl)-8-methyl-2-(methylsulfanyl)pyrido[2,3-d]pyrimidin-7(8H)-one. $^1$H NMR ($CDCl_3$): δ 2.54 (s, 3H), δ 3.61 (s, 3H), 7.32 (d, J=8.2 Hz, 2H), S 8.12 (d, J=8.2 Hz, 2H), δ 8.63 (s, 1H), δ 8.77 (s, 1H).

Example 1d $Ar^1$=4-methylphenyl: 8-methyl-2-(methylsulfanyl)-6-tosylpyrido[2,3-d]pyrimidin-7(8H)-one. $^1$H NMR (DMSO-$d_6$): δ 2.39 (s, 3H), δ 2.61 (s, 3H), δ 3.50 (s, 3H), 7.43 (d, J=8.4 Hz, 2H), δ 7.89 (d, J=8.4 Hz, 2H), δ 8.99 (s, 1H), δ 9.10 (s, 1H).

Example 1e $Ar^1$=4-bromophenyl: 6-(4-bromophenylsulfonyl)-8-methyl-2-(methylsulfanyl)pyrido[2,3-d]pyrimidin-7(8H)-one. $^1$H NMR (DMSO-$d_6$): δ 2.62 (s, 3H), δ 3.51 (s, 3H), 7.86 (d, J=8.0 Hz, 2H), δ 7.91 (d, J=8.0 Hz, 2H), δ 9.03 (s, 1H), δ 9.20 (s, 1H).

Example 1f $Ar^1$=4-carbomethoxyphenyl: methyl 4-(7,8-dihydro-8-methyl-2-(methylsulfanyl)-7-oxopyrido[2,3-d]pyrimidin-6-ylsulfonyl)benzoate. $^1$H NMR (DMSO-$d_6$): δ 2.41 (s, 3H), δ 3.30 (s, 3H), δ 3.71 (s, 3H), 7.94 (s, 4H), δ 8.86 (s, 1H), δ 9.01 (s, 1H).

Example 1g $Ar^1$=4-methoxyphenyl: 6-(4-methoxyphenylsulfonyl)-8-methyl-2-(methylsulfanyl)pyrido[2,3-d]pyrimidin-7(8H)-one. $^1$H NMR (DMSO-$d_6$): δ 2.60 (s, 3H), δ 3.51 (s, 3H), δ 3.84 (s, 3H), 7.14 (d, J=8.8 Hz, 2H), δ 7.94 (d, J=8.0 Hz, 2H), δ 8.96 (s, 1H), δ 9.17 (s, 1H).

Example 1h

Ar[1]=3-chloro-4-fluorophenyl: 6-(3-chloro-4-fluorophenylsulfonyl)-8-methyl-2-(methylsulfanyl)pyrido[2,3-d]pyrimidin-7(8H)-one. $^1H$ NMR (DMSO-$d_6$): δ 2.79 (s, 3H), δ 3.42 (s, 3H), 7.54-7.59 (m, 1H), δ 7.90-7.93 (m, 1H), δ 8.03-8.06 (m, 1H), δ 9.03 (s, 1H), δ 9.38 (s, 1H).

Examples 2a-2h

Preparation of 6-arylsulfonyl-8-methyl-2-methylsulfinylpyrido[2,3-d]pyrimidin-7(8H)-one compounds

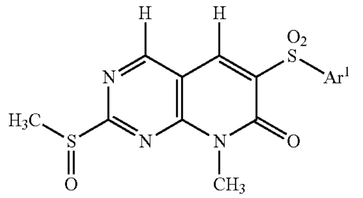

m-Chloroperoxybenzoic acid (5.25 mmol) was added to an ice cold solution of each of the compounds of Examples 1a-1h (3.5 mmol) in chloroform, and the reaction mixture was stirred at room temperature for 5 hours. After the completion of the reaction (monitored by TLC), the reaction mixture was washed with saturated sodium bicarbonate solution, brine, and dried with anhydrous $Na_2SO_4$. The organic layer was concentrated to give the compounds of Examples 2a-2h, respectively, as listed below, which were used for the next step without further purification.

Example 2a

Ar[1]=phenyl: 8-methyl-2-(methylsulfinyl)-6-(phenylsulfonyl)pyrido[2,3-d]pyrimidin-7(8H)-one.

Example 2b

Ar[1]=4-chlorophenyl: 6-(4-chlorophenylsulfonyl)-8-methyl-2-(methylsulfinyl)pyrido[2,3-d]pyrimidin-7(8H)-one.

Example 2c

Ar[1]=4-fluorophenyl: 6-(4-fluorophenylsulfonyl)-8-methyl-2-(methylsulfinyl)pyrido[2,3-d]pyrimidin-7(8H)-one.

Example 2d

Ar[1]=4-methylphenyl: 8-methyl-2-(methylsulfinyl)-6-tosylpyrido[2,3-d]pyrimidin-7(8H)-one.

Example 2e

Ar[1]=4-bromophenyl: 6-(4-bromophenylsulfonyl)-8-methyl-2-(methylsulfinyl)pyrido[2,3-d]pyrimidin-7(8H)-one.

Example 2f

Ar[1]=4-carbomethoxyphenyl: methyl 4-(7,8-dihydro-8-methyl-2-(methylsulfinyl)-7-oxopyrido[2,3-d]pyrimidin-6-ylsulfonyl)benzoate.

Example 2g

Ar[1]=4-methoxyphenyl: 6-(4-methoxyphenylsulfonyl)-8-methyl-2-(methylsulfinyl)pyrido[2,3-d]pyrimidin-7(8H)-one.

Example 2h

Ar[1]=3-chloro-4-fluorophenyl: 6-(3-chloro-4-fluorophenylsulfonyl)-8-methyl-2-(methylsulfinyl)pyrido[2,3-d]pyrimidin-7(8H)-one.

The following procedures were used to prepare compounds of Examples 3-68.

Example 3

2-(4-chlorophenylamino)-6-(4-chlorophenylsulfonyl)-8-methylpyrido[2,3-d]pyrimidin-7(8H)-one A mixture of 6-(4-chlorophenylsulfonyl)-8-methyl-2-(methylsulfinyl)pyrido[2,3-d]pyrimidin-7(8H)-one (1 eq) and 4-chloroaniline (1.5 eq) in toluene was refluxed overnight. After completion of the reaction (monitored by TLC) the reaction mixture was cooled to ambient temperature. The solid separated, was filtered, washed with hexane, and dried to afford the desired compound.

Example 4

6-(4-chlorophenylsulfonyl)-2-(4-methoxyphenylamino)-8-methylpyrido[2,3-d]pyrimidin-7(8H)-one The title compound was prepared according to the procedure of Example 3, substituting 4-methoxyaniline for 4-chloroaniline.

Example 5

6-(4-chlorophenylsulfonyl)-8-methyl-2-(quinolin-3-ylamino)pyrido[2,3-d]pyrimidin-7(8H)-one The title compound was prepared according to the procedure of Example 3, substituting 3-aminoquinoline for 4-chloroaniline.

Example 6

2-(1H-indol-5-ylamino)-6-(4-chlorophenylsulfonyl)-8-methylpyrido[2,3-d]pyrimidin-7(8H)-one The title compound was prepared according to the procedure of Example 3, substituting 5-aminindole for 4-chloroaniline.

Example 7

2-(3-morpholinopropylamino)-6-(4-chlorophenylsulfonyl)-8-methylpyrido[2,3-d]pyrimidin-7(8H)-one The title compound was prepared according to the procedure of Example 3, substituting 3-morpholinopropan-1-amine for 4-chloroaniline.

Example 8

6-(4-chlorophenylsulfonyl)-2-(4-acetylpiperazin-1-yl)-8-methylpyrido[2,3-d]pyrimidin-7(8H)-one The title compound was prepared according to the procedure of Example 3, substituting 4-acetylpiperazine for 4-chloroaniline.

Example 9

2-(2-(4-methylpiperazin-1-yl)ethylamino)-6-(4-chlorophenylsulfonyl)-8-methylpyrido[2,3-d]pyrimidin-7(8H)-one The title compound was prepared according to the procedure of Example 3, substituting 2-(4-methylpiperazin-1-yl)ethanamine for 4-chloroaniline.

Example 10

2-(1H-indol-4-ylamino)-6-(4-fluorophenylsulfonyl)-8-methylpyrido[2,3-d]pyrimidin-7(8H)-one The title compound was prepared according to the procedure of Example 3, substituting 6-(4-fluorophenyl sulfonyl)-8-methyl-2-(methyl sulfinyl)pyrido[2,3-d]pyrimidin-7(8H)-one for 6-(4-chlorophenyl sulfonyl)-8-methyl-2-(methyl sulfinyl)pyrido[2,3-d]pyrimidin-7(8H)-one, and substituting 4-aminoindole for 4-chloroaniline.

Example 11

2-1H-indol-5-ylamino)-6-(4-fluorophenylsulfonyl)-8-methylpyrido[2,3-d]pyrimidin-7(8H)-one The title compound was prepared according to the procedure of Example 3, substituting 6-(4-fluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 5-aminoindole for 4-chloroaniline.

Example 12

2-(1H-pyrrolo[2,3-b]pyridin-5-ylamino)-6-(4-fluorophenyl sulfonyl)-8-methylpyrido[2,3-d]pyrimidin-7(8H)-one The title compound was prepared according to the procedure of Example 3, substituting 6-(4-fluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 1H-pyrrolo[2,3-b]pyridin-5-amine for 4-chloroaniline.

Example 13

2-(1H-indazol-5-ylamino)-6-(4-fluorophenylsulfonyl)-8-methylpyrido[2,3-d]pyrimidin-7(8H)-one The title compound was prepared according to the procedure of Example 3, substituting 6-(4-fluorophenylsulfonyl)-8-methyl-2-(methyl sulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 1H-indazol-5-amine for 4-chloroaniline.

Example 14

8-methyl-2-(quinolin-8-ylamino)-6-tosylpyrido[2,3-d]pyrimidin-7(8H)-one

The title compound was prepared according to the procedure of Example 3, substituting 8-methyl-2-(methylsulfinyl)-6-tosylpyrido[2,3-d]pyrimidin-7(8H)-one for 6-(4-chlorophenyl sulfonyl)-8-methyl-2-(methyl sulfinyl)pyrido[2,3-d]pyrimidin-7(8H)-one, and substituting 8-aminoquinoline for 4-chloroaniline.

Example 15

8-methyl-2-(quinolin-6-ylamino)-6-tosylpyrido[2,3-]pyrimidin-7(8H)-one

The title compound was prepared according to the procedure of Example 3, substituting 8-methyl-2-(methylsulfinyl)-6-tosylpyrido[2,3-d]pyrimidin-7(8H)-one for 6-(4-chlorophenyl sulfonyl)-8-methyl-2-(methylsulfinyl)pyrido[2,3-d]pyrimidin-7(8H)-one, and substituting 6-aminoquinoline for 4-chloroaniline.

Example 16

2-(1H-indol-4-ylamino)-8-methyl-6-tosylpyrido[2,3-d]pyrimidin-7(8H)-one

The title compound was prepared according to the procedure of Example 3, substituting 8-methyl-2-(methylsulfinyl)-6-tosylpyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 4-aminoindole for 4-chloroaniline.

Example 17

2-(1H-indol-5-ylamino)-8-methyl-6-tosylpyrido[2,3-d]pyrimidin-7(8H)-one

The title compound was prepared according to the procedure of Example 3, substituting 8-methyl-2-(methylsulfinyl)-6-tosylpyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 5-aminoindole for 4-chloroaniline.

Example 18

2-(1H-indol-5-ylamino)-6-(4-bromophenylsulfonyl)-8-methylpyrido[2,3-d]pyrimidin-7(8H)-one The title compound was prepared according to the procedure of Example 3, substituting 6-(4-bromophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 5-aminoindole for 4-chloroaniline.

Example 19

2-(1H-pyrrolo[2,3-b]pyridin-5-ylamino)-8-methyl-6-tosylpyrido[2,3-d]pyrimidin-7(8H)-one The title compound was prepared according to the procedure of Example 3, substituting 8-methyl-2-(methylsulfinyl)-

6-tosylpyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 1H-pyrrolo[2,3-b]pyridin-5-amine for 4-chloroaniline.

Example 20

2-(4-methoxyphenylamino)-8-methyl-6-tosylpyrido[2,3-d]pyrimidin-7(8H)-one

The title compound was prepared according to the procedure of Example 3, substituting 8-methyl-2-(methylsulfinyl)-6-tosylpyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 4-methoxyaniline for 4-chloroaniline.

Example 21

2-(1H-indol-5-ylamino)-8-methyl-6-(phenylsulfonyl)pyrido[2,3-d]pyrimidin-7(8H)-one The title compound was prepared according to the procedure of Example 3, substituting 8-methyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 5-aminoindole for 4-chloroaniline.

Example 22

2-(1H-pyrrolo[2,3-b]pyridin-5-ylamino)-8-methyl-6-(phenylsulfonyl)pyrido[2,3-d]pyrimidin-7(8H)-one The title compound was prepared according to the procedure of Example 3, substituting 8-methyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 1H-pyrrolo[2,3-b]pyridin-5-amine for 4-chloroaniline.

Example 23

8-methyl-6-(phenylsulfonyl)-2-(quinolin-6-ylamino)pyrido[2,3-d]pyrimidin-7(8H)-one The title compound was prepared according to the procedure of Example 3, substituting 8-methyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 6-aminoquinoline for 4-chloroaniline.

Example 24

2-(1H-indol-6-ylamino)-6-(4-fluorophenylsulfonyl)-8-methylpyrido[2,3-d]pyrimidin-7(8H)-one The title compound was prepared according to the procedure of Example 3, substituting 6-(4-fluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 6-aminoindole for 4-chloroaniline.

Example 25

2-(1H-indol-6-ylamino)-8-methyl-6-(phenylsulfonyl)pyrido[2,3-d]pyrimidin-7(8H)-one The title compound was prepared according to the procedure of Example 3, substituting 8-methyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 6-aminoindole for 4-chloroaniline.

Example 26 methyl 4-(2-(1H-indol-5-ylamino)-7,8-dihydro-8-methyl-7-oxopyrido[2,3-d]pyrimidin-6-ylsulfonyl)benzoate The title compound was prepared according to the procedure of Example 3, substituting methyl 4-(7,8-dihydro-8-methyl-2-(methylsulfinyl)-7-oxopyrido[2,3-d]pyrimidin-6-ylsulfonyl)benzoate for 6-(4-chlorophenylsulfonyl)-8-methyl-2-(methylsulfinyl)pyrido[2,3-d]pyrimidin-7(8H)-one, and substituting 5-aminoindole for 4-chloroaniline.

Example 27

2-(2-oxoindolin-5-ylamino)-8-methyl-6-tosylpyrido[2,3-d]pyrimidin-7(8H)-one

The title compound was prepared according to the procedure of Example 3, substituting 8-methyl-2-(methylsulfinyl)-6-tosylpyrido[2,3-d]pyrimidin-7(8H)-one for 6-(4-chlorophenyl sulfonyl)-8-methyl-2-(methyl sulfinyl)pyrido[2,3-d]pyrimidin-7(8H)-one, and substituting 5-aminoindolin-2-one for 4-chloroaniline.

Example 28

2-(1H-indol-6-ylamino)-8-methyl-6-tosylpyrido[2,3-d]pyrimidin-7(8H)-one

The title compound was prepared according to the procedure of Example 3, substituting 8-methyl-2-(methylsulfinyl)-6-tosylpyrido[2,3-d]pyrimidin-7(8H)-one for 6-(4-chlorophenyl sulfonyl)-8-methyl-2-(methyl sulfinyl)pyrido[2,3-d]pyrimidin-7(8H)-one, and substituting 6-aminoindole for 4-chloroaniline.

Example 29

2-(1H-indol-5-ylamino)-6-(4-methoxyphenylsulfonyl)-8-methylpyrido[2,3-d]pyrimidin-7(8H)-one The title compound was prepared according to the procedure of Example 3, substituting 6-(4-methoxyphenylsulfonyl)-8-methyl-2-(methylsulfinyl)pyrido[2,3-d]pyrimidin-7(8H)-one for 6-(4-chlorophenylsulfonyl)-8-methyl-2-

(methylsulfinyl)pyrido[2,3-d]pyrimidin-7(8H)-one, and substituting 5-aminoindole for 4-chloroaniline.

Example 30

2-(1H-indol-4-ylamino)-6-(4-methoxyphenylsulfonyl)-8-methylpyrido[2,3-d]pyrimidin-7(8H)-one The title compound was prepared according to the procedure of Example 3, substituting 6-(4-methoxyphenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 4-aminoindole for 4-chloroaniline.

Example 31

2-(1H-indol-4-ylamino)-6-(4-chlorophenylsulfonyl)-8-methylpyrido[2,3-d]pyrimidin-7(8H)-one The title compound was prepared according to the procedure of Example 3, substituting 4-aminoindole for 4-chloroaniline.

Example 32

2-(1H-pyrrolo[2,3-b]pyridin-5-ylamino)-6-(4-chlorophenylsulfonyl)-8-methylpyrido[2,3-d]pyrimidin-7(8H)-one The title compound was prepared according to the procedure of Example 3, substituting 1H-pyrrolo[2,3-b]pyridin-5-amine for 4-chloroaniline.

Example 33

2-(1H-indol-5-ylamino)-6-(3-chloro-4-fluorophenylsulfonyl)-8-methylpyrido[2,3-d]pyrimidin-7(8H)-one The title compound was prepared according to the procedure of Example 3, substituting 6-(3-chloro-4-fluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 5-aminoindole for 4-chloroaniline.

Example 34

2-(1H-indol-4-ylamino)-6-(3-chloro-4-fluorophenylsulfonyl)-8-methylpyrido[2,3-d]pyrimidin-7(8H)-one The title compound was prepared according to the procedure of Example 3, substituting 6-(3-chloro-4-fluorophenylsulfonyl)-8-methyl-2-(methyl sulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 4-aminoindole for 4-chloroaniline.

Example 35

2-(1H-pyrrolo[2,3-b]pyridin-5-ylamino)-6-(3-chloro-4-fluorophenylsulfonyl)-8-methylpyrido[2,3-d]pyrimidin-7(8H)-one The title compound was prepared according to the procedure of Example 3, substituting 6-(3-chloro-4-fluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-c]pyrimidin-7(8H)-one, and substituting 1H-pyrrolo[2,3-b]pyridin-5-amine for 4-chloroaniline.

Example 36

2-(2-oxoindolin-5-ylamino)-6-(3-chloro-4-fluorophenylsulfonyl)-8-methylpyrido[2,3-d]pyrimidin-7(8H)-one The title compound was prepared according to the procedure of Example 3, substituting 6-(3-chloro-4-fluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 5-aminoindolin-2-one for 4-chloroaniline.

Example 37

4-(2-(1H-indol-5-ylamino)-7,8-dihydro-8-methyl-7-oxopyrido[2,3-d]pyrimidin-6-ylsulfonyl)benzoic acid 5% aqueous sodium hydroxide (10 ml) was added to an ice-cooled solution of Example 40 (0.3 g, 0.61 mmol) in methanol (20 ml) with stirring. After the addition the reaction mixture was slowly heated to 60° C. for 1 hour. After completion of the reaction (monitored by TLC), the reaction mixture was cooled to 0° C. and neutralized with dilute hydrochloric acid. The precipitated brown colored solid was filtered and dried under vacuum to give the title compound (0.12 g).

Example 38

2-(1H-indazol-5-ylamino)-6-(3-chloro-4-fluorophenylsulfonyl)-8-methylpyrido[2,3-d]pyrimidin-7(8H)-one The title compound was prepared according to the procedure of Example 3, substituting 6-(3-chloro-4-fluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 1H-indazol-5-amine for 4-chloroaniline.

Example 39

2-(1H-indol-5-ylamino)-6-(2,4-difluorophenylsulfonyl)-8-methylpyrido[2,3-d]pyrimidin-7(8H)-one step 39a. 6-(2,4-difluorophenylsulfonyl)-8-methyl-2-(methylsulfanyl)pyrido[2,3-d]pyrimidin-7(8H)-one was prepared according to the procedure of Example 1a, substituting 2,4-difluorophenylsulfonylacetic acid for phenylsulfonylacetic acid.

step 39b. 6-(2,4-difluorophenylsulfonyl)-8-methyl-2-(methylsulfinyl)pyrido[2,3-d]pyrimidin-7(8H)-one was prepared according to the procedure of Example 2a, substituting 6-(2,4-difluorophenylsulfonyl)-8-methyl-2-(methylsulfanyl)pyrido[2,3-d]pyrimidin-7(8H)-one for 8-methyl-2-(methylsulfanyl)-6-(phenylsulfonyl)pyrido[2,3-d]pyrimidin-7(8H)-one.

step 39c. The title compound was prepared according to the procedure of Example 3, substituting 6-(2,4-difluorophenylsulfonyl)-8-methyl-2-(methylsulfinyl)pyrido[2,3-d]pyrimidin-7(8H)-one for 6-(4-chlorophenylsulfonyl)-8-methyl-2-

(methylsulfinyl)pyrido[2,3-d]pyrimidin-7(8H)-one, and 5-aminoindole for 4-chloroaniline.

Example 40

2-(1H-indazol-5-ylamino)-6-(2,4-difluorophenylsulfonyl)-8-methylpyrido[2,3-d]pyrimidin-7(8H)-one The title compound was prepared according to the procedure of Example 3, substituting 6-(2,4-difluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 1H-indazol-5-amine for 4-chloroaniline.

Example 41

6-(2,4-difluorophenylsulfonyl)-2-(2-oxoindolin-5-ylamino)-8-methylpyrido[2,3-d]pyrimidin-7(8H)-one The title compound was prepared according to the procedure of Example 3, substituting 6-(2,4-difluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 5-aminoindolin-2-one for 4-chloroaniline.

Example 42

6-(2,4-difluorophenylsulfonyl)-2-(2-morpholinoethylamino)-8-methylpyrido[2,3-d]pyrimidin-7(8H)-one The title compound was prepared according to the procedure of Example 3, substituting 6-(2,4-difluorophenylsulfonyl)-8-methyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 2-morpholinoethylamine for 4-chloroaniline.

Example 43

2-(1H-indol-5-ylamino)-6-(4-hydroxyphenylsulfonyl)-8-methylpyrido[2,3-d]pyrimidin-7(8H)-one step 43a. 6-(4-hydroxyphenylsulfonyl)-8-methyl-2-(methylsulfanyl)pyrido[2,3-d]pyrimidin-7(8H)-one was prepared according to the procedure of Example 1a, substituting 4-hydroxyphenylsulfonylacetic acid for phenylsulfonylacetic acid.

step 43b. 6-(4-hydroxyphenylsulfonyl)-8-methyl-2-(methylsulfinyl)pyrido[2,3-d]pyrimidin-7(8H)-one was prepared according to the procedure of Example 2a, substituting 6-(4-hydroxyphenylsulfonyl)-8-methyl-2-(methylsulfanyl)pyrido[2,3-d]pyrimidin-7(8H)-one for 8-methyl-2-(methylsulfanyl)-6-(phenylsulfonyl)pyrido[2,3-d]pyrimidin-7(8H)-one.

step 43c. The title compound was prepared according to the procedure of Example 3, substituting 6-(4-hydroxyphenylsulfonyl)-8-methyl-2-(methylsulfinyl)pyrido[2,3-d]pyrimidin-7(8H)-one for 6-(4-chlorophenyl sulfonyl)-8-methyl-2-(methylsulfinyl)pyrido[2,3-d]pyrimidin-7(8H)-one, and 5-aminoindole for 4-chloroaniline.

Example 44

2-(1H-indol-6-ylamino)-6-(phenylsulfonyl)-8-propylpyrido[2,3-d]pyrimidin-7(8H)-one step 44a. 2-(methylsulfinyl)-6-(phenylsulfonyl)-8-propylpyrido[2,3-d]pyrimidin-7(8H)-one was prepared according to the procedure of Example 2a, substituting 2-(methylsulfanyl)-6-(phenylsulfonyl)-8-propylpyrido[2,3-d]pyrimidin-7(8H)-one for 8-methyl-2-(methylsulfanyl)-6-(phenylsulfonyl)pyrido[2,3-d]pyrimidin-7(8H)-one.

step 44b. The title compound was prepared according to the procedure of Example 3, substituting 2-(methylsulfinyl)-6-(phenylsulfonyl)-8-propylpyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and 6-aminoindole for 4-chloroaniline.

Example 45

2-(1H-indol-4-ylamino)-6-(phenylsulfonyl)-8-propylpyrido[2,3-d]pyrimidin-7(8H)-one The title compound was prepared according to the procedure of Example 3, substituting 2-(methylsulfinyl)-6-(phenylsulfonyl)-8-propylpyrido[2,3-d]pyrimidin-7(8H)-one (Example 44a) for 6-(4-chlorophenylsulfonyl)-8-methyl-2-(methylsulfinyl)pyrido[2,3-d]pyrimidin-7(8H)-one, and substituting 4-aminoindole for 4-chloroaniline.

Example 46

2-(1H-indol-5-ylamino)-6-(3-chloro-4-fluorophenylsulfonyl)pyrido[2,3-d]pyrimidin-7(8H)-one step 46a. 6-(3-chloro-4-fluorophenylsulfonyl)-2-(methylsulfanyl)pyrido[2,3-d]pyrimidin-7(8H)-one was prepared according to the procedure of Synthetic Examples 1-3, substituting ammonia for methylamine, and substituting the product obtained thereby in Example 1h.

step 46b. 6-(3-chloro-4-fluorophenylsulfonyl)-2-(methylsulfinyl)pyrido[2,3-d]pyrimidin-7(8H)-one was prepared according to the procedure of Example 2h, substituting 6-(3-chloro-4-fluorophenylsulfonyl)-2-(methylsulfanyl)pyrido[2,3-d]pyrimidin-7(8H)-one for 6-(3-chloro-4-fluorophenylsulfonyl)-8-methyl-2-(methylsulfanyl)pyrido[2,3-d]pyrimidin-7(8H)-one.

step 46c. The title compound was prepared according to the procedure of Example 3, substituting 6-(3-chloro-4-fluorophenylsulfonyl)-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and 5-aminoindole for 4-chloroaniline.

Example 47

2-(1H-indol-5-ylamino)-6-(phenylsulfonyl)-8-propylpyrido[2,3-d]pyrimidin-7(8H)-one The title compound was prepared according to the procedure of Example 3, substituting 2-(methylsulfinyl)-6-(phenylsulfonyl)-8-propylpyrido[2,3-d]pyrimidin-7(8H)-one (Example 44a) for 6-(4-chlorophenylsulfonyl)-8-methyl-2-(methylsulfinyl)pyrido[2,3-d]pyrimidin-7(8H)-one, and substituting 5-aminoindole for 4-chloroaniline.

Example 48

2-(methylsulfanyl)-6-(phenylsulfonyl)-8-propylpyrido[2,3-d]pyrimidin-7(8H)-one

The title compound was prepared according to the procedure of Synthetic Examples 1-3, substituting n-propylamine for methylamine, and substituting the product obtained thereby in Example 1a.

Example 50

2-(4-(4-methylpiperazin-1-yl)phenylamino)-6-(4-chlorophenylsulfonyl)-8-cyclohexylpyrido[2,3-d]pyrimidin-7(8H)-one step 50a. 6-(4-chlorophenylsulfonyl)-8-cyclohexyl-2-(methylsulfanyl)pyrido[2,3-d]pyrimidin-7(8H)-one was prepared according to the procedure of Synthetic Examples 1-3, substituting cyclohexylamine for methylamine, and substituting the product obtained thereby in Example 1b.

step 50b. 6-(4-chlorophenylsulfonyl)-8-cyclohexyl-2-(methylsulfinyl)pyrido[2,3-d]pyrimidin-7(8H)-one was prepared according to the procedure of Example 2b, substituting 6-(4-chlorophenylsulfonyl)-8-cyclohexyl-2-(methylsulfanyl)pyrido[2,3-d]pyrimidin-7(8H)-one for 6-(4-chlorophenylsulfonyl)-8-methyl-2-(methylsulfanyl)pyrido[2,3-d]pyrimidin-7(8H)-one.

step 50c. The title compound was prepared according to the procedure of Example 3, substituting 6-(4-chlorophenylsulfonyl)-8-cyclohexyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 4-(4-methylpiperazin-1-yl)aniline for 4-chloroaniline.

Example 51

2-(1H-indol-5-ylamino)-6-(4-chlorophenylsulfonyl)-8-cyclohexylpyrido[2,3-d]pyrimidin-7(8H)-one The title compound was prepared according to the procedure of Example 3, substituting 6-(4-chlorophenylsulfonyl)-8-cyclohexyl-2-(methylsulfinyl)pyrido[2,3-d]pyrimidin-7(8H)-one (Example 50b) for 6-(4-chlorophenylsulfonyl)-8-methyl-2-(methylsulfinyl)pyrido[2,3-d]pyrimidin-7(8H)-one, and substituting 5-aminoindole for 4-chloroaniline.

Example 52

6-(4-chlorophenylsulfonyl)-2-(4-morpholinophenylamino)-8-cyclohexylpyrido[2,3-d]pyrimidin-7(8H)-one The title compound was prepared according to the procedure of Example 3, substituting 6-(4-chlorophenyl sulfonyl)-8-cyclohexyl-2-(methylsulfinyl)pyrido[2,3-d]pyrimidin-7(8H)-one (Example 50b) for 6-(4-chlorophenylsulfonyl)-8-methyl-2-(methylsulfinyl)pyrido[2,3-d]pyrimidin-7(8H)-one, and substituting 4-morpholinoaniline for 4-chloroaniline.

Example 53

2-(1H-indol-4-ylamino)-6-(4-chlorophenylsulfonyl)-8-cyclohexylpyrido[2,3-d]pyrimidin-7(8H)-one The title compound was prepared according to the procedure of Example 3, substituting 6-(4-chlorophenylsulfonyl)-8-cyclohexyl-2-(methylsulfinyl)pyrido[2,3-d]pyrimidin-7(8H)-one (Example 50b) for 6-(4-chlorophenylsulfonyl)-8-methyl-2-(methylsulfinyl)pyrido[2,3-d]pyrimidin-7(8H)-one, and substituting 4-aminoindole for 4-chloroaniline.

Example 54

2-(1H-indol-5-ylamino)-8-ethyl-6-(phenylsulfonyl)pyrido[2,3-d]pyrimidin-7(8H)-one step 54a. 8-ethyl-2-(methylsulfanyl)-6-(phenylsulfonyl)pyrido[2,3-d]pyrimidin-7(8H)-one was prepared according to the procedure of Synthetic Examples 1-3, substituting ethylamine for methylamine, and substituting the product obtained thereby in Example 1a.

step 54b. 8-ethyl-2-(methylsulfinyl)-6-(phenylsulfonyl)pyrido[2,3-d]pyrimidin-7(8H)-one was prepared according to the procedure of Example 2a, substituting 8-ethyl-2-(methylsulfanyl)-6-(phenylsulfonyl)pyrido[2,3-d]pyrimidin-7(8H)-one for 8-methyl-2-(methylsulfanyl)-6-(phenylsulfonyl)pyrido[2,3-d]pyrimidin-7(8H)-one.

step 54c. The title compound was prepared according to the procedure of Example 3, substituting 8-ethyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and 5-aminoindole for 4-chloroaniline.

Example 55

2-(1H-indol-5-ylamino)-8-cyclopentyl-6-(phenylsulfonyl)pyrido[2,3-d]pyrimidin-7(8H)-one The title compound was prepared according to the procedure of Example 3, substituting 8-cyclopentyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 5-aminoindole for 4-chloroaniline.

Example 56

2-(4-methoxyphenylamino)-8-cyclopentyl-6-(phenylsulfonyl)pyrido[2,3-d]pyrimidin-7(8H)-one The title compound was prepared according to the procedure of Example 3, substituting 8-cyclopentyl-2-(methylsulfinyl)-6-(phenyl sulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 4-methoxyaniline for 4-chloroaniline.

Example 57

8-cyclopentyl-2-(4-(5-(trifluoromethyl)pyridin-2-yl)piperazin-1-yl)-6-(phenylsulfonyl)pyrido[2,3-d]pyrimidin-7(8H)-one The title compound was prepared according to the procedure of Example 3, substituting 8-cyclopentyl-2-(methylsulfinyl)-6-(phenylsulfonyl)pyrido[2,3-a]pyrimidin-7(8H)-one for 6-(4-chlorophenylsulfonyl)-8-methyl-2-(methylsulfinyl)pyrido[2,3-d]pyrimidin-7(8H)-one, and substituting 1-(5-(trifluoromethyl)pyridin-2-yl)piperazine for 4-chloroaniline.

Example 58

2-(4-(4-methylpiperazin-1-yl)phenylamine)-6-(4-chlorophenylsulfonyl)-8-cyclopentylpyrido[2,3-d]pyrimidin-7(8H)-one The title compound was prepared according to the procedure of Example 3, substituting 6-(4-chlorophenylsulfonyl)-8-cyclopentyl-2-(methylsulfinyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 4-(4-methylpiperazin-1-yl)aniline for 4-chloroaniline.

Example 59

6-(4-chlorophenylsulfonyl)-8-cyclopentyl-2-(methylsulfinyl)pyrido[2,3-d]pyrimidin-7(8H)-one The title compound was prepared according to the procedure of Example 2b, substituting 6-(4-chlorophenylsulfonyl)-8-cyclopentyl-2-(methylsulfanyl)pyrido[2,3-d]pyrimidin-7(8H)-one for 6-(4-chlorophenylsulfonyl)-8-methyl-2-(methylsulfanyl)pyrido[2,3-d]pyrimidin-7(8H)-one.

Example 60

6-(4-chlorophenylsulfonyl)-8-cyclopentyl-2-(methylsulfanyl)pyrido[2,3-d]pyrimidin-7(8H)-one The title compound was prepared according to the procedure of Synthetic Examples 1-3, substituting cyclopentylamine for methylamine, and substituting the product obtained thereby in Example 1b.

Example 61

8-cyclopentyl-2-(cyclopentylamino)-6-(phenylsulfonyl)pyrido[2,3-d]pyrimidin-7(8H)-one The title compound was prepared according to the procedure of Example 3, substituting 8-cyclopentyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting cyclopentylamine for 4-chloroaniline.

Example 62

2-(3,4,5-trimethoxyphenylamino)-8-cyclopentyl-6-(phenylsulfonyl)pyrido[2,3-d]pyrimidin-7(8H)-one The title compound was prepared according to the procedure of Example 3, substituting 8-cyclopentyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 3,4,5-trimethoxyaniline for 4-chloroaniline.

Example 63

2-(4-morpholinophenylamino)-8-cyclopentyl-6-(phenylsulfonyl)pyrido[2,3-d]pyrimidin-7(8H)-one The title compound was prepared according to the procedure of Example 3, substituting 8-cyclopentyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 4-morpholinoaniline for 4-chloroaniline.

Example 64

2-(4-(4-methylpiperazin-1-yl)phenylamino)-8-cyclopentyl-6-(phenylsulfonyl)pyrido[2,3-d]pyrimidin-7(8H)-one The title compound was prepared according to the procedure of Example 3, substituting 8-cyclopentyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 4-(4-methylpiperazin-1-yl)aniline for 4-chloroaniline.

Example 65

2-(5-(4-tert-butoxycarbonylpiperazin-1-yl)pyridin-2-ylamino)-8-cyclopentyl-6-(phenylsulfonyl)pyrido[2,3-d]pyrimidin-7(8H)-one The title compound was prepared according to the procedure of Example 3, substituting 8-cyclopentyl-2-(methylsulfinyl)-6-(phenylsulfonyl)pyrido[2,3-d]pyrimidin-7(8H)-one for 6-(4-chlorophenylsulfonyl)-8-methyl-2-(methylsulfinyl)pyrido[2,3-d]pyrimidin-7(8H)-one, and substituting 5-(4-(t-BOC)-piperazin-1-yl)pyridin-2-amine for 4-chloroaniline.

Example 66

8-cyclopentyl-2-(methylsulfinyl)-6-(phenylsulfonyl)pyrido[2,3-d]pyrimidin-7(8H)-one The title compound was prepared according to the procedure of Example 2a, substituting 8-cyclopentyl-2-(methylsulfanyl)-6-(phenylsulfonyl)pyrido[2,3-d]pyrimidin-7(8H)-one for 8-methyl-2-(methylsulfanyl)-6-(phenylsulfonyl)pyrido[2,3-d]pyrimidin-7(8H)-one.

Example 67

8-cyclopentyl-2-(methylsulfanyl)-6-(phenylsulfonyl)pyrido[2,3-d]pyrimidin-7(8H)-one The title compound was prepared according to the procedure of Synthetic Examples 1-3, substituting cyclopentylamine for methylamine, and substituting the product obtained thereby in Example 1a.

Example 68

2-(methylsulfanyl)-6-(phenylsulfonyl)pyrido[2,3-d]pyrimidin-7(8H)-one

The title compound was prepared according to the procedure of Synthetic Examples 1-3, substituting ammonia for methylamine, and substituting the product obtained thereby in Example 1a.

The compounds of Examples 3-68, along with their structural formulae and representative characterization data, are listed in Table 1 below.

TABLE 1

Compound Examples

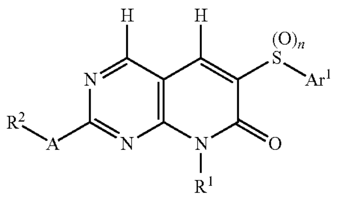

| Example | Structure | Name | Characterization Data |
|---|---|---|---|
| 3 | 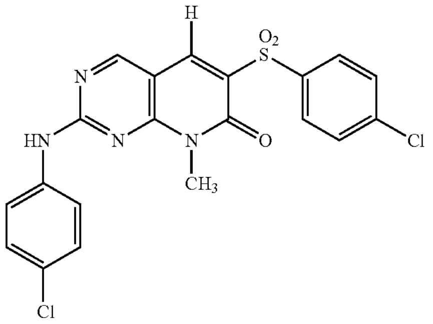 [SMILES: Cn1c(=O)c(S(=O)(=O)c2ccc(Cl)cc2)cc2cnc(Nc3ccc(Cl)cc3)nc21] | 2-(4-chlorophenylamino)-6-(4-chlorophenylsulfonyl)-8-methylpyrido[2,3-d]pyrimidin-7(8H)-one | m.p. >300° C.; $^1$H-NMR (DMSO-$d_6$) δ 3.48 (s, 3H), 7.41 (d, J = 8.8 Hz, 2H), 7.70 (d, J = 8.4 Hz, 2H), 7.82 (d, J = 8.4 Hz, 2H), 7.99 (d, J = 8.8 Hz, 2H), 8.88 (s, 1H), 9.10 (s, 1H), 10.40 (s, 1H). |
| 4 | 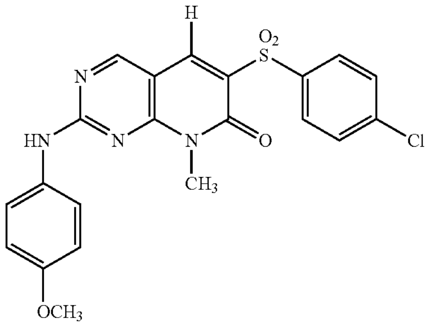 [SMILES: COc1ccc(Nc2ncc3cc(S(=O)(=O)c4ccc(Cl)cc4)c(=O)n(C)c3n2)cc1] | 6-(4-chlorophenylsulfonyl)-2-(4-methoxyphenylamino)-8-methylpyrido[2,3-d]pyrimidin-7(8H)-one | m.p. 286-290° C.; $^1$H-NMR (DMSO-$d_6$) δ 3.64 (s, 3H), 3.75 (s, 3H), 6.90 (d, J = 9.0 Hz, 2H), 7.50 (d, J = 8.0 Hz, 2H), 7.60 (d, J = 8.0 Hz, 2H), 7.72 (d, J = 8.8 Hz, 2H), 7.99 (s, 1H), 8.10 (s, 1H), 10.20 (s, 1H). |
| 5 | 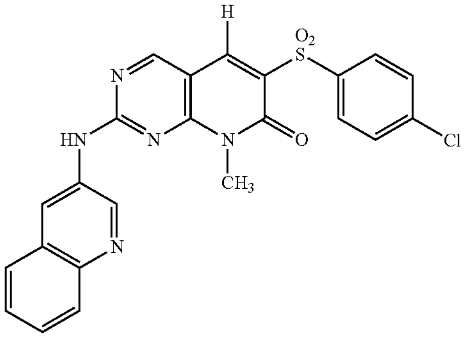 [SMILES: Cn1c(=O)c(S(=O)(=O)c2ccc(Cl)cc2)cc2cnc(Nc3cnc4ccccc4c3)nc21] | 6-(4-chlorophenylsulfonyl)-8-methyl-2-(quinolin-3-ylamino)pyrido[2,3-d]pyrimidin-7(8H)-one | m.p. 304-306° C.; $^1$H-NMR (DMSO-$d_6$) δ 3.40 (s, 3H), 7.12 (s, 1H), 7.42 (s, 1H), 7.51 (m, 1H), 7.55 (m, 1H), 7.62 (d, J = 8.0 Hz, 2H), 7.80 (d, J = 8.0 Hz, 2H), 7.83 (s, 1H), 7.86 (s, 1H), 8.25 (s, 2H), 10.38 (s, 1H). |
| 6 | 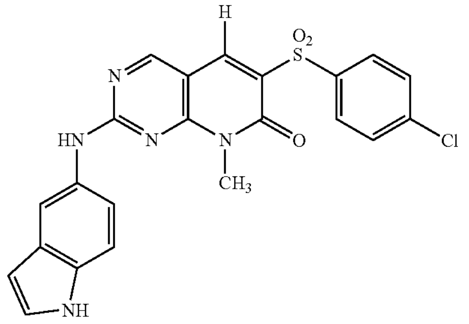 [SMILES: Cn1c(=O)c(S(=O)(=O)c2ccc(Cl)cc2)cc2cnc(Nc3ccc4[nH]ccc4c3)nc21] | 2-(1H-indol-5-ylamino)-6-(4-chlorophenylsulfonyl)-8-methylpyrido[2,3-d]pyrimidin-7(8H)-one | m.p. 316-320° C.; $^1$H-NMR (DMSO-$d_6$) δ 3.40 (s, 3H), 6.40-6.43 (m, 1H), 7.29-7.30 (m, 3H), 7.36-7.37 (m, 2H), 8.01-8.18 (m, 3H), 8.80 (s, 1H), 9.03 (s, 1H), 10.30 (s, 1H), 11.07 (s, 1H). |

TABLE 1-continued

Compound Examples

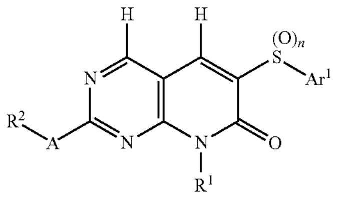

| Example | Structure | Name | Characterization Data |
|---|---|---|---|
| 7 | 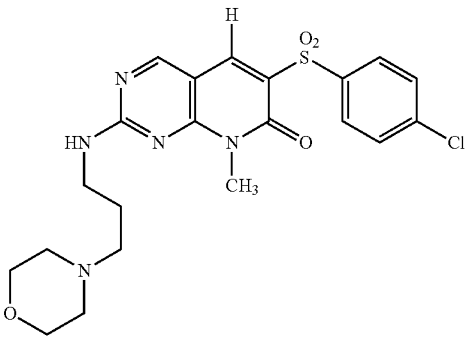 [SMILES: Cn1c(=O)c(S(=O)(=O)c2ccc(Cl)cc2)cc2cnc(NCCCN3CCOCC3)nc21] | 2-(3-morpholinopropylamino)-6-(4-chlorophenylsulfonyl)-8-methylpyrido[2,3-d]pyrimidin-7(8H)-one | m.p. 160-164° C.; $^1$H-NMR (DMSO-$d_6$) δ 1.70-1.73 (m, 2H), 2.30-2.32 (m, 6H), 3.41 (s, 2H), 3.46 (s, 3H), 3.53-3.55 (m, 4H), 7.67 (d, J = 8.4 Hz, 2H), 7.97 (d, J = 8.4 Hz, 2H), 8.74 (s, 1H), 8.88 (s, 1H), 8.96 (s, 1H). |
| 8 | 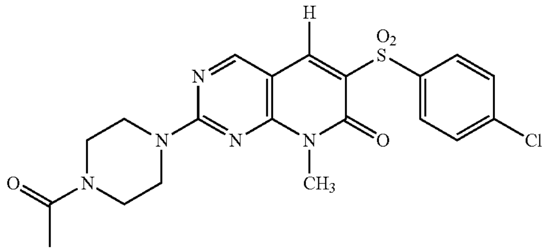 [SMILES: CC(=O)N1CCN(c2ncc3cc(S(=O)(=O)c4ccc(Cl)cc4)c(=O)n(C)c3n2)CC1] | 6-(4-chlorophenylsulfonyl)-2-(4-acetylpiperazin-1-yl)-8-methylpyrido[2,3-d]pyrimidin-7(8H)-one | m.p. 264-268° C.; $^1$H-NMR (DMSO-$d_6$) δ 2.01 (s, 3H), 3.42 (s, 3H), 3.50-3.56 (m, 4H), 3.90-3.94 (m, 4H), 7.69 (d, J = 8.2 Hz, 2H), 7.98 (d, J = 8.2 Hz, 2H), 8.80 (s, H), 9.00 (s, 1H). |
| 9 | 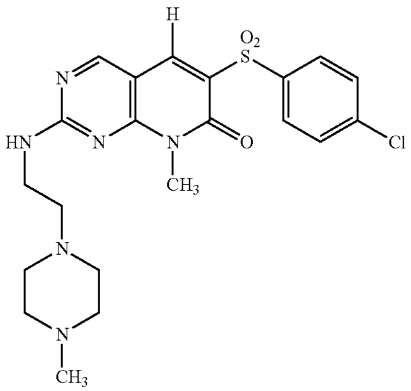 [SMILES: CN1CCN(CCNc2ncc3cc(S(=O)(=O)c4ccc(Cl)cc4)c(=O)n(C)c3n2)CC1] | 2-(2-(4-methylpiperazin-1-yl)ethylamino)-6-(4-chlorophenylsulfonyl)-8-methylpyrido[2,3-d]pyrimidin-7(8H)-one | m.p. 176-180° C.; $^1$H-NMR (DMSO-$d_6$) δ 2.23 (s, 3H), 2.31-2.37 (m, 4H), 2.37-2.38 (m, 4H), 3.41 (s, 3H), 3.44-3.49 (m, 4H), 7.67 (d, J = 7.2 Hz, 2H), 7.97 (d, J = 7.6 Hz, 2H), 8.74 (s, 1H), 8.88 (s, 1H), 8.96 (S, 1H). |
| 10 | 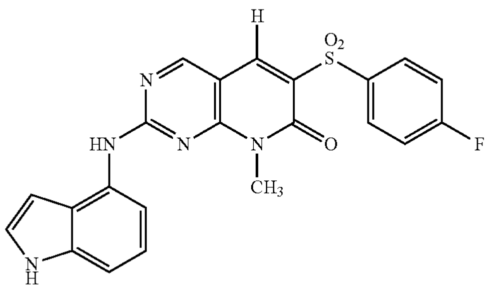 [SMILES: Cn1c(=O)c(S(=O)(=O)c2ccc(F)cc2)cc2cnc(Nc3cccc4[nH]ccc34)nc21] | 2-(1H-indol-4-ylamino)-6-(4-fluorophenylsulfonyl)-8-methylpyrido[2,3-d]pyrimidin-7(8H)-one | m.p. >350° C.; $^1$H-NMR (DMSO-$d_6$) 3.39 (s, 3H), 6.61-6.65 (m, 1H), 7.08-7.14 (m, 3H), 7.41-7.56 (m, 3H), 8.04-8.08 (m, 2H), 8.80 (s, 1H), 9.07 (s, 1H), 10.35 (s, 1H), 11.16 (s, 1H). |

TABLE 1-continued

Compound Examples

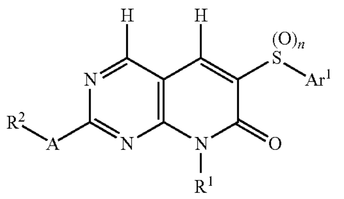

| Example | Structure | Name | Characterization Data |
|---|---|---|---|
| 11 | 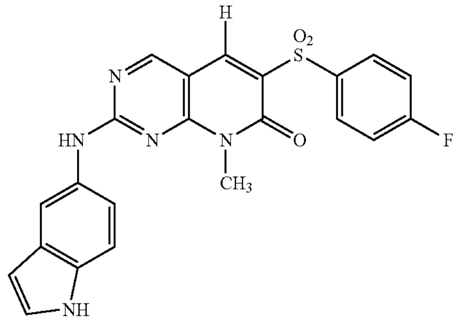 [SMILES: Cn1c(=O)c(S(=O)(=O)c2ccc(F)cc2)cc2cnc(Nc3ccc4[nH]ccc4c3)nc21] | 2-(1H-indol-5-ylamino)-6-(4-fluorophenylsulfonyl)-8-methylpyrido[2,3-d]pyrimidin-7(8H)-one | m.p. 278-282° C.; $^1$H-NMR (DMSO-$d_6$) δ 3.58 (s, 3H), 6.51 (s, 1H), 7.42-7.47 (m, 3H), 7.53-7.57 (m, 2H), 8.15-8.19 (m, 3H), 8.90 (s, 1H), 9.10 (s, 1H), 10.50 (s, 1H), 11.10 (s, 1H). |
| 12 | 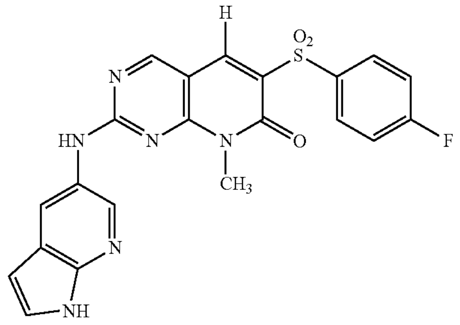 [SMILES: Cn1c(=O)c(S(=O)(=O)c2ccc(F)cc2)cc2cnc(Nc3cnc4[nH]ccc4c3)nc21] | 2-(1H-pyrrolo[2,3-b]pyridin-5-ylamino)-6-(4-fluorophenylsulfonyl)-8-methylpyrido[2,3-d]pyrimidin-7(8H)-one | m.p. 274-280° C.; $^1$H-NMR (DMSO-$d_6$) δ 3.34 (s, 3H), 6.44-6.50 (m, 1H), 7.44-7.49 (m, 4H), 8.02-8.09 (m, 3H), 8.84 (s, 1H), 9.07 (s, 1H), 10.70 (s, 1H), 11.50 (s, 1H). |
| 13 | 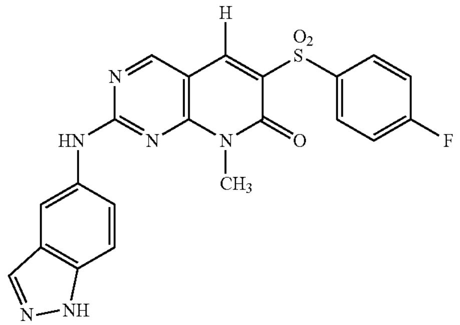 [SMILES: Cn1c(=O)c(S(=O)(=O)c2ccc(F)cc2)cc2cnc(Nc3ccc4[nH]ncc4c3)nc21] | 2-(1H-indazol-5-ylamino)-6-(4-fluorophenylsulfonyl)-8-methylpyrido[2,3-d]pyrimidin-7(8H)-one | m.p. 160-165° C.; $^1$H-NMR (DMSO-$d_6$) δ 3.35 (s, 3H), 7.31-7.35 (m, 4H), 7.91-7.94 (m, 4H), 8.69 (s, 1H), 8.92 (s, 1H), 10.30 (s, 1H), 12.50 (s, 1H). |
| 14 | 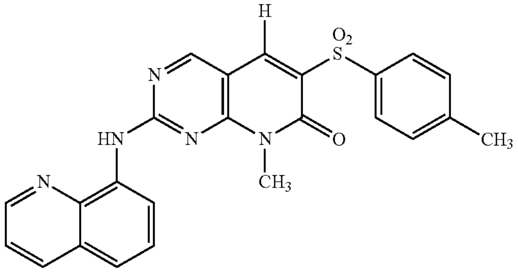 [SMILES: Cc1ccc(S(=O)(=O)c2cc3cnc(Nc4cccc5cccnc45)nc3n(C)c2=O)cc1] | 8-methyl-2-(quinolin-8-ylamino)-6-tosylpyrido[2,3-d]pyrimidin-7(8H)-one | m.p. >350° C.; $^1$H-NMR (DMSO-$d_6$) δ 2.22 (s, 3H), 3.50 (s, 3H), 7.40-7.43 (m, 4H), 7.55-7.56 (m, 2H), 7.74 (d, J = 8.0 Hz, 2H), 8.25-8.32 (m, 2H), 8.68 (s, 1H), 8.82 (s, 1H), 10.20 (s, 1H). |

TABLE 1-continued

Compound Examples

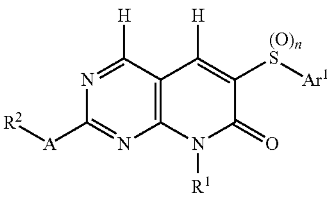

| Example | Structure | Name | Characterization Data |
| --- | --- | --- | --- |
| 15 | 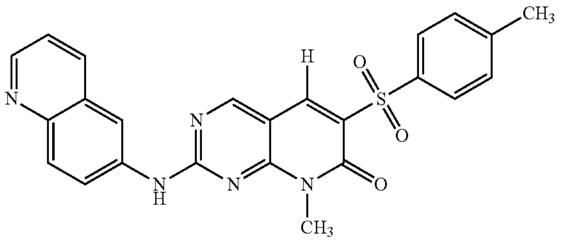 [SMILES: Cc1ccc(S(=O)(=O)c2cc3cnc(Nc4ccc5ncccc5c4)nc3n(C)c2=O)cc1] | 8-methyl-2-(quinolin-6-ylamino)-6-tosylpyrido[2,3-d]pyrimidin-7(8H)-one | m.p. 325-330° C.; $^1$H-NMR (DMSO-$d_6$) δ 2.34 (s, 3H), 3.40 (s, 3H), 6.80 (s, 1H), 7.42-7.43 (m, 3H), 7.48-7.49 (m, 1H), 7.75 (d, J = 8.2 Hz, 2H), 7.82-7.83 (m ,1H), 8-15-8.25 (m, 2H), 8.60-8.81 (m, 2H), 10.60 (s, 1H). |
| 16 | 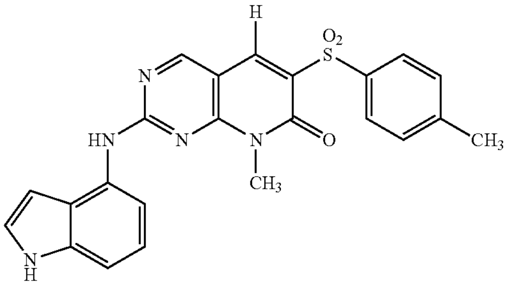 [SMILES: Cc1ccc(S(=O)(=O)c2cc3cnc(Nc4cccc5[nH]ccc45)nc3n(C)c2=O)cc1] | 2-(1H-indol-4-ylamino)-8-methyl-6-tosylpyrido[2,3-d]pyrimidin-7(8H)-one | m.p. 295-300° C.; $^1$H-NMR (DMSO-$d_6$) δ 2.38 (s, 3H), 3.53 (s, 3H), 6.47 (s, 1H), 7.39-7.54 (m, 5H), 7.94 (d, J = 8 Hz, 2H), 8.09 (s, 1H), 8.85 (s, 1H), 9.08 (s, 1H), 10.54 (s, 1H), 11.13 (s, 1H). |
| 17 | 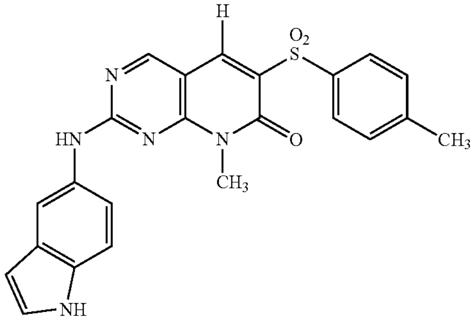 [SMILES: Cc1ccc(S(=O)(=O)c2cc3cnc(Nc4ccc5[nH]ccc5c4)nc3n(C)c2=O)cc1] | 2-(1H-indol-5-ylamino)-8-methyl-6-tosylpyrido[2,3-d]pyrimidin-7(8H)-one | m.p. 310-314° C.; $^1$H-NMR (DMSO-$d_6$) δ 2.39 (s, 3H), 3.42 (s, 3H), 6.67-6.69 (m, 1H), 7.12-7.42 (m, 5H), 7.70 (s, 1H), 7.90 (d, J = 7.2 Hz, 1H), 8.84 (s, 1H), 9.07 (s, 1H), 10.36 (s, 1H), 11.18 (s, 1H). |
| 18 | 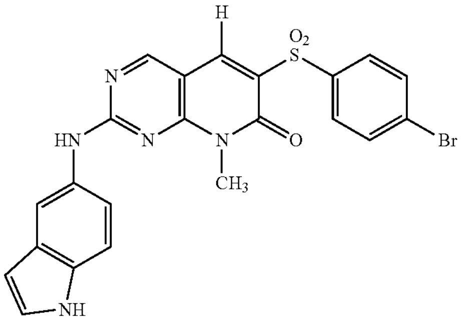 [SMILES: Cn1c(=O)c(S(=O)(=O)c2ccc(Br)cc2)cc2cnc(Nc3ccc4[nH]ccc4c3)nc21] | 2-(1H-indol-5-ylamino)-6-(4-bromophenylsulfonyl)-8-methylpyrido[2,3-d]pyrimidin-7(8H)-one | m.p. 316-320° C.; $^1$H-NMR (DMSO-$d_6$) δ 3.53 (s, 3H), 6.47 (s, 1H), 7.38-7.52 (m, 3H), 7.88 (d, J = 8.8 Hz, 2H), 7.98 (d, J = 8.8 Hz, 2H), 8.08 (s, 1H), 8.87 (s, 1H), 9.09 (s, 1H), 10.58 (s, 1H), 11.14 (s, 1H). |

TABLE 1-continued

Compound Examples

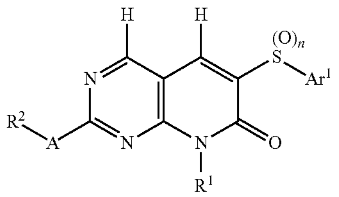

| Example | Structure | Name | Characterization Data |
|---|---|---|---|
| 19 | 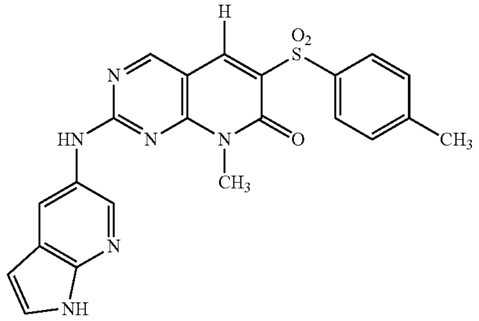 [SMILES: Cc1ccc(S(=O)(=O)c2cc3cnc(Nc4cnc5[nH]ccc5c4)nc3n(C)c2=O)cc1] | 2-(1H-pyrrolo[2,3-b]pyridin-5-ylamino)-8-methyl-6-tosylpyrido[2,3-d]pyrimidin-7(8H)-one | m.p. 252-255° C.; $^1$H-NMR (DMSO-$d_6$) δ 2.43 (s, 3H), 3.46 (s, 3H), 6.60 (s, 1H), 7.25-7.37 (m, 2H), 7.54-7.59 (m, 2H), 7.98-8.03 (m, 3H), 8.89 (s, 1H), 9.08 (s, 1H), 10.55 (s, 1H), 11.23 (s, 1H). |
| 20 | 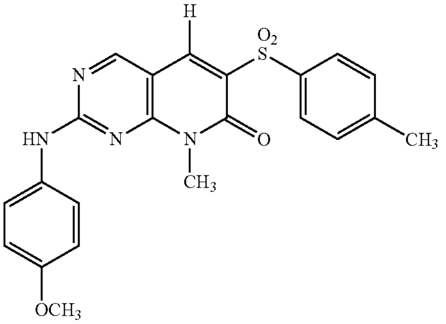 [SMILES: COc1ccc(Nc2ncc3cc(S(=O)(=O)c4ccc(C)cc4)c(=O)n(C)c3n2)cc1] | 2-(4-methoxyphenylamino)-8-methyl-6-tosylpyrido[2,3-a]pyrimidin-7(8H)-one | m.p. 336-340° C.; $^1$H-NMR (DMSO-$d_6$) δ 2.39 (s, 3H), 3.47 (s, 3H), 3.75 (s, 3H), 6.41 (d, J = 8.0 Hz, 2H), 6.88 (d, J = 7.8 Hz, 2H), 7.41 (d, J = 8.0 Hz, 2H), 7.88 (d, J = 7.8 Hz, 2H), 8.80 (s, 1H), 9.05 (s, 1H), 10.20 (s, 1H). |
| 21 | 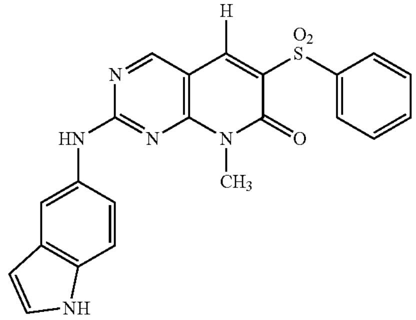 [SMILES: Cn1c(=O)c(S(=O)(=O)c2ccccc2)cc2cnc(Nc3ccc4[nH]ccc4c3)nc21] | 2-(1H-indol-5-ylamino)-8-methyl-6-(phenylsulfonyl)pyrido[2,3-a]pyrimidin-7(8H)-one | m.p. 340-344° C.; $^1$H-NMR (DMSO-$d_6$) δ 3.47 (s, 3H), 6.41 (s, 1H), 7.13-7.24 (m, 3H), 7.33-7.38 (m, 2H), 7.46-7.48 (m, 2H), 7.67-7.71 (m, 2H), 8.82 (s, 1H), 9.03 (s, 1H), 10.49 (s, 1H), 11.08 (s, 1H). |
| 22 | 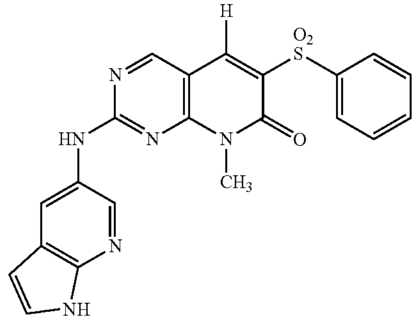 [SMILES: Cn1c(=O)c(S(=O)(=O)c2ccccc2)cc2cnc(Nc3cnc4[nH]ccc4c3)nc21] | 2-(1H-pyrrolo[2,3-b]pyridin-5-ylamino)-8-methyl-6-(phenylsulfonyl)pyrido[2,3-d]pyrimidin-7(8H)-one | m.p. 280-284° C.; $^1$H-NMR (DMSO-$d_6$) δ 3.49 (s, 3H), 6.49 (s, 1H), 7.14-7.29 (m, 2H), 7.50-7.77 (m, 3H), 8.06-8.07 (m, 3H), 8.89 (s, 1H), 9.10 (s, 1H), 10.65 (s, 1H), 11.67 (s, 1H). |

TABLE 1-continued

Compound Examples

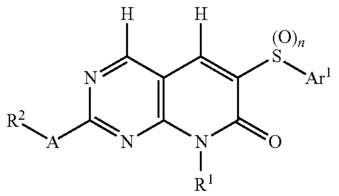

| Example | Structure | Name | Characterization Data |
|---|---|---|---|
| 23 | 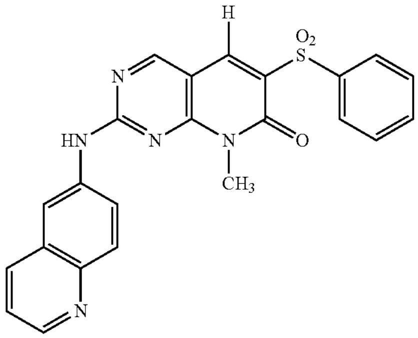 [SMILES: Cn1c(=O)c(S(=O)(=O)c2ccccc2)cc2cnc(Nc3ccc4ncccc4c3)nc21] | 8-methyl-6-(phenylsulfonyl)-2-(quinolin-6-ylamino)pyrido[2,3-d]pyrimidin-7(8H)-one | m.p. 348-350° C.; $^1$H-NMR (DMSO-$d_6$) δ 3.50 (s, 3H), 6.80 (s, 1H), 7.42-7.49 (m, 2H), 7.62-7.71 (m, 3H), 7.82-7.86 (m, 3H), 8.10-8.23 (m, 2H), 8.65-8.83 (m, 2H), 11.18 (s, 1H). |
| 24 | 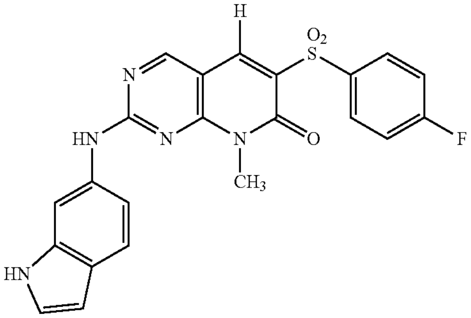 [SMILES: Cn1c(=O)c(S(=O)(=O)c2ccc(F)cc2)cc2cnc(Nc3ccc4cc[nH]c4c3)nc21] | 2-(1H-indol-6-ylamino)-6-(4-fluorophenylsulfonyl)-8-methylpyrido[2,3-d]pyrimidin-7(8H)-one | m.p. >350° C.; $^1$H-NMR (DMSO-$d_6$) δ 3.30 (s, 3H), 6.12 (s, 1H), 7.05-7.23 (m, 5H), 7.83-7.91 (m, 3H), 8.58 (s, 1H), 8.80 (s, 1H), 10.18 (s, 1H), 10.89 (s, 1H). |
| 25 | 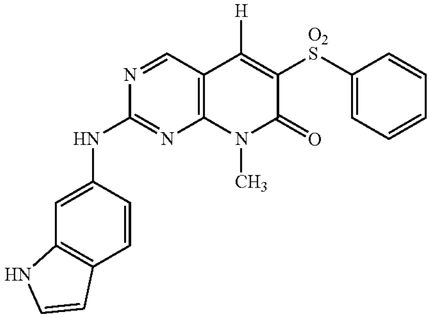 [SMILES: Cn1c(=O)c(S(=O)(=O)c2ccccc2)cc2cnc(Nc3ccc4cc[nH]c4c3)nc21] | 2-(1H-indol-6-ylamino)-8-methyl-6-(phenylsulfonyl)pyrido[2,3-d]pyrimidin-7(8H)-one | m.p. >350° C.; $^1$H-NMR (DMSO-$d_6$) δ 3.29 (s, 3H), 6.12 (s, 1H), 6.90-7.04 (m, 3H), 7.21-7.44 (m, 3H), 7.74-7.94 (m, 3H), 8.59 (s, 1H), 8.81 (s, 1H), 10.38 (s, 1H), 10.90 (s, 1H). |
| 26 | 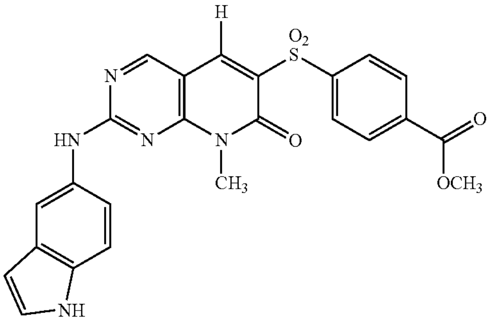 [SMILES: COC(=O)c1ccc(S(=O)(=O)c2cc3cnc(Nc4ccc5[nH]ccc5c4)nc3n(C)c2=O)cc1] | methyl 4-(2-(1H-indol-5-ylamino)-7,8-dihydro-8-methyl-7-oxopyrido[2,3-d]pyrimidin-6-ylsulfonyl)benzoate | m.p. 305-310° C.; $^1$H-NMR (DMSO-$d_6$) δ 3.30 (s, 3H), 3.73 (s, 3H), 6.25 (s, 1H), 7.17-7.22 (m, 4H), 7.95-8.00 (m, 4H), 8.69 (s, 1H), 8.89 (s, 1H), 10.40 (s, 1H), 10.91 (s, 1H). |

TABLE 1-continued

Compound Examples

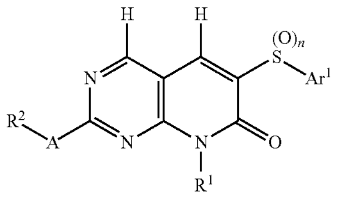

| Example | Structure | Name | Characterization Data |
|---|---|---|---|
| 27 | 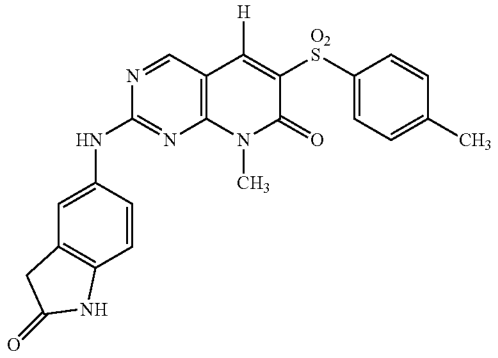 [SMILES: Cc1ccc(S(=O)(=O)c2cc3cnc(Nc4ccc5c(c4)CC(=O)N5)nc3n(C)c2=O)cc1] | 2-(2-oxoindolin-5-ylamino)-8-methyl-6-tosylpyrido[2,3-d]pyrimidin-7(8H)-one | m.p. 280° C.; $^1$H-NMR (DMSO-$d_6$) δ 2.39 (s, 3H), 3.47 (s, 3H), 3.69 (s, 2H), 6.31-6.67 (m, 2H), 7.03-7.48 (m, 3H), 7.61-7.74 (m, 2H), 8.67 (s, 1H), 8.90 (s, 1H), 9.91 (s, 1H), 10.27 (s, 1H). |
| 28 | 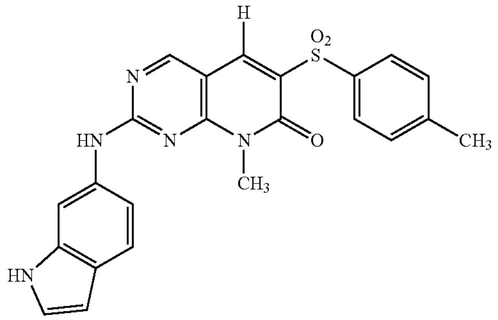 [SMILES: Cc1ccc(S(=O)(=O)c2cc3cnc(Nc4ccc5cc[nH]c5c4)nc3n(C)c2=O)cc1] | 2-(1H-indol-6-ylamino)-8-methyl-6-tosylpyrido[2,3-d]pyrimidin-7(8H)-one | m.p. 334-336° C.; $^1$H-NMR (DMSO-$d_6$) δ 2.38 (s, 3H), 3.54 (s, 3H), 6.38 (s, 1H), 7.04-7.49 (m, 5H), 7.90-8.01 (m, 2H), 8.17 (s, 1H), 8.85 (s, 1H), 9.05 (s, 1H), 10.58 (s, 1H), 11.15 (s, 1H). |
| 29 | 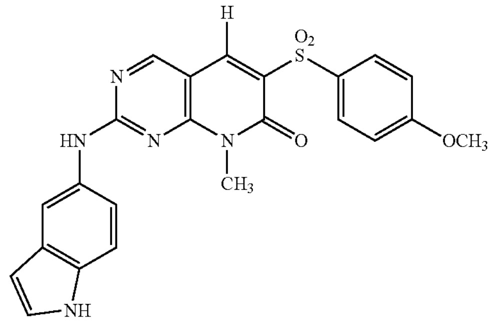 [SMILES: COc1ccc(S(=O)(=O)c2cc3cnc(Nc4ccc5[nH]ccc5c4)nc3n(C)c2=O)cc1] | 2-(1H-indol-5-ylamino)-6-(4-methoxyphenylsulfonyl)-8-methylpyrido[2,3-d]pyrimidin-7(8H)-one | m.p. 260-262° C.; $^1$H-NMR (DMSO-$d_6$) δ 3.25 (s, 3H), 3.60 (s, 3H), 6.17 (s, 1H), 6.74-7.38 (m, 6H), 7.62-7.79 (m, 2H), 8.53 (s, 1H), 8.78 (s, 1H), 10.23 (s, 1H), 10.84 (s, 1H). |
| 30 | 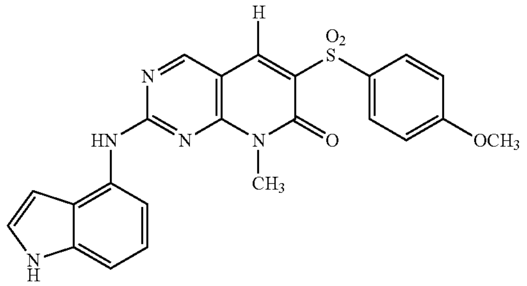 [SMILES: COc1ccc(S(=O)(=O)c2cc3cnc(Nc4cccc5[nH]ccc45)nc3n(C)c2=O)cc1] | 2-(1H-indol-4-ylamino)-6-(4-methoxyphenylsulfonyl)-8-methylpyrido[2,3-d]pyrimidin-7(8H)-one | m.p. 289-292° C.; $^1$H-NMR (DMSO-$d_6$) δ 3.31 (s, 3H), 3.79 (s, 3H), 6.60 (s, 1H), 7.03-7.50 (m, 6H), 7.87-7.90 (m, 2H), 8.75 (s, 1H), 9.01 (s, 1H), 10.28 (s, 1H), 11.10 (s, 1H). |

TABLE 1-continued

Compound Examples

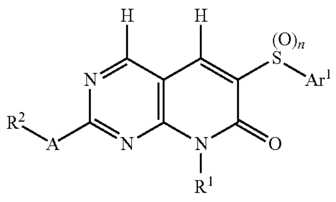

| Example | Structure | Name | Characterization Data |
| --- | --- | --- | --- |
| 31 | 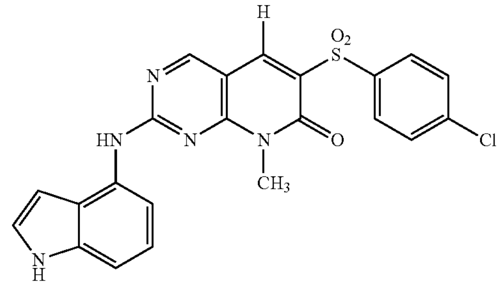 [SMILES: Cn1c(=O)c(S(=O)(=O)c2ccc(Cl)cc2)cc2cnc(Nc3cccc4[nH]ccc34)nc21] | 2-(1H-indol-4-ylamino)-6-(4-chlorophenylsulfonyl)-8-methylpyrido[2,3-d]pyrimidin-7(8H)-one | m.p. 320-324° C.; $^1$H-NMR (DMSO-$d_6$) δ 3.30 (s, 3H), 6.44 (s, 1H), 6.80-7.08 (m, 4H), 7.59 (d, J = 8.4 Hz, 2H), 7.91 (d, J = 8.4 Hz, 2H), 8.75 (s, 1H), 8.98 (s, 1H), 10.30 (s, 1H), 11.07 (s, 1H). |
| 32 | 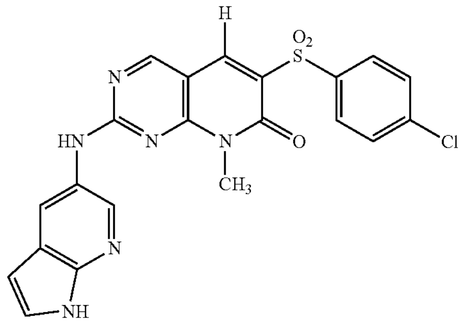 [SMILES: Cn1c(=O)c(S(=O)(=O)c2ccc(Cl)cc2)cc2cnc(Nc3cnc4[nH]ccc4c3)nc21] | 2-(1H-pyrrolo[2,3-b]pyridin-5-ylamino)-6-(4-chlorophenylsulfonyl)-8-methylpyrido[2,3-d]pyrimidin-7(8H)-one | m.p. 296-298° C.; $^1$H-NMR (DMSO-$d_6$) δ 3.45 (s, 3H), 6.40 (s, 1H), 7.08-7.26 (m, 4H), 7.69-7.74 (m, 2H), 7.92-8.04 (m, 2H), 8.85 (s, 1H), 9.40 (s, 1H), 10.63 (s, 1H), 11.49 (s, 1H). |
| 33 | 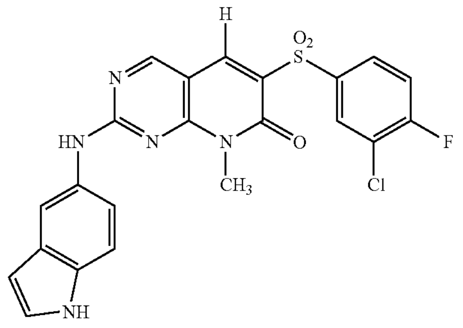 [SMILES: Cn1c(=O)c(S(=O)(=O)c2ccc(F)c(Cl)c2)cc2cnc(Nc3ccc4[nH]ccc4c3)nc21] | 2-(1H-indol-5-ylamino)-6-(3-chloro-4-fluorophenylsulfonyl)-8-methylpyrido[2,3-d]pyrimidin-7(8H)-one | m.p. 250-255° C.; $^1$H-NMR (DMSO-$d_6$) δ 3.48 (s, 3H), 6.42 (s, 1H), 7.13-7.48 (m ,4H), 7.65-7.70 (m, 1H), 8.03 (s, 1H), 8.19-8.20 (m, 1H), 8.81 (s, 1H), 9.03 (s, 1H), 10.54 (s, 1H), 11.09 (s, 1H). |
| 34 | 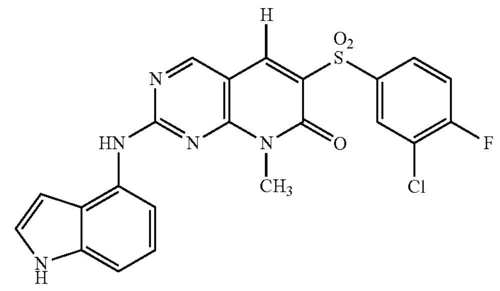 [SMILES: Cn1c(=O)c(S(=O)(=O)c2ccc(F)c(Cl)c2)cc2cnc(Nc3cccc4[nH]ccc34)nc21] | 2-(1H-indol-4-ylamino)-6-(3-chloro-4-fluorophenylsulfonyl)-8-methylpyrido[2,3-d]pyrimidin-7(8H)-one | m.p. 315-320° C.; $^1$H-NMR (DMSO-$d_6$) δ 3.40 (s, 3H), 6.55 (s, 1H), 7.08-7.39 (m, 4H), 7.64-7.68 (m, 1H), 8.02-8.04 (m, 1H), 8.18-8.20 (m, 1H), 8.84 (s, 1H), 9.06 (s, 1H), 10.41 (s, 1H), 11.17 (s, 1H). |

TABLE 1-continued

Compound Examples

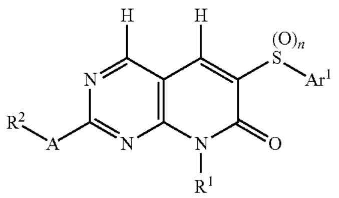

| Example | Structure | Name | Characterization Data |
|---|---|---|---|
| 35 | 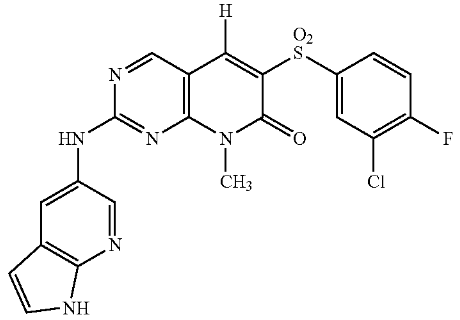 [SMILES: Cn1c(=O)c(S(=O)(=O)c2ccc(F)c(Cl)c2)cc2cnc(Nc3cnc4[nH]ccc4c3)nc21] | 2-(1H-pyrrolo[2,3-b]pyridin-5-ylamino)-6-(3-chloro-4-fluorophenylsulfonyl)-8-methylpyrido[2,3-d]pyrimidin-7(8H)-one | m.p. 320-325° C.; $^1$H-NMR (DMSO-$d_6$) δ 3.46 (s, 3H), 6.45-6.48 (m, 1H), 7.47-7.70 (m, 2H), 8.04-8.52 (m, 4H), 8.84 (s, 1H), 9.07 (s, 1H), 10.65 (s, 1H), 11.63 (s, 1H). |
| 36 | 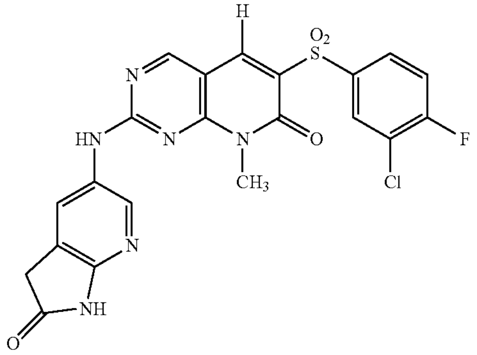 [SMILES: Cn1c(=O)c(S(=O)(=O)c2ccc(F)c(Cl)c2)cc2cnc(Nc3cnc4c(c3)CC(=O)N4)nc21] | 2-(2-oxoindolin-5-ylamino)-6-(3-chloro-4-fluorophenylsulfonyl)-8-methylpyrido[2,3-d]pyrimidin-7(8H)-one | m.p. >350° C.; $^1$H-NMR (DMSO-$d_6$) δ 3.47 (s, 1H), 3.50 (s, 2H), 6.80-6.82 (m, 1H), 7.61-7.68 (m, 3H), 8.17-8.19 (m, 2H), 8.82 (s, 1H), 9.04 (s, 1H), 10.37 (s, 1H), 10.50 (s, 1H). |
| 37 | 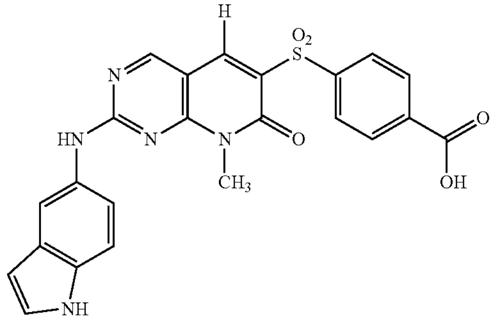 [SMILES: Cn1c(=O)c(S(=O)(=O)c2ccc(C(=O)O)cc2)cc2cnc(Nc3ccc4[nH]ccc4c3)nc21] | 4-(2-(1H-indol-5-ylamino)-7,8-dihydro-8-methyl-7-oxopyrido[2,3-d]pyrimidin-6-ylsulfonyl) benzoic acid | m.p. 262-265° C.; $^1$H-NMR (DMSO-$d_6$) δ 3.66 (s, 3H), 6.18 (s, 1H), 7.11-7.24 (m, 4H), 7.64-7.91 (m, 4H), 8.62 (s, 1H), 8.82 (s, 1H), 10.08 (s, 1H), 10.31 (s, 1H), 10.88 (s, 1H). |
| 38 | 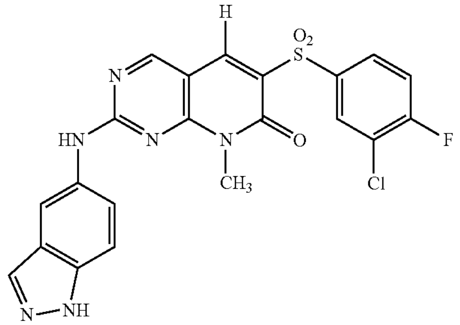 [SMILES: Cn1c(=O)c(S(=O)(=O)c2ccc(F)c(Cl)c2)cc2cnc(Nc3ccc4[nH]ncc4c3)nc21] | 2-(1H-indazol-5-ylamino)-6-(3-chloro-4-fluorophenylsulfonyl)-8-methylpyrido[2,3-d]pyrimidin-7(8H)-one | $^1$H-NMR (DMSO-$d_6$) δ 3.51 (s, 3H), 7.54-8.20 (m, 7H), 8.84 (s, 1H), 9.07 (s, 1H), 10.70 (s, 1H), 13.05 (s, 1H). |

TABLE 1-continued

Compound Examples

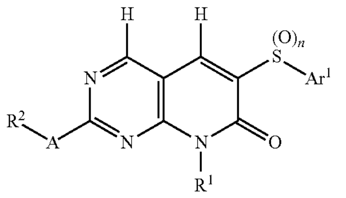

| Example | Structure | Name | Characterization Data |
|---|---|---|---|
| 39 | 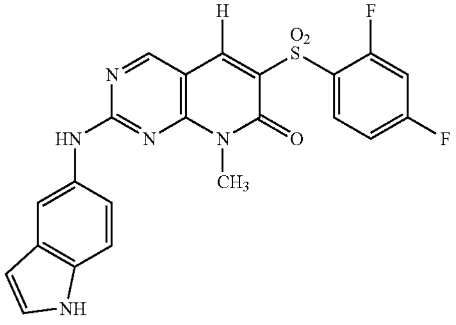 [SMILES: Cn1c(=O)c(S(=O)(=O)c2ccc(F)cc2F)cc2cnc(Nc3ccc4[nH]ccc4c3)nc21] | 2-(1H-indol-5-ylamino)-6-(2,4-difluorophenylsulfonyl)-8-methylpyrido[2,3-d]pyrimidin-7(8H)-one | $^1$H-NMR (DMSO-$d_6$) δ 3.60 (s, 3H), 6.50 (s, 1H), 7.20-8.40 (m, 7H), 8.80 (s, 1H), 9.10 (s, 1H), 10.50 (s, 1H), 11.30 (s, 1H). |
| 40 | 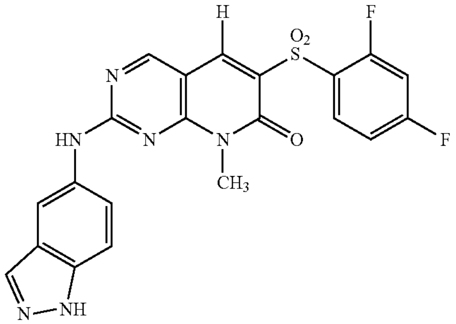 [SMILES: Cn1c(=O)c(S(=O)(=O)c2ccc(F)cc2F)cc2cnc(Nc3ccc4[nH]ncc4c3)nc21] | 2-(1H-indazol-5-ylamino)-6-(2,4-difluorophenylsulfonyl)-8-methylpyrido[2,3-d]pyrimidin-7(8H)-one | $^1$H-NMR (DMSO-$d_6$) δ 3.55 (s, 3H), 7.41-8.53 (m, 7H), 8.82 (s, 1H), 9.15 (s, 1H), 10.70 (s, 1H), 13.00 (s, 1H). |
| 41 | 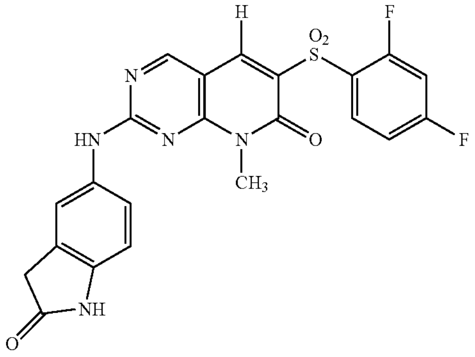 [SMILES: Cn1c(=O)c(S(=O)(=O)c2ccc(F)cc2F)cc2cnc(Nc3ccc4c(c3)CC(=O)N4)nc21] | 6-(2,4-difluorophenylsulfonyl)-2-(2-oxoindolin-5-ylamino)-8-methylpyrido[2,3-d]pyrimidin-7(8H)-one | $^1$H-NMR (DMSO-$d_6$) δ 3.57 (s, 3H), 3.66 (2H), 6.22-6.37 (m, 1H), 6.48 (d, 1H), 6.79 (d, 1H), 7.12-7.60 (m, 3H), 8.82 (s, 1H), 9.10 (s, 1H), 10.40 (s, 1H), 10.55 (s, 1H). |

TABLE 1-continued

Compound Examples

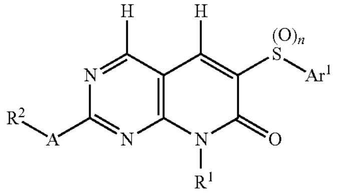

| Example | Structure | Name | Characterization Data |
| --- | --- | --- | --- |
| 42 | 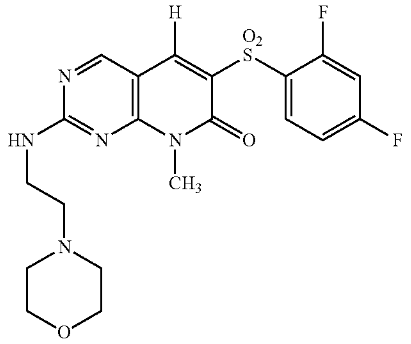 [SMILES: Cn1c(=O)c(S(=O)(=O)c2ccc(F)cc2F)cc2cnc(NCCN3CCOCC3)nc21] | 6-(2,4-difluorophenylsulfonyl)-2-(2-morpholinoethylamino)-8-methylpyrido[2,3-d]pyrimidin-7(8H)-one | $^1$H-NMR (DMSO-$d_6$) δ 1.72-1.74 (m, 2H), 2.28-2.32 (m, 6H), 3.22 (s, 2H), 3.40-3.43 (m, 4H), 3.55 (s, 3H), 6.22-6.70 (m, 3H), 7.80 (s, 1H), 8.55 (s, 1H), 8.90 (s, 1H). |
| 43 | 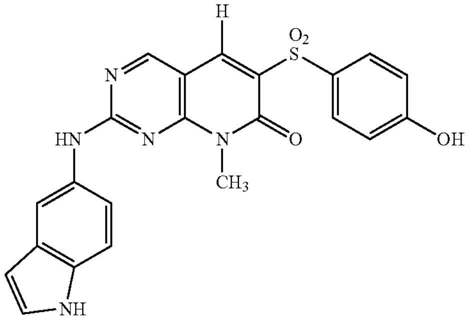 [SMILES: Cn1c(=O)c(S(=O)(=O)c2ccc(O)cc2)cc2cnc(Nc3ccc4[nH]ccc4c3)nc21] | 2-(1H-indol-5-ylamino)-6-(4-hydroxyphenylsulfonyl)-8-methylpyrido[2,3-d]pyrimidin-7(8H)-one | $^1$H-NMR (DMSO-$d_6$) δ 3.55 (s, 3H), 6.39 (s, 1H), 6.89 (d, 2H), 7.01-7.70 (m, 4H), 7.80 (d, 2H), 8.72 (s, 1H), 9.08 (s, 1H), 10.55 (s, 1H), 11.29 (s, 1H). |
| 44 | 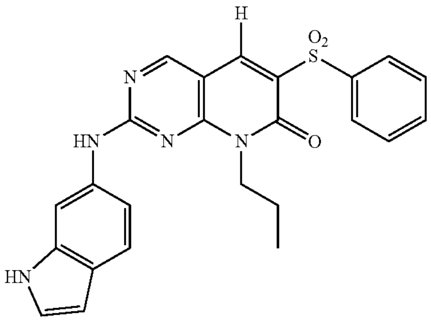 [SMILES: CCCn1c(=O)c(S(=O)(=O)c2ccccc2)cc2cnc(Nc3ccc4cc[nH]c4c3)nc21] | 2-(1H-indol-6-ylamino)-6-(phenylsulfonyl)-8-propylpyrido[2,3-]pyrimidin-7(8H)-one | m.p. 272-273° C.; $^1$H-NMR (DMSO-$d_6$) δ 11.06 (br s, 1H), 10.55 (br s, 1H), 9.04 (s, 1H), 8.81 (s, 1H), 7.90-7.99 (m, 3H), 7.57-7.68 (m, 3H), 7.40-7.48 (m, 2H), 7.27-7.29 (m, 1H), 6.37 (s, 1H), 4.12 (t, 2H), 1.55-1.62 (m, 2H), 0.83 (t, 3H). |
| 45 | 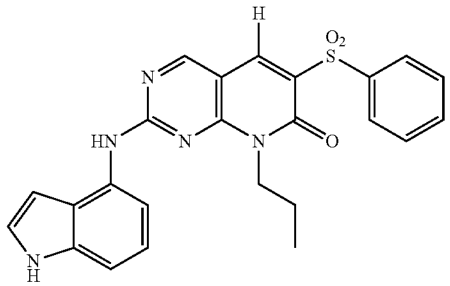 [SMILES: CCCn1c(=O)c(S(=O)(=O)c2ccccc2)cc2cnc(Nc3cccc4[nH]ccc34)nc21] | 2-(1H-indol-4-ylamino)-6-(phenylsulfonyl)-8-propylpyrido[2,3-d]pyrimidin-7(8H)-one | m.p. 260-261° C.; $^1$H-NMR (DMSO-$d_6$) δ 11.15 (br s, 1H), 10.34 (br s, 1H), 9.07 (s, 1H), 8.83 (s, 1H), 7.96-7.98 (m, 2H), 7.56-7.70 (m, 4H), 7.27-7.2p (m, 1H), 7.20-7.22 (m, 1H), 7.03-7-08 (m, 1H), 6.70 (s, 1H), 3.96 (t, 2H), 1.46-1.48 (m, 2H), 0.77 (t, 3H). |

TABLE 1-continued

Compound Examples

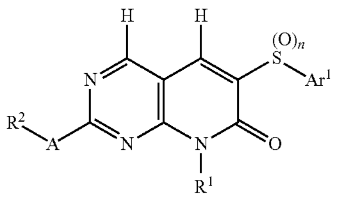

| Example | Structure | Name | Characterization Data |
| --- | --- | --- | --- |
| 46 | 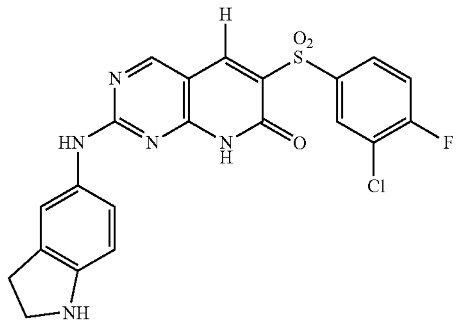 [SMILES: O=c1[nH]c2nc(Nc3ccc4c(c3)CCN4)ncc2cc1S(=O)(=O)c1ccc(F)c(Cl)c1] | 2-(1H-indol-5-ylamino)-6-(3-chloro-4-fluorophenylsulfonyl)pyrido[2,3-d]pyrimidin-7(8H)-one | m.p. 200-203° C.; $^1$H-NMR (DMSO-$d_6$) δ 6.38 (s, 1H), 7.30-7.35 (m, 7H), 8.45 (s, 1H), 9.53 (s, 1H), 9.57 (s, 1H), 10.98 (s, 1H). |
| 47 | 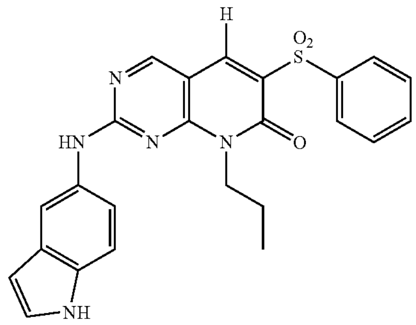 [SMILES: CCCn1c(=O)c(S(=O)(=O)c2ccccc2)cc2cnc(Nc3ccc4[nH]ccc4c3)nc21] | 2-(1H-indol-5-ylamino)-6-(phenylsulfonyl)-8-propylpyrido[2,3-d]pyrimidin-7(8H)-one | m.p. 293-295° C.; $^1$H-NMR (DMSO-$d_6$) δ 11.07 (br s, 1H), 10.50 (br s, 1H), 9.02 (s, 1H), 8.80 (s, 1H), 7.96-7.99 (m, 2H), 7.56-7.68 (m, 3H), 7.35-7.40 (m, 2H), 7.09-7.25 (m, 2H), 6.35 (s, 1H), 4.08 (t, 2H), 1.54-1.62 (m ,2H), 0.90 (t, 3H). |
| 48 | 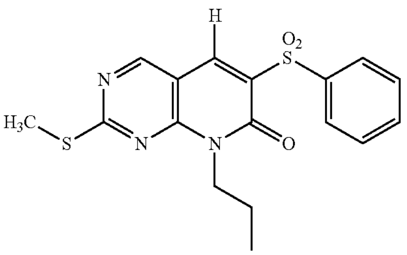 [SMILES: CCCn1c(=O)c(S(=O)(=O)c2ccccc2)cc2cnc(SC)nc21] | 2-(methylsulfanyl)-6-(phenylsulfonyl)-8-propylpyrido[2,3-d]pyrimidin-7(8H)-one | m.p. 231-232° C.; $^1$H-NMR (DMSO-$d_6$) δ 9.18 (s, 1H), 9.01 (s, 1H), 7.97-8.07 (m, 2H), 7.58-7.70 (m, 3H), 4.15 (t, 2H), 2.58 (s, 3H), 1.52-1.59 (m, 2H), 0.84 (t, 3H). |
| 49 | 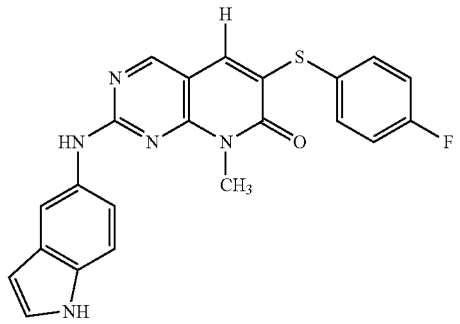 [SMILES: Cn1c(=O)c(Sc2ccc(F)cc2)cc2cnc(Nc3ccc4[nH]ccc4c3)nc21] | 2-(1H-indol-5-ylamino)-6-(4-fluorophenylsulfanyl)-8-methylpyrido[2,3-d]pyrimidin-7(8H)-one | |

TABLE 1-continued

Compound Examples

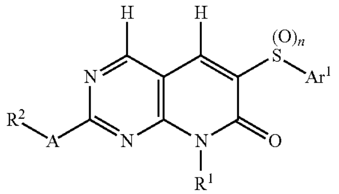

| Example | Structure | Name | Characterization Data |
| --- | --- | --- | --- |
| 50 | 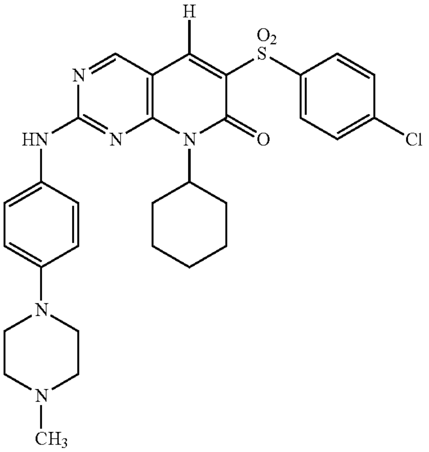 [SMILES: CN1CCN(c2ccc(Nc3ncc4cc(S(=O)(=O)c5ccc(Cl)cc5)c(=O)n(C5CCCCC5)c4n3)cc2)CC1] | 2-(4-(4-methylpiperazin-1-yl)phenylamino)-6-(4-chlorophenylsulfonyl)-8-cyclohexylpyrido[2,3-d]pyrimidin-7(8H)-one | m.p. 259-260° C.; $^1$H-NMR (DMSO-$d_6$) δ 8.63 (s, 1H), 8.52 (s, 1H), 8.00-8.06 (m, 2H), 7.30-7.48 (m, 5H), 6.91-6.97 (m, 2H), 5.35 (br s, 1H), 3.24-3.27 (m, 4H), 2.67-2.71 (m, 4H), 2.48 (s, 3H), 1.76-1.79 (m, 2H), 1.50-1.53 (m, 4H), 1.27-1.31 (m, 4H). |
| 51 | 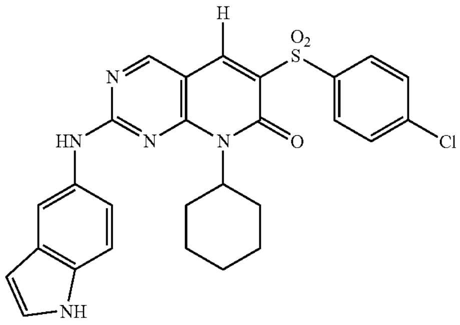 [SMILES: O=c1c(S(=O)(=O)c2ccc(Cl)cc2)cc2cnc(Nc3ccc4[nH]ccc4c3)nc2n1C1CCCCC1] | 2-(1H-indol-5-ylamino)-6-(4-chlorophenylsulfonyl)-8-cyclohexylpyrido[2,3-d]pyrimidin-7(8H)-one | m.p. 305-307° C.; $^1$H-NMR (DMSO-$d_6$) δ 11.09 (br s, 1H), 10.48 (br s, 1H), 9.00 (s, 1H), 8.75 (s, 1H), 7.95-7.98 (m, 2H), 7.67-7.70 (m, 2H), 7.21-7.37 (m, 4H), 7.35-45 (m, 1H), 5.35 (br s, 1H), 1.68-1.78 (m, 2H), 1.50-1.60 (m, 4H), 1.15-1.21 (m, 4H). |
| 52 | 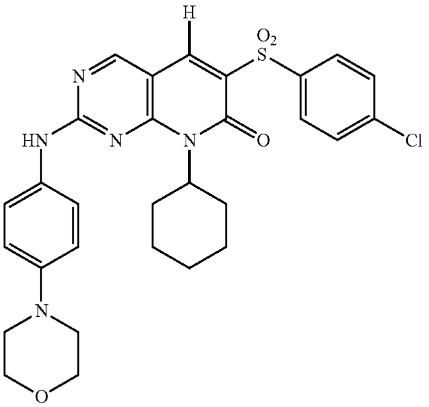 [SMILES: O=c1c(S(=O)(=O)c2ccc(Cl)cc2)cc2cnc(Nc3ccc(N4CCOCC4)cc3)nc2n1C1CCCCC1] | 6-(4-chlorophenylsulfonyl)-2-(4-morpholinophenylamino)-8-cyclohexylpyrido[2,3-d]pyrimidin-7(8H)-one | m.p. 329-331° C.; $^1$H-NMR (DMSO-$d_6$) δ 8.64 (s, 1H), 8.53 (s, 1H), 8.03-8.07 (m, 2H), 7.47-7.52 (m, 4H), 6.91-6.96 (m, 2H), 5.22 (br s, 1H), 3.82-3.90 (m, 4H), 3.15-3.18 (m, 4H), 1.79 (br s, 2H), 1.43-1.58 (m, 6H), 1.25-1.32 (m, 2H). |

TABLE 1-continued

Compound Examples

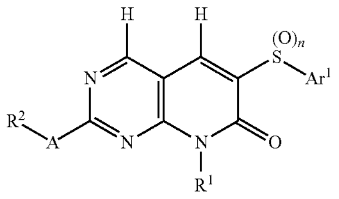

| Example | Structure | Name | Characterization Data |
|---|---|---|---|
| 53 | 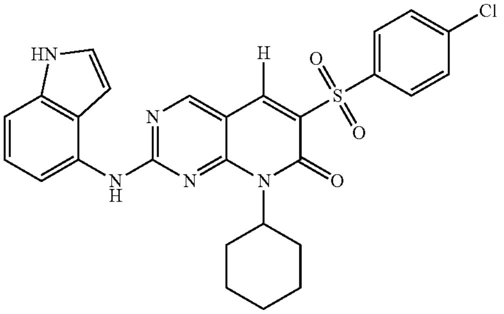 [SMILES: O=c1c(S(=O)(=O)c2ccc(Cl)cc2)cc2cnc(Nc3cccc4[nH]ccc34)nc2n1C1CCCCC1] | 2-(1H-indol-4-ylamino)-6-(4-chlorophenylsulfonyl)-8-cyclohexylpyrido[2,3-d]pyrimidin-7(8H)-one | m.p. 300-302° C.; $^1$H-NMR (DMSO-$d_6$) δ 8.68 (s, 1H), 8.54 (s, 1H), 8.41 (br s, 1H), 8.02-8.07 (m, 2H), 7.48-7.53 (m, 2H), 7.22-7.33 (m, 4H), 6.54-6.57 (m, 1H), 5.25 (br s, 1H), 1.50-1.62 (m, 8H), 1.24-1.31 (m, 2H). |
| 54 | 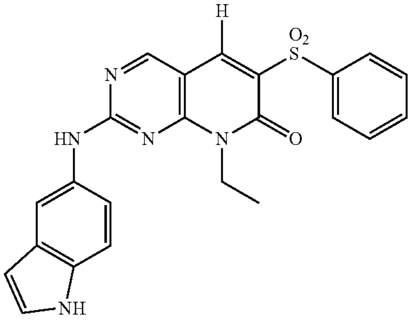 [SMILES: CCn1c(=O)c(S(=O)(=O)c2ccccc2)cc2cnc(Nc3ccc4[nH]ccc4c3)nc21] | 2-(1H-indol-5-ylamino)-8-ethyl-6-(phenylsulfonyl)pyrido[2,3-d]pyrimidin-7(8H)-one | m.p. >400° C.; $^1$H-NMR (DMSO-$d_6$) δ 11.06 (br s, 1H), 10.49 (br s, 1H), 9.02 (s, 1H), 8.80 (s, 1H), 7.96-7.99 (m, 2H), 7.59-7.68 (m, 3H), 7.46-7.47 (m, 1H), 7.31-7.36 (m, 2H), 7.12-7.16 (m, 1H), 6.39-6.41 (m, 1H), 3.46 (q, 2H), 2.48 (t, 3H). |
| 55 | 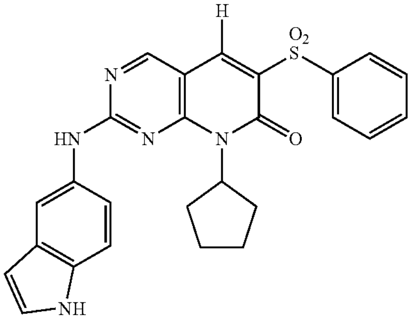 [SMILES: O=c1c(S(=O)(=O)c2ccccc2)cc2cnc(Nc3ccc4[nH]ccc4c3)nc2n1C1CCCC1] | 2-(1H-indol-5-ylamino)-8-cyclopentyl-6-(phenylsulfonyl)pyrido[2,3-d]pyrimidin-7(8H)-one | m.p. 272-273° C.; $^1$H-NMR (DMSO-$d_6$) δ 8.65 (s, 1H), 8.54 (s, 1H), 8.28 (br s, 1H), 8.10-8.13 (m, 2H), 7.81-7.82 (m, 1H), 7.49-7.61 (m, 3H), 7.39-7.42 (m, 1H), 7.19-7.28 (m, 3H), 5.65 (m, 1H), 2.20-2.36 (m, 2H), 1.58-1.68 (m, 6H). |
| 56 | 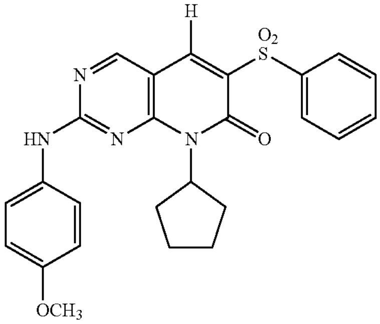 [SMILES: COc1ccc(Nc2ncc3cc(S(=O)(=O)c4ccccc4)c(=O)n(C4CCCC4)c3n2)cc1] | 2-(4-methoxyphenylamino)-8-cyclopentyl-6-(phenylsulfonyl)pyrido[2,3-d]pyrimidin-7(8H)-one | m.p. 201° C.; $^1$H-NMR (DMSO-$d_6$) δ 8.66 (s, 1H), 8.56 (s, 1H), 8.10-8.13 (m, 2H), 7.58-7.64 (m, 3H), 7.39-7.47 (m, 2H), 6.91-6.95 (m, 2H), 5.65 (br s, 1H), 3.85 (s, 3H), 2.18-2.25 (m, 2H), 1.52-1.71 (m, 6H). |

TABLE 1-continued

Compound Examples

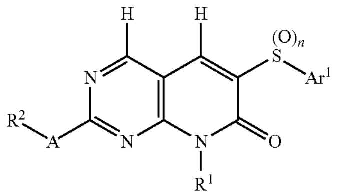

| Example | Structure | Name | Characterization Data |
|---|---|---|---|
| 57 | 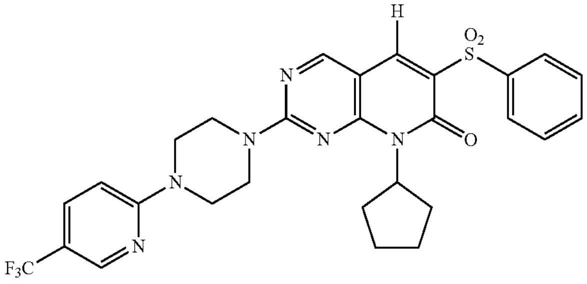 [SMILES: O=c1c(S(=O)(=O)c2ccccc2)cc2cnc(N3CCN(c4ccc(C(F)(F)F)cn4)CC3)nc2n1C1CCCC1] | 8-cyclopentyl-2-(4-(5-(trifluoromethyl)pyridin-2-yl)piperazin-1-yl)-6-(phenylsulfonyl)pyrido[2,3-d]pyrimidin-7(8H)-one | m.p. 258-259° C.; $^{1}$H-NMR (DMSO-$d_6$) δ 8.49 (s, 1H), 8.37 (s, 1H), 8.28-8.30 (m, 1H), 7.94-7.96 (m, 2H), 7.51-7.55 (m, 1H) 7.33-7.47 (m, 3H), 6.6.52-6.55 (m, 1H), 5.51-5.57 (m, 1H), 3.89-3.97 (m, 4H), 3.64 (br s, 4H), 2.09-2.19 (m, 2H), 1.78-1.85 (m, 2H), 1.53-1.66 (m, 4H). |
| 58 | 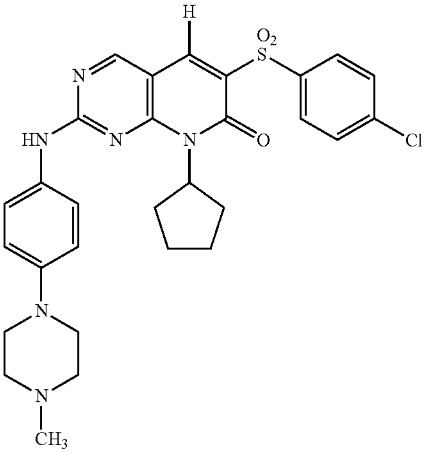 [SMILES: CN1CCN(c2ccc(Nc3ncc4cc(S(=O)(=O)c5ccc(Cl)cc5)c(=O)n(C5CCCC5)c4n3)cc2)CC1] | 2-(4-(4-methylpiperazin-1-yl)phenylamino)-6-(4-chlorophenylsulfonyl)-8-cyclopentylpyrido[2,3-d]pyrimidin-7(8H)-one | m.p. 220-221° C.; $^{1}$H-NMR (DMSO-$d_6$) δ 8.64 (s, 1H), 8.62 (s, 1H), 8.04-8.06 (m, 2H), 5.65-5.69 (m, 1H) ,7.49-7.50 (m, 2H) ,7.37-7.40 (m, 2H), 6.92-6.95 (m, 2H), 3.23-3.27 (m, 4H), 2.67-2.70 (m, 4H), 2.42 (s, 3H), 2.09-2.2.20 (m, 2H), 1.71-1.82 (m, 4H), 1.51-1.63 (m, 2H). |
| 59 | 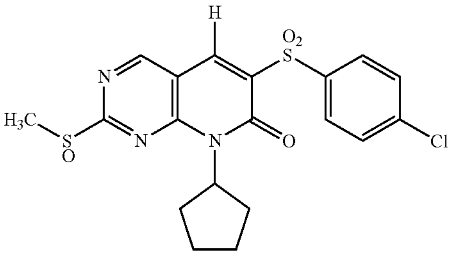 | 6-(4-chlorophenylsulfonyl)-8-cyclopentyl-2-(methylsulfinyl)pyrido[2,3-d]pyrimidin-7(8H)-one | |
| 60 | 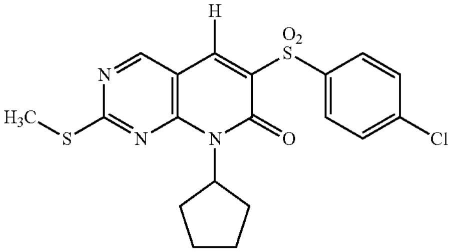 [SMILES: CSc1ncc2cc(S(=O)(=O)c3ccc(Cl)cc3)c(=O)n(C3CCCC3)c2n1] | 6-(4-chlorophenylsulfonyl)-8-cyclopentyl-2-(methylsulfanyl)pyrido[2,3-d]pyrimidin-7(8H)-one | m.p. 222-223° C.; $^{1}$H-NMR (DMSO-$d_6$) δ 8.78 (s, 1H), 8.65 (s, 1H), 8.05-8.09 (m, 2H), 7.49-7.54 (m, 2H), 5.75-5.81 (m, 1H), 2.63 (s, 3H), 2.21-2.28 (m, 2H), 1.95-2.07 (m, 2H), 1.77-1.83 (m, 2H), 1.64-1.69 (m, 2H). |

TABLE 1-continued

Compound Examples

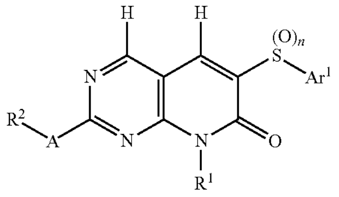

| Example | Structure | Name | Characterization Data |
|---|---|---|---|
| 61 | 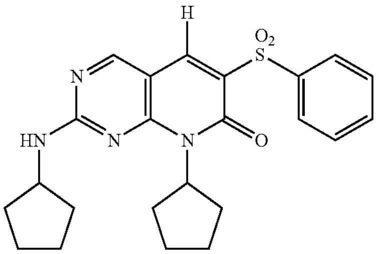 [SMILES: O=c1c(S(=O)(=O)c2ccccc2)cc2cnc(NC3CCCC3)nc2n1C1CCCC1] | 8-cyclopentyl-2-(cyclopentylamino)-6-(phenylsulfonyl)pyrido[2,3-d]pyrimidin-7(8H)-one | m.p. 209-210° C.; $^1$H-NMR (DMSO-$d_6$) δ 8.49 (s, 1H), 8.20 (s, 1H), 7.69-7.75 (m, 2H), 7.30-7.45 (m, 3H), 5.49-5.53 (m, 2H), 3.20 (br s, 2H), 1.59-1.85 (m, 6H), 1.35-1.49 (m, 8H). |
| 62 | 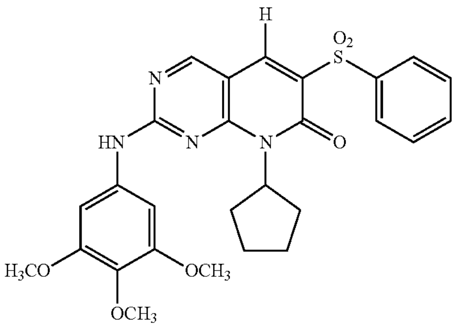 [SMILES: COc1cc(Nc2ncc3cc(S(=O)(=O)c4ccccc4)c(=O)n(C4CCCC4)c3n2)cc(OC)c1OC] | 2-(3,4,5-trimethoxyphenylamino)-8-cyclopentyl-6-(phenylsulfonyl)pyrido[2,3-d]pyrimidin-7(8H)-one | m.p. 119-120° C.; $^1$H-NMR (DMSO-$d_6$) δ 8.70 (s, 1H), 8.58 (s, 1H), 8.11-8.13 (m, 2H), 7.50-7.64 (m, 3H), 7.14-7.19 (m, 2H), 6.82 (s, 2H), 5.75-5.79 (m, 1H), 3.87 (s, 6H), 3.81 (s, 3H), 2.15-2.18 (m, 2H), 1.74-1.87 (m, 4H), 1.58 (br s, 2H). |
| 63 | 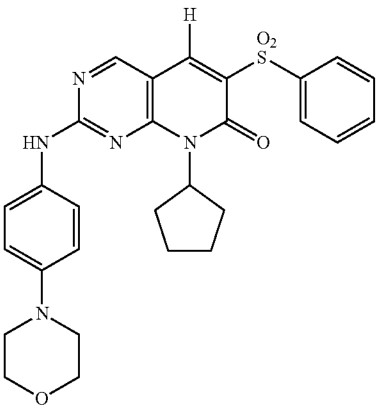 [SMILES: O=c1c(S(=O)(=O)c2ccccc2)cc2cnc(Nc3ccc(N4CCOCC4)cc3)nc2n1C1CCCC1] | 2-(4-morpholinophenylamino)-8-cyclopentyl-6-(phenylsulfonyl)pyrido[2,3-d]pyrimidin-7(8H)-one | m.p. 221-222° C.; $^1$H-NMR (DMSO-$d_6$) δ 8.84 (s, 1H), 8.66 (s, 1H), 8.10-8.13 (m, 2H), 7.52-7.63 (m, 3H), 7.39-7.42 (m, 2H), 6.80-6.95 (m, 2H), 5.81-5.83 (m, 1H), 3.86-3.89 (m, 4H), 3.14-3.18 (m, 4H), 2.18-2.82 (m, 2H), 1.54-1.71 (m, 6H). |

TABLE 1-continued

Compound Examples

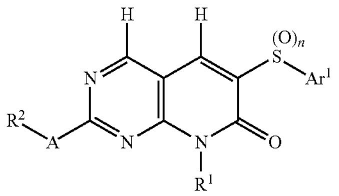

| Example | Structure | Name | Characterization Data |
|---|---|---|---|
| 64 | 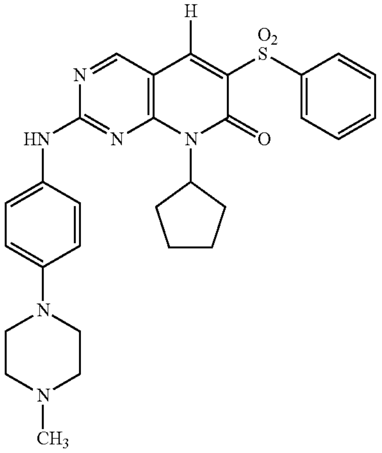 [SMILES: CN1CCN(c2ccc(Nc3ncc4cc(S(=O)(=O)c5ccccc5)c(=O)n(C5CCCC5)c4n3)cc2)CC1] | 2-(4-(4-methylpiperazin-1-yl)phenylamino)-8-cyclopentyl-6-(phenylsulfonyl)pyrido[2,3-d]pyrimidin-7(8H)-one | m.p. 199-200° C.; $^1$H-NMR (DMSO-$d_6$) δ 8.65 (s, 1H), 8.58 (s, 1H), 8.09-8.13 (m, 2H), 7.55-7.63 (m, 3H), 7.37-7.46 (m, 1H), 7.13-7.24 (m, 1H), 6.80-6.96 (m, 2H), 5.82-5.84 (m, 1H), 3.22-3.32 (m, 4H), 2.63-2.71 (m, 4H), 2.46 (s, 3H), 2.18-2.33 (m, 2H), 1.45-1.76 (m, 6H). |
| 65 | 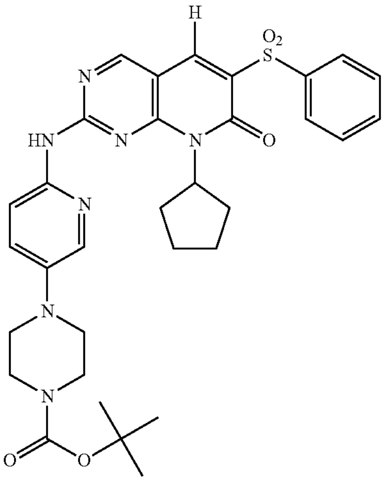 [SMILES: CC(C)(C)OC(=O)N1CCN(c2ccc(Nc3ncc4cc(S(=O)(=O)c5ccccc5)c(=O)n(C5CCCC5)c4n3)nc2)CC1] | 2-(5-(4-tert-butoxycarbonylpiperazin-1-yl)pyridin-2-ylamino)-8-cyclopentyl-6-(phenylsulfonyl)pyrido[2,3-d]pyrimidin-7(8H)-one | m.p. 115-116° C.; $^1$H-NMR (DMSO-$d_6$) δ 8.78 (s, 1H), 8.53 (s, 1H), 7.99-7.12 9 (m, 4H), 7.50-7.62 (m, 3H), 7.31-7.35 (m, 1H), 5.65-5.80 (m, 1H), 3.59-3.61 (m, 4H), 3.09-3.12 (m, 4H), 2.18-2.27 (m, 2H), 1.88-1.97 (m, 2H), 1.53-1.79 (m, 4H), 1.42 (s, 9H). |
| 66 | 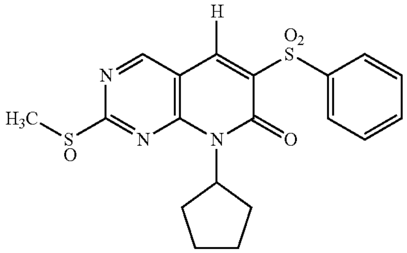 | 8-cyclopentyl-2-(methylsulfinyl)-6-(phenylsulfonyl)pyrido[2,3-d]pyrimidin-7(8H)-one | |

TABLE 1-continued

Compound Examples

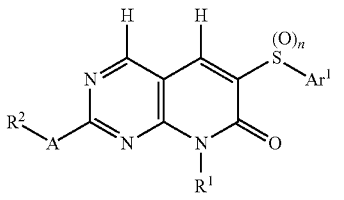

| Example | Structure | Name | Characterization Data |
|---|---|---|---|
| 67 | 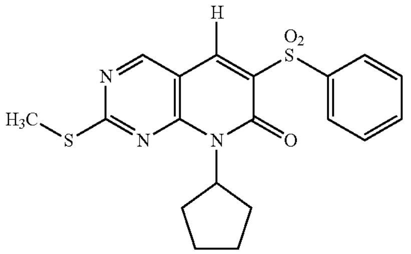 [SMILES: CSc1ncc2cc(S(=O)(=O)c3ccccc3)c(=O)n(C3CCCC3)c2n1] | 8-cyclopentyl-2-(methylsulfanyl)-6-(phenylsulfonyl)pyrido[2,3-d]pyrimidin-7(8H)-one | m.p. 184-185° C.; $^1$H-NMR (DMSO-$d_6$) δ 8.87 (s, 1H), 8.70 (s, 1H), 7.54-7.80 (m, 5H), 5.69-5.72 (m, 1H), 2.66 (s, 3H), 2.20-2.33 (m, 2H), 1.99-2.11 (m, 2H), 1.78-1.88 (m, 2H), 1.61-1.69 (m, 2H). |
| 68 | 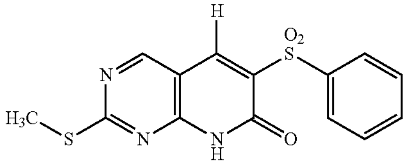 [SMILES: CSc1ncc2cc(S(=O)(=O)c3ccccc3)c(=O)[nH]c2n1] | 2-(methylsulfanyl)-6-(phenylsulfonyl)pyrido[2,3-d]pyrimidin-7(8H)-one | m.p. 280° C. (dec.); $^1$H-NMR (DMSO-$d_6$) δ 9.15 (s, 1H), 9.85 (s, 1H), 7.95-8.05 (m, 2H), 7.64-7.89 (m, 3H), 3.40 (br s, 1H), 2.60 (s, 3H). |

Biology Example 1

Determining the Effect of the Compounds of the Invention on Tumor Cell Lines The effect of the compounds of the invention on tumor cells was determined by the assay described by Latham et al., *Oncogene* 12:827-837 (1996). Tumor cells K562 (chronic myelogenous leukemia; leukemia cell line +ve for Bcr-Abl) or DU145 (prostate cancer) were plated in 12-well dishes at a cell density of $2.5\times10^4$ cells well. The plated cells were treated 24 hours later with a compound of the invention dissolved in DMSO at multiple concentrations ranging from 0.01 μM to 100 μM. The plates were examined 96 hours later under an inverted microscope, Olympus CK-2 using an 10× objective, and compound activity was noted by physical observation. When necessary, the total number of viable cells was determined by trypsinizing the wells and counting the number of viable cells, as determined by trypan blue exclusion, using a hemacytometer.

Representative compounds as shown in Table 2 were tested by above method. The results are contained in Table 2.

Utilizing a similar procedure, the compounds of Example 12 and Example 40 were tested on two normal cell lines: HFL (human fibroblast) and hMSC (human marrow stem cell). The compounds did not kill the normal cells even at a concentration 5-fold higher than a concentration that resulted in tumor cell killing.

TABLE 2

Examples and Biological Activity

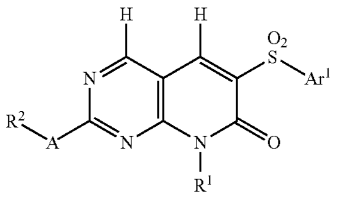

| Example | $R^1$ | $R^2$ | A | $Ar^1$ | K 562 | DU 145 |
|---|---|---|---|---|---|---|
| 3 | —$CH_3$ | 4-chlorophenyl | —NH— | 4-chlorophenyl | +++ | +++ |
| 4 | —$CH_3$ | 4-methoxyphenyl | —NH— | 4-chlorophenyl | +++ | ++ |
| 5 | —$CH_3$ | 3-quinolyl | —NH— | 4-chlorophenyl | +++ | +++ |
| 6 | —$CH_3$ | 5-indolyl | —NH— | 4-chlorophenyl | +++++ | +++++ |
| 7 | —$CH_3$ | 3-morpholinopropyl | —NH— | 4-chlorophenyl | ++ | ++ |
| 8 | —$CH_3$ | 4-acetylpiperazin-1-yl | — | 4-chlorophenyl | + | + |
| 9 | —$CH_3$ | 2-(4-methylpiperazin-1-yl)ethyl | —NH— | 4-chlorophenyl | +++ | ++ |
| 10 | —$CH_3$ | 4-indolyl | —NH— | 4-fluorophenyl | +++++ | +++++ |
| 11 | —$CH_3$ | 5-indolyl | —NH— | 4-fluorophenyl | +++++ | +++++ |

TABLE 2-continued

Examples and Biological Activity

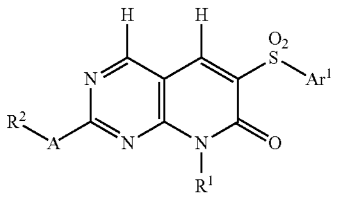

| Example | $R^1$ | $R^2$ | A | $Ar^1$ | K 562 | DU 145 |
|---|---|---|---|---|---|---|
| 3 | —$CH_3$ | 4-chlorophenyl | —NH— | 4-chlorophenyl | +++ | +++ |
| 12 | —$CH_3$ | 1H-pyrrolo[2,3-b]pyridin-5-yl | —NH— | 4-fluorophenyl | +++++ | +++++ |
| 13 | —$CH_3$ | 1H-indazol-5-yl | —NH— | 4-fluorophenyl | ++++ | ++++ |
| 14 | —$CH_3$ | 8-quinolyl | —NH— | 4-methylphenyl | +++ | +++ |
| 15 | —$CH_3$ | 6-quinolyl | —NH— | 4-methylphenyl | +++ | +++ |
| 16 | —$CH_3$ | 4-indolyl | —NH— | 4-methylphenyl | ++++ | ++++ |
| 17 | —$CH_3$ | 5-indolyl | —NH— | 4-methylphenyl | +++++ | +++++ |
| 18 | —$CH_3$ | 5-indolyl | —NH— | 4-bromophenyl | ++++ | ++++ |
| 19 | —$CH_3$ | 1H-pyrrolo[2,3-b]pyridin-5-yl | —NH— | 4-methylphenyl | ++++ | ++++ |
| 20 | —$CH_3$ | 4-methoxyphenyl | —NH— | 4-methylphenyl | + | – |
| 21 | —$CH_3$ | 5-indolyl | —NH— | phenyl | +++++ | ++++ |
| 22 | —$CH_3$ | 1H-pyrrolo[2,3-b]pyridin-5-yl | —NH— | phenyl | +++++ | +++++ |
| 23 | —$CH_3$ | 6-quinolyl | —NH— | phenyl | – | + |
| 24 | —$CH_3$ | 6-indolyl | —NH— | 4-fluorophenyl | ++ | ++ |
| 25 | —$CH_3$ | 6-indolyl | —NH— | phenyl | ++ | ++ |
| 26 | —$CH_3$ | 5-indolyl | —NH— | 4-carbomethoxyphenyl | ++++ | ++++ |
| 27 | —$CH_3$ | 2-oxoindolin-5-yl | —NH— | 4-methylphenyl | ++ | + |
| 28 | —$CH_3$ | 6-indolyl | —NH— | 4-methylphenyl | +++ | +++ |
| 29 | —$CH_3$ | 5-indolyl | —NH— | 4-methoxyphenyl | +++++ | +++++ |
| 30 | —$CH_3$ | 4-indolyl | —NH— | 4-methoxyphenyl | ++++ | ++++ |
| 31 | —$CH_3$ | 4-indolyl | —NH— | 4-chlorophenyl | ++++ | ++++ |
| 32 | —$CH_3$ | 1H-pyrrolo[2,3-b]pyridin-5-yl | —NH— | 4-chlorophenyl | ++++ | ++++ |
| 33 | —$CH_3$ | 5-indolyl | —NH— | 3-chloro-4-fluorophenyl | +++++ | ++++ |
| 34 | —$CH_3$ | 4-indolyl | —NH— | 3-chloro-4-fluorophenyl | + | + |
| 35 | —$CH_3$ | 1H-pyrrolo[2,3-b]pyridin-5-yl | —NH— | 3-chloro-4-fluorophenyl | +++++ | +++++ |
| 36 | —$CH_3$ | 2-oxoindolin-5-yl | —NH— | 3-chloro-4-fluorophenyl | +++ | +++ |
| 37 | —$CH_3$ | 5-indolyl | —NH— | 4-carboxyphenyl | +++ | +++ |
| 38 | —$CH_3$ | 1H-indazol-5-yl | —NH— | 3-chloro-4-fluorophenyl | +++ | +++ |
| 39 | —$CH_3$ | 5-indolyl | —NH— | 2,4-difluorophenyl | +++++ | +++++ |
| 40 | —$CH_3$ | 1H-indazol-5-yl | —NH— | 2,4-difluorophenyl | +++ | +++ |
| 41 | —$CH_3$ | 2-oxoindolin-5-yl | —NH— | 2,4-difluorophenyl | + | + |
| 42 | —$CH_3$ | 2-morpholinoethyl | —NH— | 2,4-difluorophenyl | + | + |
| 43 | —$CH_3$ | 5-indolyl | —NH— | 4-hydroxyphenyl | +++++ | +++++ |
| 44 | —$CH_2CH_2CH_3$ | 6-indolyl | —NH— | phenyl | ++++ | ++++ |
| 45 | —$CH_2CH_2CH_3$ | 4-indolyl | —NH— | phenyl | ++++ | +++ |
| 46 | —H | 5-indolyl | —NH— | 3-chloro-4-fluorophenyl | +++ | + |
| 47 | —$CH_2CH_2CH_3$ | 5-indolyl | —NH— | phenyl | +++++ | ++++ |
| 48 | —$CH_2CH_2CH_3$ | —$CH_3$ | —S— | phenyl | + | – |
| 50 | cyclohexyl | 4-(4-methylpiperazin-1-yl)phenyl | —NH— | 4-chlorophenyl | ++++ | ++++ |
| 51 | cyclohexyl | 5-indolyl | —NH— | 4-chlorophenyl | +++ | ++ |
| 52 | cyclohexyl | 4-morpholinophenyl | —NH— | 4-chlorophenyl | ++++ | +++ |
| 53 | cyclohexyl | 4-indolyl | —NH— | 4-chlorophenyl | +++ | – |
| 54 | —$CH_2CH_3$ | 5-indolyl | —NH— | phenyl | +++++ | ++++ |
| 55 | cyclopentyl | 5-indolyl | —NH— | phenyl | ++++ | ++++ |
| 56 | cyclopentyl | 4-methoxyphenyl | —NH— | phenyl | ++++ | ++ |
| 57 | cyclopentyl | 4-(5-(trifluoromethyl)pyridin-2-yl)piperazin-1-yl | — | phenyl | + | ++ |
| 58 | cyclopentyl | 4-(4-methylpiperazin-1-yl)phenyl | —NH— | 4-chlorophenyl | ++++ | +++ |
| 59 | cyclopentyl | —$CH_3$ | —SO— | 4-chlorophenyl | ++++ | +++ |
| 60 | cyclopentyl | —$CH_3$ | —S— | 4-chlorophenyl | + | + |
| 61 | cyclopentyl | cyclopentyl | —NH— | phenyl | – | – |
| 62 | cyclopentyl | 3,4,5-trimethoxyphenyl | —NH— | phenyl | ++++ | ++++ |
| 63 | cyclopentyl | 4-morpholinophenyl | —NH— | phenyl | +++ | +++ |
| 64 | cyclopentyl | 4-(4-methylpiperazin-1-yl)phenyl | —NH— | phenyl | ++++ | +++++ |
| 65 | cyclopentyl | 5-(4-tert-butoxycarbonylpiperazin-1-yl)pyridin-2-yl | —NH— | phenyl | +++ | – |
| 66 | cyclopentyl | —$CH_3$ | —SO— | phenyl | +++ | + |
| 67 | cyclopentyl | —$CH_3$ | —S— | phenyl | + | + |
| 68 | —H | —$CH_3$ | —S— | phenyl | – | – |

Potencies ($IC_{50}$) of the compounds in the K-562 and DU 145 assays are indicated as follows:
–: greater than 100 μM;
+: >50 to 100 μM;
++: >25 to 50 μM;
+++: >10 to 25 μM;
++++: >1 to 10 μM;
+++++: ≤1 μM Biology Example 2

Effect of 2-(1H-indol-5-ylamino)-6-(2,4-difluorophenylsulfonyl)-8-methylpyrido[2,3-d]pyrimidin-7(8H)-one on Tumor Cell Lines The compound of Example 39, 2-(1H-indol-5-ylamino)-6-(2,4-difluorophenylsulfonyl)-8-methylpyrido[2,3-d]pyrimidin-7(8H)-one, was further tested for effect against various tumor cell lines as follows. The assay is described by Latham et al., *Oncogene* 12:827-837 (1996). Tumor cells were plated in 96-well dishes at a cell density of $2.5\times10^4$ cells well. The plated cells were treated 24 hours later with the Example 39 compound dissolved in DMSO at multiple concentrations ranging from 0.01 μM to 100 μM. The plates were examined 96 hours later (except for MOLT 4 and U266B1) under an inverted microscope, Olympus CK-2 using an 10× objective, and compound activity was noted by physical observation. MOLT 4 and U266B1 were examined after 120 hours. When necessary, the total number of viable cells was determined by trypsinizing the wells and counting the number of viable cells, as determined by trypan blue exclusion, using a hemacytometer. The results are shown in Table 3. $IC_{50}$ values represent the average of 3 separate experiments.

TABLE 3

Antitumor Effect of 2-(1H-indol-5-ylamino)-6-(2,4-difluorophenylsulfonyl)-8-methylpyrido[2,3-d]pyrimidin-7(8H)-one

| Cell Line | Tumor Type | $IC_{50}$ (μM) |
|---|---|---|
| DU145 | Prostate cancer (androgen independent) | 0.06 |
| NAMALWA | Burkitt's Lymphoma (EBV+, SKMRV+) | 0.14 |
| K562 | Chronic Myelogenous Leukemia; Bcr-Abl (Flt3 Negative) | 0.065 |
| HL60 | Acute Lymphocytic Leukemia; Promyelocytic (Flt3 Negative) | 0.13 |
| CEM | T-Cell Acute Lymphoblastic Leukemia | 0.045 |
| Z138C | Mantle Cell Lymphoma | 0.06 |
| GRANTA 519C | Mantle Cell Lymphoma | 0.065 |
| DAUDI | Burkitt's Lymphoma | 0.075 |
| *MOLT 4 | T-Cell Acute Lymphoblastic Leukemia | 0.06 |
| *U266B1 | Multiple Myeloma | 0.14 |

*One hundred twenty hour incubation

Biology Example 3

Effect of 2-(1H-indol-5-ylamino)-6-(2,4-difluorophenylsulfonyl)-8-methylpyrido[2,3-d]pyrimidin-7(8H)-one on Tumor Cell Lines The compound of Example 39, 2-(1H-indol-5-ylamino)-6-(2,4-difluorophenylsulfonyl)-8-methylpyrido[2,3-d]pyrimidin-7(8H)-one, was tested for effect against various tumor cell lines as follows. Cells ($1\times10^5$) were plated into 6-well dishes and 24 h later test compound was added at five different concentrations over a 2 log dilution (1-100 μM). The total number of viable cells was determined after 96 h of continuous treatment by staining with trypan blue and counting the number of non-staining cells (viable) remaining in each well using a hemacytometer. The percentage of viable cells remaining was calculated as follows: # viable cells (compound treated)/# viable cells (DMSO treated)*100. The $GI_{50}$ (the concentration of drug resulting in 50% net loss of growth inhibition) was determined. The results are set forth in Table 4.

TABLE 4

Antitumor Effect of 2-(1H-indol-5-ylamino)-6-(2,4-difluorophenylsulfonyl)-8-methylpyrido[2,3-d]pyrimidin-7(8H)-one

| Cell Line | Tumor Type | $GI_{50}$ (μM) |
|---|---|---|
| K562 | Chronic Myelogenous Leukemia | 0.075 |
| DU145 | Prostate | 0.075 |
| BT474 | Breast (Erbb2+) | 0.1 |
| MCF7 | Breast (Er+) | 0.075 |
| GRANTA-519 | Mantle Cell Lymphoma | 0.04 |
| SK-OV-3 | Ovarian | 0.075 |
| U87 | Glioblastoma | 0.2 |
| MIA-Pa-Ca-2 | Pancreatic | 0.075 |
| COLO-205 | Colon | 0.075 |
| HELA | Cervical | 0.05 |
| A549 | Non-Small Cell Lung Carcinoma | 0.075 |
| H1975 | Non-Small Cell Lung Carcinoma | 0.075 |
| SK-MEL-28 | Melanoma | 0.2 |
| RAJI | B-Cell | 0.05 |
| U2OS | Osteosarcoma | 0.05 |
| JURKAT | T-Cell | 0.025 |
| HFL | Normal | >5.0 |

Biology Example 4

Kinase Profiling of 2-(1H-indol-5-ylamino)-6-(2,4-difluorophenylsulfonyl)-8-methylpyrido[2,3-d]pyrimidin-7(8H)-one The compound of Example 39, 2-(1H-indol-5-ylamino)-6-(2,4-difluorophenylsulfonyl)-8-methylpyrido[2,3-d]pyrimidin-7(8H)-one, was subjected to a kinase inhibition assay for the kinases indicated in Table 5, below. Compounds were tested in 5 dose IC50 mode with 10-fold serial dilution starting at 10 μM. Staurosporine, a known protein kinase inhibitor, was tested in 5-dose IC50 mode with 3-fold serial dilution starting at 20 μM. Reactions were carried out in 10 μM ATP. The results are shown in Table 5. The results show that the compound of Example 39 is a kinase inhibitor highly selective for the kinase Plk2.

TABLE 5

Kinase Profiling of 2-(1H-indol-5-ylamino)-6-(2,4-difluorophenylsulfonyl)-8-methylpyrido[2,3-d]pyrimidin-7(8H)-one

| Kinase | Ex. 39 Compound $IC_{50}$ (nM) | Staurosporine $IC_{50}$ (nM) |
|---|---|---|
| PLK2 | 201 | 813 |
| WNK2 | 2785.00 | 8086.00 |
| RSK1 | 4253.00 | 0.19 |
| c-Kit (V560G) | 6148.00 | 0.18 |
| PLK1 | 7818.00 | 3673.00 |
| LCK | 8062.00 | 2.21 |
| FLT3 (D835Y) | 8847.00 | 0.32 |
| FGFR3 | 8998.00 | 15.59 |
| PIM3 | 9900.00 | 0.57 |
| ABL1 | >10000 | 438.10 |
| ABL1 (E255K) | >10000 | 384.50 |
| ABL1 (M351T) | >10000 | 62.16 |
| ABL1 (Q252H) | >10000 | 142.50 |
| ABL1 (T315I) | >10000 | 37.32 |
| ABL1 (Y253F) | >10000 | 183.50 |
| BLK | >10000 | 7.40 |
| c-Src | >10000 | 4.01 |
| c-Src (T341M) | >10000 | 3.64 |
| CAMKIIg | >10000 | 0.70 |
| CDK6/cyclinD3 | >10000 | 242.60 |
| CK1epsilon | >10000 | Not done |
| FGFR1 | >10000 | 8.00 |
| FLT3 | >10000 | 4.66 |
| JAK1 | >10000 | 1.70 |

TABLE 5-continued

Kinase Profiling of 2-(1H-indol-5-ylamino)-6-(2,4-difluorophenylsulfonyl)-8-methylpyrido[2,3-d]pyrimidin-7(8H)-one

| Kinase | Ex. 39 Compound $IC_{50}$ (nM) | Staurosporine $IC_{50}$ (nM) |
|---|---|---|
| JAK2 | >10000 | 0.55 |
| KDR/VEGFR2 | >10000 | 39.49 |
| LYN B | >10000 | 24.32 |
| NEK1 | >10000 | 150.40 |
| PBK/TOPK | >10000 | 432.60 |
| PKCzeta | >10000 | 204.20 |
| RON/MST1R | >10000 | 1791.00 |
| TIE2/TEK | >10000 | 719.80 |
| ZAP70 | >10000 | 87.49 |

Biology Example 5

Figure 1A:
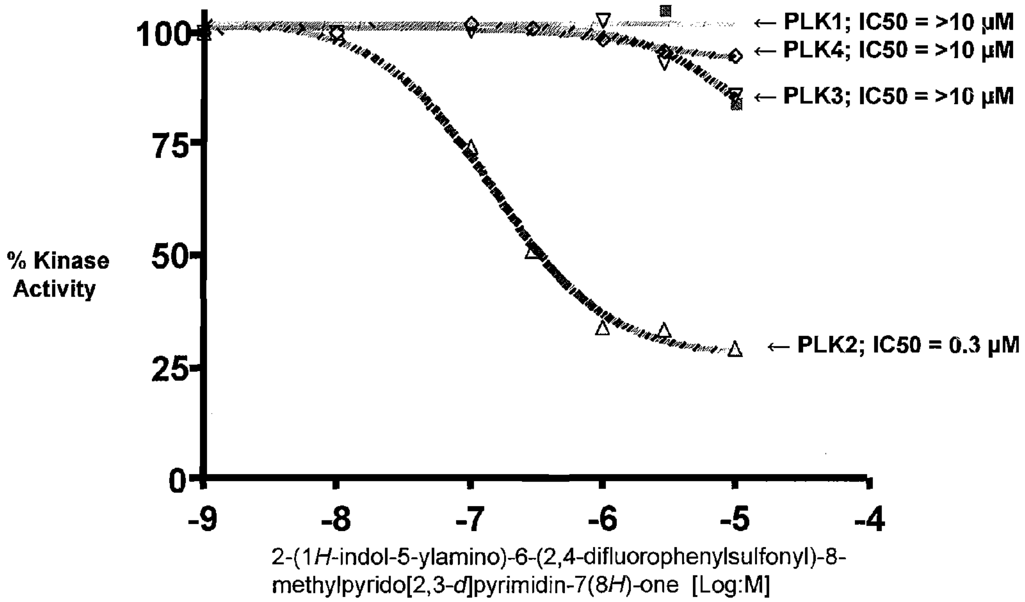
FIGS. 1A and 1B represent the results of a kinase profiling assays of the Example compound, 2-(1H-indol-5-ylamino)-6-(2,4-difluorophenylsulfonyl)-8-methylpyrido[2,3-d]pyrimidin-7(8H)-one (FIG. 1A), and the known kinase inhibitor wortmanin (FIG. 1B). Ten ng of recombinant Plk1, Plk2, Plk3 or Plk4 kinase were incubated with the indicated concentrations of compound for 30 minutes at room temperature. Kinase reactions were started by the addition of substrate mix (5 μM ATP, 10 μCi $\gamma^{32}$P-ATP, 1 μg α-casein, 10 mM $MgCl_2$) for 15 minutes at 30° C. Reactions were stopped by 3% phosphoric acid, spotted on PE30 filtermat, washed, dried and subjected to scintillation counting. Data is plotted (after background subtraction) using GraphPad Prism4 software as a non-linear regression plot with variable slope to obtain $IC_{50}$ values.
Figure 1B:
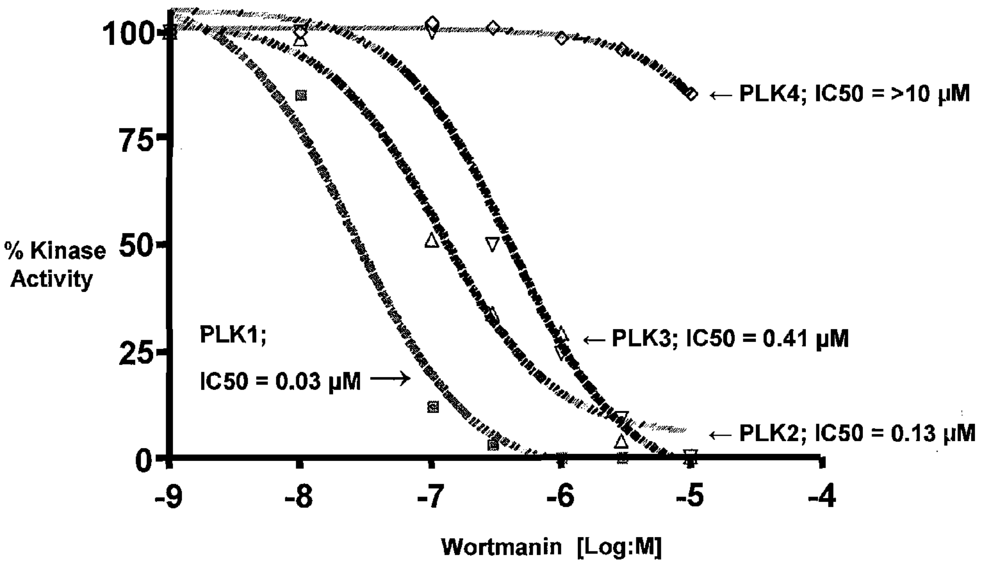

Plk Kinase Inhibition by 2-(1H-indol-5-ylamino)-6-(2,4-difluorophenylsulfonyl)-8-methylpyrido[2,3-d]pyrimidin-7(8H)-one The compound of Example 39, 2-(1H-indol-5-ylamino)-6-(2,4-di fluorophenyl sulfonyl)-8-methylpyrido[2,3-d]pyrimidin-7(8H)-one, was subjected to the following Plk kinase (Plk1, Plk2, Plk3 or Plk4) inhibition assay demonstrating selectivity of the compound for Plk2. Ten ng of recombinant Plk kinase was incubated with the indicated concentrations of Example 39 compound or wortmanin (a Plk kinase inhibitor) for 30 minutes at room temperature. Kinase reactions were started by the addition of substrate mix (5 μM ATP, 10 μCi $\gamma^{32}$P-ATP, 1 μg α-casein, 10 mM $MgCl_2$) for 15 minutes at 30° C. Reactions were stopped by 3% phosphoric acid, spotted on PE30 filtermat, washed, dried and subjected to scintillation counting. Data is plotted (after background subtraction) using GraphPad Prism4 software as a non-linear regression plot with variable slope to obtain $IC_{50}$ values. The results are shown in FIG. 1A (2-(1H-indol-5-ylamino)-6-(2,4-difluorophenylsulfonyl)-8-methylpyrido[2,3-d]pyrimidin-7(8H)-one) and FIG. 1B (wortmanin).

The results show that the Example 39 compound is a potent inhibitor of PLK-2, with little or no inhibitory activity against PLK-1, PLK-3 and PLK-4. Wortmanin, a positive control, exhibited nanomolar inhibitory activity against Plk-1, 2 and 3.

Biology Example 6

Establishment of Direct Interaction Between Plk2 and 2-(1H-indol-5-ylamino)-6-(2,4-difluorophenylsulfonyl)-8-methylpyrido[2,3-d]pyrimidin-7(8H)-one The direct interaction of the Example 39 compound with Plk2 was confirmed by affinity analysis using a biotinylated form of the compound. Increasing concentrations of a biotinylated form of the compound were incubated for two hours with U2OS lysates (0.6 mg/ml) derived from the U2OS cell line. The incubation concentrations of biotinylated Example 39 compound are given in FIG. 2. Streptavidin-conjugated agarose beads were utilized to pull down the biotinylated compound in complex with its interacting proteins. Precleared streptavidin beads were added to each reaction mixture and incubated overnight at 4° C. The beads were washed and blotted with SDS-PAGE loading buffer and run on a 10% acrylamide denaturing gel. For competition assays, the biotinylated Example 39 compound was combined with increasing concentrations of free Example 39 compound. Western blotting was performed using an anti-Plk2 antibody.

The results of the study, shown in FIG. 2 demonstrated that Plk2 was able to form a complex with the Example 39 compound-biotin complex is a dose-dependent manner. This interaction could be readily competed out by the free (unbiotinylated) Example 39 compound, also in a dose-dependent manner.

Biology Example 7

Induction of Apoptosis in Tumor Cell by 2-(1H-indol-5-ylamino)-6-(2,4-difluorophenylsulfonyl)-8-methylpyrido[2,3-d]pyrimidin-7(8H)-one A. The dose-dependent induction of apoptosis of U2OS osteosarcoma cells by the Example 39 compound was demonstrated as follows. U2OS cells were treated with increasing concentrations of the Example 39 compound for 24 hours. Cell viability was measured by incubating cells with Cell Titer Blue reagent (Promega) at 37° C. for 3 hours under 5% $CO_2$. Thereafter the cells were incubated with Caspase Glo reagent (Promega) for 1 hour at room temperature to assay induction of Caspase 3/7 activity.

The results of the experiment in FIG. 3 show that the compound of Example 39 induces apoptosis of U2OS osteosarcoma cells in a dose-dependent fashion, and results in an induction of caspase 3/7 activity in a dose dependant manner. A concomitant dose-dependent decrease in cell viability was observed in the same set of cells, measured by the reduction of the fluorogenic substrate (Cell Titer Blue).

B. In a further experiment, U2OS osteosarcoma cells were plated onto coverslips and treated for 24 hrs with DMSO or 1 μM of the Example 39 compound. The cells were fixed in 4% paraformaldehyde and stained with anti-alpha tubulin antibodies conjugated with FITC followed by 5 μg/ml DAN staining. The coverslips were visualized by fluorescent microscopy using an Olympus microscope at 100× magnification equipped with the Insight digital camera system. Multiple spindle formation was observed in the Example 39 compound-treated U2OS cells, but not DMSO-treated cells. At 1 uM concentration, greater than 95% of the treated cells were mitotically arrested with multipolar spindles, indicating mitotic catastrophe.

Biology Example 8

Safety Profile of 2-(1H-indol-5-ylamino)-6-(2,4-difluorophenylsulfonyl)-8-methylpyrido[2,3-d]pyrimidin-7(8H)-one A. The following toxicity study was carried out comparing the mammalian toxicity of the Example 39 compound to BI-2536 (Boehringer Ingelheim Pharma, Ingelheim, Germany), a Plk1 inhibitor presently in clinical trials. DMSO was used as a placebo. Three CD-1 female mice were used per group. Drugs were administered intraperitoneally at 100 mg/kg. Viability, signs of toxicity and body weight were monitored over the next 7 days. No signs of toxicity and 100% survival of mice injected with the Example 39 compound were observed, as well as with the placebo. No weight loss was observed for mice injected with the Example 39 compound and placebo. For the set injected with BI-2536, two mice died within 24 hours while the third mouse died within 72 hours, showing signs of toxicity from day 1 after injection. Comparative body weight studies could not be carried out for this compound due to the early death of animals. These observations agree with the known toxicity of BI-2536. In a separate experiment, CD-1 female mice were injected with 200 mg/kg of Example 39 compound and examined for signs of toxicity and survival. Following this treatment, 100% survival for >10 days after injection was observed. These studies suggest that although the BI-2536, a potent PLK1 inhibitor, causes toxicity in mice at 100 mg/kg dose, the Example 39 compound, which specifically inhibits PLK2, is very well tolerated in mammals.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

What is claimed is:

1. A compound of formula I, or a salt thereof:

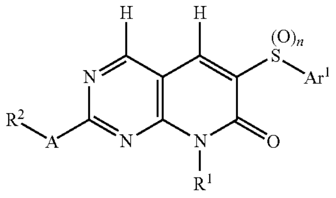

I wherein:
A is $S(O)_m$ or $NR^A$;
$R^1$ is selected from the group consisting of hydrogen, $(C_1-C_6)$alkyl, and $(C_3-C_7)$cycloalkyl;
$R^2$ is selected from the group consisting of $(C_1-C_6)$alkyl, $(C_3-C_7)$cycloalkyl, unsubstituted $—(CH_2)_r—(C_2-C_7)$heterocycle, substituted $—(CH_2)_r—(C_2-C_7)$heterocycle, unsubstituted $(C_6-C_{10})$aryl, substituted $(C_6-C_{10})$aryl, unsubstituted $(C_2-C_9)$heterocyclyl, and substituted $(C_2-C_9)$heterocyclyl; wherein the substituted $(C_6-C_{10})$aryl, substituted $—(CH_2)_r—(C_2-C_7)$heterocycle, and substituted $(C_2-C_9)$heterocyclyl groups are substituted with one or more substituents independently selected from the group consisting of $(C_1-C_6)$alkyl; $(C_2-C_6)$alkenyl; $(C_2-C_6)$alkynyl; halogen; $—C≡N$; $—NO_2$; $—C(=O)R^3$; $—C(=O)OR^3$; $—C(=NR^3)NR^3{}_2$; $—OR^3$; $—OC(=O)(C_1-C_6)$alkyl; $—OC(=O)O(C_1-C_6)$alkyl; $—OC(=O)NR^3{}_2$; $—NR^3{}_2$; $—NR^3C(=O)R^3$; $—NR^3C(=O)O(C_1-C_6)$alkyl; $—NR^3C(=O)NR^3{}_2$; $—NR^3SO_2R^3$; $—SR^3$; $—S(O)R^3$; $—SO_2R^3$; $—OSO_2(C_1-C_6)$alkyl; $—SO_2NR^3{}_2$; $(C_2-C_9)$heterocyclyl; $(C_1-C_3)$perfluoroalkyl; $—(C_2-C_6)$alkylene-$OR^3$; $—O(C_2-C_6)$alkylene-$N((C_1-C_6)$alkyl$)_2$; $—P(=O)(OR^4)_2$; $—OP(=O)(OR^4)_2$, 4-methylpiperazin-1-yl; 4-BOC-piperazin-1-yl; and 4-acetylpiperazin-1-yl;
m is 0, 1, or 2;
n is 1 or 2;
r is 1, 2, 3, or 4;
$R^A$ is selected from the group consisting of hydrogen and $(C_1-C_6)$alkyl, wherein when $R^A$ and $R^2$ are bonded to the same nitrogen atom, $R^A$ and $R^2$ may combine to form a heterocycle or substituted heterocycle, wherein the substituted heterocycle is substituted with one or more substituents selected from the group consisting of $(C_1-C_6)$alkyl$(C_2-C_6)$alkenyl;
$(C_2-C_6)$alkynyl; halogen; $—C≡N$; $—NO_2$; $—C(=O)R^3$; $—C(=O)OR^3$; $—C(=O)NR^3{}_2$; $—C(=NR^3)NR^3{}_2$; $—OR^3$; $—OC(=O)(C_1-C_6)$alkyl; $—OC(=O)O(C_1-C_6)$alkyl; $—OC(=O)NR^3{}_2$; $—NR^3{}_2$; $—NR^3C(=O)R^3$; $—NR^3C(=O)O(C_1-C_6)$alkyl; $—NR^3C(=O)NR^3{}_2$; $—NR^3SO_2R^3$; $—SR^3$; $—S(O)R^3$; $—SO_2R^3$; $—OSO_2(C_1-C_6)$alkyl; $—SO_2NR^3{}_2$; $(C_1-C_3)$perfluoroalkyl; $—(C_2-C_6)$alkylene-$OR^3$; $—O(C_2-C_6)$alkylene-$N((C_1-C_6)$alkyl$)_2$; $—P(=O)(OR^4)_2$; $—OP(=O)(OR^4)_2$; pyridyl; 3-trifluoromethylpyridyl; and 4-trifluoromethylpyridyl;
$Ar^1$ is selected from the group consisting of unsubstituted $(C_6-C_{10})$aryl and substituted $(C_6-C_{10})$aryl, wherein the substituted $(C_6-C_{10})$aryl groups are substituted with one to five substituents independently selected from the group consisting of $(C_1-C_6)$alkyl, $(C_2-C_6)$alkenyl;
$(C_2-C_6)$alkynyl; halogen; $—C≡N$; $—NO_2$; $—C(=O)R^3$; $—C(=O)OR^3$; $—C(=O)NR^3{}_2$; $—C(=NR^3)NR^3{}_2$; $—OR^3$; $—OC(=O)(C_1-C_6)$alkyl; $—OC(=O)O(C_1-C_6)$alkyl; $—OC(=O)NR^3{}_2$; $—NR^3{}_2$; $—NR^3C(=O)R^3$; $—NR^3C(=O)O(C_1-C_6)$alkyl; $—NR^3C(=O)NR^3{}_2$; $—NR^3SO_2R^3$; $—SR^3$; $—S(O)R^3$; $—SO_2R^3$; $—OSO_2(C_1-C_6)$alkyl; $—SO_2NR^3{}_2$; $(C_1-C_3)$perfluoroalkyl; $—(C_2-C_6)$alkylene-$OR^3$; $—O(C_2-C_6)$alkylene-$N((C_1-C_6)$alkyl$)_2$; $—P(=O)(OR^4)_2$; and $—OP(=O)(OR^4)_2$;
each $R^3$ is independently selected from the group consisting of hydrogen and $(C_1-C_6)$alkyl; and
each $R^4$ is independently selected from the group consisting of hydrogen and $(C_1-C_6)$alkyl.

2. A compound according to claim 1, or a salt thereof, wherein A is $S(O)_m$.

3. A compound according to claim 2, or a salt thereof, wherein $R^2$ is $(C_1-C_6)$alkyl.

4. A compound according to claim 3, or a salt thereof, wherein $R^1$ is $(C_1-C_6)$alkyl or $(C_3-C_7)$cycloalkyl.

5. A compound according to claim 4, or a salt thereof, wherein m is 0 or 1.

6. A compound according to claim 5 selected from the group consisting of: 2-(methylsulfanyl)-6-(phenylsulfonyl)-8-propylpyrido[2,3-d]pyrimidin-7(8H)-one; 8-cyclopentyl-2-(methylsulfanyl)-6-(phenylsulfonyl)pyrido[2,3-d]pyrimidin-7(8H)-one; 8-cyclopentyl-2-(methylsulfinyl)-6-(phenylsulfonyl)pyrido[2,3-d]pyrimidin-7(8H)-one; 6-(4-chlorophenylsulfonyl)-8-cyclopentyl-2-(methylsulfanyl) pyrido[2,3-d]pyrimidin-7(8H)-one; and 6-(4-chlorophenylsulfonyl)-8-cyclopentyl-2-(methylsulfinyl) pyrido[2,3-d]pyrimidin-7(8H)-one.

7. A compound according to claim 5 selected from the group consisting of 6-(2,4-difluorophenylsulfonyl)-8-methyl-2-(methylsulfanyl)pyrido[2,3-d]pyrimidin-7(8H)-one and 6-(2,4-difluorophenylsulfonyl)-8-methyl-2-(methylsulfinyl)pyrido[2,3-d]pyrimidin-7(8H)-one.

8. A compound according to claim 2, or a salt thereof, wherein $R^2$ is unsubstituted $(C_6-C_{10})$aryl.

9. A compound according to claim 8, or a salt thereof, wherein $R^1$ is $(C_1-C_6)$alkyl or $(C_3-C_7)$cycloalkyl.

10. A compound according to claim 9, or a salt thereof, wherein m is 0 or 1.

11. The compound according to claim 10 which is 6-(phenylsulfonyl)-2-(phenylsulfanyl)-8-propylpyrido[2,3-d]pyrimidin-7(8H)-one.

12. A compound according to claim 1, or a salt thereof, wherein A is $NR^A$.

13. A compound according to claim 12, or a salt thereof, wherein $R^1$ is $(C_3-C_7)$cycloalkyl.

14. A compound according to claim 13 selected from the group consisting of: 2-(5-(4-tert-butoxycarbonylpiperazin-1-yl)pyridin-2-ylamino)-8-cyclopentyl-6-(phenylsulfonyl)pyrido[2,3-d]pyrimidin-7(8H)-one; 2-(4-(4-methylpiperazin-1-yl)phenylamino)-8-cyclopentyl-6-(phenylsulfonyl)pyrido

[2,3-d]pyrimidin-7(8H)-one; 2-(4-morpholinophenylamino)-8-cyclopentyl-6-(phenylsulfonyl)pyrido[2,3-d]pyrimidin-7(8H)-one; 2-(3,4,5-trimethoxyphenylamino)-8-cyclopentyl-6-(phenylsulfonyl)pyrido[2,3-d]pyrimidin-7(8H)-one; 2-(4-(4-methylpiperazin-1-yl)phenylamino)-6-(4-chlorophenylsulfonyl)-8-cyclopentylpyrido[2,3-d]pyrimidin-7(8H)-one; 8-cyclopentyl-2-(4-(5-(trifluoromethyl)pyridin-2-yl)piperazin-1-yl)-6-(phenylsulfonyl)pyrido[2,3-d]pyrimidin-7(8H)-one; 2-(4-methoxyphenylamino)-8-cyclopentyl-6-(phenylsulfonyl)pyrido[2,3-d]pyrimidin-7(8H)-one; 6-(4-chlorophenylsulfonyl)-2-(4-morpholinophenylamino)-8-cyclohexylpyrido[2,3-d]pyrimidin-7(8H)-one; 2-(4-(4-methylpiperazin-1-yl)phenylamino)-6-(4-chlorophenylsulfonyl)-8-cyclohexylpyrido[2,3-d]pyrimidin-7(8H)-one; or salt thereof.

15. A compound according to claim 12, or a salt thereof, wherein $R^1$ is $(C_1\text{-}C_6)$alkyl.

16. A compound according to claim 15 selected from the group consisting of: 2-(4-chlorophenylamino)-6-(4-chlorophenylsulfonyl)-8-methylpyrido[2,3-d]pyrimidin-7(8H)-one; 6-(4-chlorophenylsulfonyl)-2-(4-methoxyphenylamino)-8-methylpyrido[2,3-d]pyrimidin-7(8H)-one; 6-(4-chlorophenylsulfonyl)-8-methyl-2-(quinolin-3-ylamino)pyrido[2,3-d]pyrimidin-7(8H)-one; 2-(3-morpholinopropylamino)-6-(4-chlorophenylsulfonyl)-8-methylpyrido[2,3-d]pyrimidin-7(8H)-one; 6-(4-chlorophenylsulfonyl)-2-(4-acetylpiperazin-1-yl)-8-methylpyrido[2,3-d]pyrimidin-7(8H)-one; 2-(2-(4-methylpiperazin-1-yl)ethylamino)-6-(4-chlorophenylsulfonyl)-8-methylpyrido[2,3-d]pyrimidin-7(8H)-one; 8-methyl-2-(quinolin-8-ylamino)-6-tosylpyrido[2,3-d]pyrimidin-7(8H)-one; 8-methyl-2-(quinolin-5-ylamino)-6-tosylpyrido[2,3-d]pyrimidin-7(8H)-one; 2-(4-methoxyphenylamino)-8-methyl-6-tosylpyrido[2,3-d]pyrimidin-7(8H)-one; 8-methyl-6-(phenylsulfonyl)-2-(quinolin-6-ylamino)pyrido[2,3-d]pyrimidin-7(8H)-one; 6-(2,4-difluorophenylsulfonyl)-2-(2-morpholinoethylamino)-8-methylpyrido[2,3-d]pyrimidin-7(8H)-one; or salt thereof.

17. A compound of claim 1 having the formula II, or a salt thereof:

II

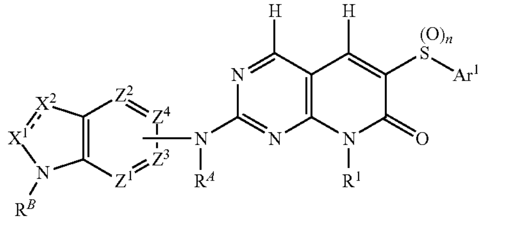

wherein:

$X^1$ is selected from the group consisting of nitrogen, $CR^5$, and C(=O);

$X^2$ is nitrogen or $CR^5$;

$Z^1$ is nitrogen or $CR^5$;

$Z^2$ is nitrogen or $CR^5$;

$Z^3$ is nitrogen or $CR^5$;

$Z^4$ is nitrogen or $CR^5$;

$R^A$ is selected from the group consisting of hydrogen and $(C_1\text{-}C_6)$alkyl;

$R^B$ is selected from the group consisting of hydrogen, $(C_1\text{-}C_6)$alkyl, $(C_1\text{-}C_6)$acyl, unsubstituted —C(=O)—$(C_6\text{-}C_{10})$aryl, substituted —C(=O)—$(C_6\text{-}C_{10})$aryl, unsubstituted —$(CH_2)_q$—$(C_6\text{-}C_{10})$aryl, substituted —$(CH_2)_q$—$(C_6\text{-}C_{10})$aryl, and —C(=O)O—$(C_1\text{-}C_6)$alkyl; wherein the substituted —C(=O)—$(C_6\text{-}C_{10})$aryl and substituted —$(CH_2)_q$—$(C_6\text{-}C_{10})$aryl groups are substituted with one or more substituents independently selected from the group consisting of $(C_1\text{-}C_6)$alkyl; $(C_2\text{-}C_6)$alkenyl; $(C_2\text{-}C_6)$alkynyl; halogen; —C≡N; —$NO_2$; —C(=O)$R^6$; —C(=O)$OR^6$; —C(=O)$NR^6_2$; —C(=$NR^6$)$NR^6_2$; —$OR^6$; —OC(=O)$(C_1\text{-}C_6)$alkyl; —OC(=O)O$(C_1\text{-}C_6)$alkyl; —OC(=O)$NR^6_2$; —$NR^6_2$; —$NR^6$C(=O)$R^6$; —$NR^6$C(=O)O$(C_1\text{-}C_6)$alkyl; —$NR^6$C(=O)$NR^6_2$; —$NR^6SO_2R^6$; —$SR^6$; —S(O)$R^6$; —$S_2R^6$; —$OSO_2(C_1\text{-}C_6)$alkyl; —$SO_2NR^6_2$; $(C_2\text{-}C_9)$heterocyclyl; $(C_1\text{-}C_3)$perfluoroalkyl; —$(C_2\text{-}C_6)$alkylene-$OR^6$; —$O(C_2\text{-}C_6)$alkylene-N($(C_1\text{-}C_6)$alkyl$)_2$; —P(=O)$(OR^7)_2$; and —OP(=O)$(OR^7)_2$;

q is 1, 2, 3, or 4;

each $R^5$ is independently selected from the group consisting of hydrogen;

$(C_1\text{-}C_6)$alkyl; $(C_2\text{-}C_6)$alkenyl; $(C_2\text{-}C_6)$alkynyl; halogen; —C≡N; —$NO_2$; —C(=O)$R^3$; —C(=O)$OR^3$; —C(=O)$NR^3_2$; —C(=$NR^3$)$NR^3_2$; —$OR^3$; —OC(=O)$(C_1\text{-}C_6)$alkyl; —OC(=O)O$(C_1\text{-}C_6)$alkyl; —OC(=O)$NR^3_2$; —$NR^3_2$; —$NR^3$C(=O)$R^3$; —$NR^3$C(=O)O$(C_1\text{-}C_6)$alkyl; —$NR^3$C(=O)$NR^3_2$; —$NR^3SO_2R^3$; —$SR^3$; —S(O)$R^3$; —$SO_2R^3$; —$OSO_2(C_1\text{-}C_6)$alkyl; —$SO_2NR^3_2$; $(C_1\text{-}C_3)$perfluoroalkyl; —$(C_2\text{-}C_6)$alkylene-$OR^3$; —$O(C_2\text{-}C_6)$alkylene-N($(C_1\text{-}C_6)$alkyl$)_2$; —P(=O)$(OR^4)_2$; and —OP(=O)$(OR^4)_2$;

each $R^6$ is independently selected from the group consisting of hydrogen and $(C_1\text{-}C_6)$alkyl; and each $R^7$ is independently selected from the group consisting of hydrogen and $(C_1\text{-}C_6)$alkyl.

18. A compound according to claim 17, or a salt thereof, wherein $R^1$ is $(C_1\text{-}C_6)$alkyl or $(C_3\text{-}C_7)$cycloalkyl.

19. A compound according to claim 18, or a salt thereof, wherein $R^A$ is hydrogen.

20. A compound according to claim 19, or a salt thereof, wherein n is 2.

21. A compound of claim 17 having the formula III, or a salt thereof:

III

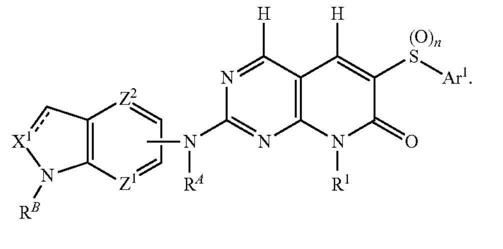

22. A compound according to claim 21, or a salt thereof, wherein $R^1$ is $(C_3\text{-}C_7)$cycloalkyl.

23. A compound according to claim 22, or a salt thereof, wherein $R^A$ is hydrogen.

24. A compound according to claim 23, or a salt thereof, wherein n is 2.

25. A compound according to claim 24 selected from the group consisting of: 2-(1H-indol-5-ylamino)-8-cyclopentyl-6-(phenylsulfonyl)pyrido[2,3-d]pyrimidin-7(8H)-one; and 2-(1H-indol-5-ylamino)-6-(4-chlorophenylsulfonyl)-8-cyclohexylpyrido[2,3-d]pyrimidin-7(8H)-one.

26. A compound according to claim 21, or a salt thereof, wherein $R^1$ is $(C_1\text{-}C_6)$alkyl.

27. A compound according to claim 26, or a salt thereof, wherein $R^A$ is hydrogen.

28. A compound according to claim 27, or a salt thereof, wherein n is 2.

29. A compound according to claim 28, or a salt thereof, wherein $X^1$ is selected from the group consisting of nitrogen and C(═O).

30. A compound according to claim 29 selected from the group consisting of: 2-(1H-indazol-5-ylamino)-6-(4-fluorophenylsulfonyl)-8-methylpyrido[2,3-d]pyrimidin-7(8H)-one; 2-(2-oxoindolin-5-ylamino)-8-methyl-6-tosylpyrido[2,3-d]pyrimidin-7(8H)-one; 2-(2-oxoindolin-5-ylamino)-6-(3-chloro-4-fluorophenylsulfonyl)-8-methylpyrido[2,3-d]pyrimidin-7(8H)-one; 2-(1H-indazol-5-ylamino)-6-(3-chloro-4-fluorophenylsulfonyl)-8-methylpyrido[2,3-d]pyrimidin-7(8H)-one; 2-(1H-indazol-5-ylamino)-6-(2,4-difluorophenylsulfonyl)-8-methylpyrido[2,3-d]pyrimidin-7(8H)-one; and 6-(2,4-difluorophenylsulfonyl)-2-(2-oxoindolin-5-ylamino)-8-methylpyrido[2,3-d]pyrimidin-7(8H)-one, or salt thereof.

31. A compound according to claim 28, or a salt thereof, wherein $X^1$ is CH, $Z^2$ is CH, and hashed bond (----) represents a carbon-carbon double bond.

32. A compound according to claim 31 selected from the group consisting of: 2-(1H-indol-5-ylamino)-6-(4-chlorophenylsulfonyl)-8-methylpyrido[2,3-d]pyrimidin-7(8H)-one; 2-(1H-indol-4-ylamino)-6-(4-fluorophenylsulfonyl)-8-methylpyrido[2,3-d]pyrimidin-7(8H)-one; 2-(1H-indol-5-ylamino)-6-(4-fluorophenylsulfonyl)-8-methylpyrido[2,3-d]pyrimidin-7(8H)-one; 2-(1H-pyrrolo[2,3-b]pyridin-5-ylamino)-6-(4-fluorophenylsulfonyl)-8-methylpyrido[2,3-d]pyrimidin-7(8H)-one; 2-(1H-indol-4-ylamino)-8-methyl-6-tosylpyrido[2,3-d]pyrimidin-7(8H)-one; 2-(1H-indol-5-ylamino)-8-methyl-6-tosylpyrido[2,3-d]pyrimidin-7(8H)-one; 2-(1H-indol-5-ylamino)-6-(4-bromophenylsulfonyl)-8-methylpyrido[2,3-d]pyrimidin-7(8H)-one; 2-(1H-pyrrolo[2,3-b]pyridin-5-ylamino)-8-methyl-6-tosylpyrido[2,3-d]pyrimidin-7(8H)-one; 2-(1H-indol-5-ylamino)-8-methyl-6-(phenylsulfonyl)pyrido[2,3-d]pyrimidin-7(8H)-one; 2-(1H-pyrrolo[2,3-b]pyridin-5-ylamino)-8-methyl-6-(phenylsulfonyl)pyrido[2,3-d]pyrimidin-7(8H)-one; 2-(1H-indol-6-ylamino)-6-(4-fluorophenylsulfonyl)-8-methylpyrido[2,3-d]pyrimidin-7(8H)-one; 2-(1H-indol-6-ylamino)-8-methyl-6-(phenylsulfonyl)pyrido[2,3-d]pyrimidin-7(8H)-one; methyl 4-(2-(1H-indol-5-ylamino)-7,8-dihydro-8-methyl-7-oxopyrido[2,3-d]pyrimidin-6-ylsulfonyl)benzoate; 2-(1H-indol-5-ylamino)-8-ethyl-6-(phenylsulfonyl)pyrido[2,3-d]pyrimidin-7(8H)-one; 2-(1H-indol-6-ylamino)-8-methyl-6-tosylpyrido[2,3-d]pyrimidin-7(8H)-one; 2-(1H-indol-5-ylamino)-6-(4-methoxyphenylsulfonyl)-8-methylpyrido[2,3-d]pyrimidin-7(8H)-one; 2-(1H-indol-4-ylamino)-6-(4-methoxyphenylsulfonyl)-8-methylpyrido[2,3-d]pyrimidin-7(8H)-one; 2-(1H-indol-5-ylamino)-6-(phenylsulfonyl)-8-propylpyrido[2,3-d]pyrimidin-7(8H)-one; 2-(1H-indol-4-ylamino)-6-(4-chlorophenylsulfonyl)-8-methylpyrido[2,3-d]pyrimidin-7(8H)-one; 2-(1H-pyrrolo[2,3-b]pyridin-5-ylamino)-6-(4-chlorophenylsulfonyl)-8-methylpyrido[2,3-d]pyrimidin-7(8H)-one; 2-(1H-indol-5-ylamino)-6-(3-chloro-4-fluorophenylsulfonyl)-8-methylpyrido[2,3-d]pyrimidin-7(8H)-one; 2-(1H-indol-4-ylamino)-6-(phenylsulfonyl)-8-propylpyrido[2,3-d]pyrimidin-7(8H)-one; 2-(1H-indol-6-ylamino)-6-(phenylsulfonyl)-8-propylpyrido[2,3-d]pyrimidin-7(8H)-one; 2-(1H-indol-4-ylamino)-6-(3-chloro-4-fluorophenylsulfonyl)-8-methylpyrido[2,3-d]pyrimidin-7(8H)-one; 2-(1H-pyrrolo[2,3-b]pyridin-5-ylamino)-6-(3-chloro-4-fluorophenylsulfonyl)-8-methylpyrido[2,3-d]pyrimidin-7(8H)-one; 2-(1H-indol-5-ylamino)-6-(4-hydroxyphenylsulfonyl)-8-methylpyrido[2,3-d]pyrimidin-7(8H)-one; 4-(2-(1H-indol-5-ylamino)-7,8-dihydro-8-methyl-7-oxopyrido[2,3-d]pyrimidin-6-ylsulfonyl)benzoic acid; or salt thereof.

33. The compound according to claim 31 which is 2-(1H-indol-5-ylamino)-6-(2,4-difluorophenylsulfonyl)-8-methylpyrido[2,3-d]pyrimidin-7(8H)-one, or salt thereof.

34. A compound according to claim 21, or a salt thereof, wherein $R^1$ is hydrogen.

35. The compound according to claim 34 which is 2-(1H-indol-5-ylamino)-6-(3-chloro-4-fluorophenylsulfonyl)pyrido[2,3-d]pyrimidin-7(8H)-one, or salt thereof.

36. An antibody conjugate of the formula I-L-Ab, or a salt thereof, wherein

I is a compound according to claim 1,

Ab is an antibody; and

-L- is a single bond or a linking group covalently linking said compound of formula I to said antibody.

37. An antibody conjugate of claim 36, or a salt thereof, wherein the antibody is a monoclonal antibody or a monospecific polyclonal antibody.

38. An antibody conjugate of claim 37, or a salt thereof, wherein the antibody is a tumor-specific antibody.

39. A pharmaceutical composition comprising a pharmaceutically acceptable carrier and a compound according to claim 1, or a pharmaceutically acceptable salt thereof.

40. A pharmaceutical composition according to claim 39 wherein the compound is 2-(1H-indol-5-ylamino)-6-(2,4-difluorophenylsulfonyl)-8-methylpyrido[2,3-d]pyrimidin-7(8H)-one, or pharmaceutically acceptable salt thereof.

41. A pharmaceutical composition comprising a pharmaceutically acceptable carrier and a compound according to claim 21, or a pharmaceutically acceptable salt thereof.

42. A pharmaceutical composition comprising a pharmaceutically acceptable carrier and an antibody conjugate according to claim 36, or a pharmaceutically acceptable salt thereof.

43. A method of treating an individual for a cancer selected from the group consisting of ovarian cancer, cervical cancer, breast cancer, prostate cancer, lung cancer, colorectal cancer, skin cancer, brain cancer, pancreatic cancer, osteosarcoma, multiple myeloma, leukemia and lymphoma, comprising administering to the individual an effective amount of at least one compound according to claim 1, or a pharmaceutically acceptable salt thereof.

44. The method according to claim 43 wherein the compound is 2-(1H-indol-5-ylamino)-6-(2,4-difluorophenylsulfonyl)-8-methylpyrido[2,3-d]pyrimidin-7(8H)-one, or pharmaceutically acceptable salt thereof.

45. The method according to claim 43, wherein the leukemia is chronic myeloid leukemia, acute lymphoid leukemia, acute lymphocytic leukemia or chronic lymphoid leukemia.

46. The method according to claim 43, wherein the lymphoma is Burkitt's lymphoma or mantle cell lymphoma.

47. A method of inducing apoptosis of cancer cells in an individual afflicted with a cancer selected from the group consisting of ovarian cancer, cervical cancer, breast cancer, prostate cancer, lung cancer, colorectal cancer, skin cancer, brain cancer, pancreatic cancer, osteosarcoma, multiple myeloma, leukemia and lymphoma, comprising administering to the individual an effective amount of at least one compound according to claim 1, or a pharmaceutically acceptable salt thereof.

48. The method according to claim 47 wherein the compound is 2-(1H-indol-5-ylamino)-6-(2,4-difluorophenylsulfonyl)-8-methylpyrido[2,3-d]pyrimidin-7(8H)-one, or pharmaceutically acceptable salt thereof.

49. The method of claim 47, wherein the cancer cells are tumor cells.

50. A method according to claim 49, wherein the tumor cells are selected from the group consisting of ovarian, cervical, breast, prostate, lung, colorectal, skin and brain tumor cells.

51. A method of treating an individual suffering from a cancer selected from the group consisting of ovarian cancer, cervical cancer, breast cancer, prostate cancer, lung cancer, colorectal cancer, skin cancer, brain cancer, pancreatic cancer, osteosarcoma, multiple myeloma, leukemia and lymphoma, comprising administering to the individual an effective amount of at least one antibody conjugate according to claim 36, or a pharmaceutically acceptable salt thereof.

52. A process for preparing a compound according to claim 1 having the formula I-a:

I-a

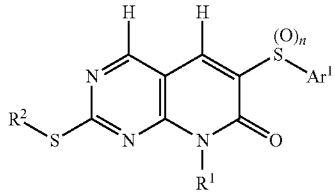

comprising:

(1) treating an aldehyde of the formula:

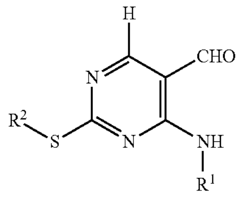

with an arylsulfonylacetic acid or ester of the formula $Ar^1$—$SO_2$—$CH_2CO_2R$, wherein R is hydrogen or ($C_1$-$C_6$)alkyl; and (2) isolating from the reaction products a compound of formula I-a, or a salt of such a compound.

53. The process according to claim 52 wherein n is 2, $R^1$ is methyl, $R^2$ is methyl, and $Ar^1$ is 2,4-difluorophenyl.

54. A process for preparing a compound according to claim 1 having the formula I-b:

I-b

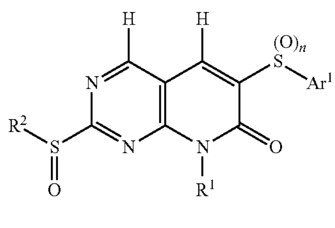

comprising:

(1) treating a compound of formula I-a, or a salt thereof,

I-a

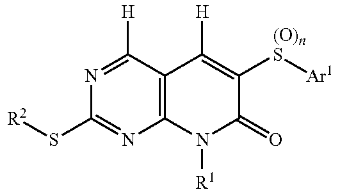

with an oxidizing agent capable of oxidizing a sulfide to a sulfoxide; and (2) isolating from the reaction products a compound of formula I-b, or a salt of such a compound.

55. The process according to claim 54, wherein n is 2, $R^1$ is methyl, $R^2$ is methyl and $Ar^1$ is 2,4-difluorophenyl.

56. A process for preparing a compound according to claim 21 having the formula III:

III

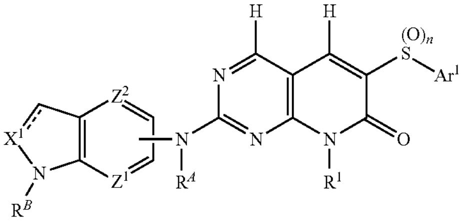

comprising, (1) treating a compound of formula I-b, or a salt thereof,

I-b

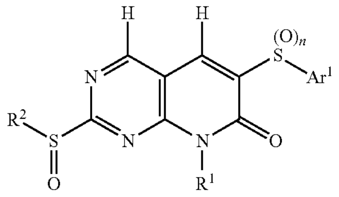

with an amine of the formula A:

A

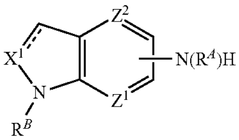

wherein:

$X^1$ is selected from the group consisting of nitrogen, $CR^5$, and C(═O);

$Z^1$ is nitrogen or $CR^5$;

$Z^2$ is nitrogen or $CR^5$;

$R^B$ is selected from the group consisting of hydrogen, ($C_1$-$C_6$)alkyl, ($C_1$-$C_6$)acyl, unsubstituted —C(═O)—($C_6$-$C_{10}$)aryl, substituted —C(═O)—($C_6$-$C_{10}$)aryl, unsubstituted —$(CH_2)_q$—($C_6$-$C_{10}$)aryl, substituted —$(CH_2)_q$—($C_6$-$C_{10}$)aryl, and —C(═O)O—($C_1$-$C_6$) alkyl; wherein the substituted —C(═O)—($C_6$-$C_{10}$)aryl and substituted —$(CH_2)_q$—($C_6$-$C_{10}$)aryl groups are substituted with one or more substituents independently selected from the group consisting of $(C_1-C_6)$alkyl; $(C_2-C_6)$alkenyl; $(C_2-C_6)$alkynyl; halogen; —C≡N; —$NO_2$; —C(═O)$R^3$; —C(═O)$OR^3$; —C(═O)$NR^3{}_2$; —C(═$NR^3$)$NR^3{}_2$; —$OR^3$; —OC(═O)$(C_1-C_6)$alkyl; —OC(═O)O$(C_1-C_6)$alkyl; —OC(═O)$NR^3{}_2$; —$NR^3{}_2$; —$NR^3$C(═O)$R^3$; —$NR^3$C(═O)O$(C_1-C_6)$alkyl; —$NR^3$C(═O)$NR^3{}_2$; —$NR^3SO_2R^3$; —$SR^3$; —S(O)$R^3$; —$SO_2R^3$; —$OSO_2(C_1-C_6)$alkyl; —$SO_2NR^3{}_2$; $(C_2-C_9)$heterocyclyl; $(C_1-C_3)$perfluoroalkyl; —$(C_2-C_6)$ alkylene-$OR^3$; —O$(C_2-C_6)$alkylene-N($(C_1-C_6)$alkyl$)_2$; —P(═O)$(OR^4)_2$; and —OP(═O)$(OR^4)_2$; and q is 1, 2, 3, or 4; and (2) isolating from the reaction products a compound of formula III, or a salt of such a compound.

57. The process according to claim 56, wherein n is 2, $R^1$ is methyl, $R^2$ is methyl, $Z^1$ is carbon, $Z^2$ is carbon, $R^A$ is hydrogen, $R^B$ is hydrogen and $Ar^1$ is 2,4-difluorophenyl.

58. The process according to claim 57 wherein the amine of formula A is 5-aminoindole.

* * * * *

UNITED STATES PATENT AND TRADEMARK OFFICE

CERTIFICATE OF CORRECTION

PATENT NO. : 8,889,696 B2
APPLICATION NO. : 13/516883
DATED : November 18, 2014
INVENTOR(S) : E. Premkumar Reddy et al.

It is certified that error appears in the above-identified patent and that said Letters Patent is hereby corrected as shown below:

On the Title Page item (57),

In the Abstract, that portion of formula I reading “ 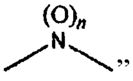 ” should read -- 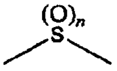 --.

In the Specification,

Col. 2, line 5, that portion of formula I reading “ 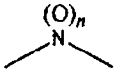 ” should read -- 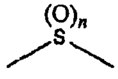 --.

Signed and Sealed this
Twenty-fourth Day of March, 2015

Michelle K. Lee
*Director of the United States Patent and Trademark Office*